(12) United States Patent
McCulloch et al.

(10) Patent No.: US 9,539,303 B2
(45) Date of Patent: Jan. 10, 2017

(54) TREATMENT OF RAS-EXPRESSING TUMORS

(75) Inventors: William McCulloch, Raleigh, NC (US); Mitchell Keegan, Berlin, MA (US)

(73) Assignee: Celgene Corporation, Summit, NJ (US)

(*) Notice: Subject to any disclaimer, the term of this patent is extended or adjusted under 35 U.S.C. 154(b) by 941 days.

(21) Appl. No.: 12/298,436

(22) PCT Filed: Apr. 13, 2007

(86) PCT No.: PCT/US2007/009294
§ 371 (c)(1),
(2), (4) Date: Jun. 3, 2009

(87) PCT Pub. No.: WO2008/013589
PCT Pub. Date: Jan. 31, 2008

(65) Prior Publication Data
US 2009/0305956 A1 Dec. 10, 2009

Related U.S. Application Data

(60) Provisional application No. 60/794,599, filed on Apr. 24, 2006.

(51) Int. Cl.
A61K 38/12 (2006.01)
A61K 31/7068 (2006.01)
A61K 38/15 (2006.01)
A61K 45/06 (2006.01)

(52) U.S. Cl.
CPC .......... *A61K 38/12* (2013.01); *A61K 31/7068* (2013.01); *A61K 38/15* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,977,138 A | 12/1990 | Okuhara | |
| 5,055,608 A | 10/1991 | Marks | |
| 5,369,108 A | 11/1994 | Breslow | |
| 5,508,269 A | 4/1996 | Smith | |
| 5,510,270 A | 4/1996 | Fodor et al. | |
| 5,545,522 A | 8/1996 | Van Gelder et al. | |
| 5,556,752 A | 9/1996 | Lockhart et al. | |
| 5,578,832 A | 11/1996 | Trulson et al. | |
| 5,605,793 A | 2/1997 | Stemmer | |
| 5,608,108 A | 3/1997 | Marks | |
| 5,700,811 A | 12/1997 | Breslow | |
| 5,716,785 A | 2/1998 | Van Gelder et al. | |
| 5,767,068 A | 6/1998 | VanDevanter | |
| 5,773,474 A | 6/1998 | Breslow | |
| 5,776,905 A | 7/1998 | Gibbons et al. | |
| 5,830,721 A | 11/1998 | Stemmer | |
| 5,837,458 A | 11/1998 | Minshull | |
| 5,891,636 A | 4/1999 | Van Gelder et al. | |
| 5,932,616 A | 8/1999 | Breslow | |
| 6,014,969 A | 1/2000 | Lloyd | |
| 6,117,679 A | 9/2000 | Stemmer | |
| 6,391,640 B1 | 5/2002 | Minshull | |
| 6,403,555 B1 | 6/2002 | Skov | |
| 6,511,990 B1 | 1/2003 | Breslow | |
| 6,548,479 B1 | 4/2003 | Skov et al. | |
| 6,602,883 B1* | 8/2003 | Bhide et al. .................. 514/311 |
| 6,706,686 B2 | 3/2004 | Long | |
| 6,777,217 B1 | 8/2004 | Schreiber | |
| 6,809,118 B2 | 10/2004 | Chung | |
| 6,828,302 B1 | 12/2004 | Skov | |
| 6,905,669 B2 | 6/2005 | DiMartino | |
| 6,946,441 B2 | 9/2005 | Long | |
| 7,041,639 B2 | 5/2006 | Skov | |
| 7,056,883 B2 | 6/2006 | Ito | |
| 7,056,884 B2 | 6/2006 | Nakajima | |
| 7,148,204 B2 | 12/2006 | Bennett et al. | |
| 7,171,311 B2 | 1/2007 | Dai et al. | |
| 7,314,862 B2 | 1/2008 | Naoe | |
| 7,354,928 B2 | 4/2008 | Wang et al. | |
| 7,396,665 B2 | 7/2008 | Ueda | |
| 7,470,722 B2 | 12/2008 | Malecha | |
| 7,488,712 B2 | 2/2009 | Yoshida | |
| 7,857,804 B2 | 12/2010 | McCaffrey et al. | |
| 2002/0156013 A1* | 10/2002 | Renauld et al. ............... 514/12 |
| 2003/0162293 A1 | 8/2003 | Chu | |
| 2004/0018968 A1 | 1/2004 | Sgouros | |
| 2004/0053820 A1 | 3/2004 | Nakajima | |
| 2004/0072735 A1 | 4/2004 | Richon | |
| 2004/0077591 A1 | 4/2004 | Dangond | |
| 2004/0127523 A1 | 7/2004 | Bacopoupos | |
| 2004/0228909 A1 | 11/2004 | Sarris | |
| 2005/0059682 A1 | 3/2005 | Rubinfeld | |

(Continued)

FOREIGN PATENT DOCUMENTS

| | | |
|---|---|---|
| CA | 2317003 | 8/2001 |
| EP | 0352646 | 1/1990 |

(Continued)

OTHER PUBLICATIONS

US 5,171,191, 12/1992, Marks (withdrawn)
Lowell et al., Experimentla and Molecular Therapeutics 32: Tareting Multiple Levels in Molecular Therapeutics, Abstract 3829, Proc. Amer Assoc Cancer Res, vol. 47, 2006.*
Fecteau et al., The Journal of Pharmacology and Experimental Therapeutics, vol. 300, No. 3, 2002, pp. 890-899.*
Nemunaitis et al., The Cancer Journal, vol. 9, No. 1, 2003, pp. 58-66.*
Kelly et al., Expert Opinion Investig Drugs, 2002, 11(12), pp. 1695-1713.*
Piekarz et al., Blood, 2001, 98:2865-2868.*
Zinzani et al. (1) Journal of Clinical Oncology, vol. 18(13), 2000.*
Zinzani et al. (2) Annals of Oncology, 9: 1351-1353, 1998.*
Andrews et al., Int J Parasitol 30:761, 2000.
Aron et al., Blood 102(2):652-658, 2003.
Bates et al., "A Phase I Study of FR901228 (Depsipeptide), A Histone Deacetylase Inhibitor (Meeting Abstract)", 1999 ASCO Annual Meeting, Clinical Pharmacology, abs. 693.
Bates et al., ASH Annual Meeting Abstracts 112 (11):1568, 2008.
Berge et al., J Pharm Sciencse 66:1-19, 1977.
Bishton et al., Expert Rev Anticancer Ther 7(10):1439-1449, 2007.
Bhalla, J Clin Oncol 23(17):3971-3993, 2005.
Bogden et al., Exp Cell Biol 47:281-293. 1979.

(Continued)

*Primary Examiner* — Traviss C McIntosh, III
(74) *Attorney, Agent, or Firm* — Jones Day

(57) ABSTRACT

The present invention provides compositions and methods for the treatment of /?αs-expressing tumors using at least one DAC inhibitor (e.g., romidepsin).

15 Claims, 26 Drawing Sheets

(56) References Cited

U.S. PATENT DOCUMENTS

| | | |
|---|---|---|
| 2005/0070467 A1 | 3/2005 | Naoe |
| 2005/0187148 A1 | 8/2005 | Naoe |
| 2005/0187149 A1 | 8/2005 | Naoe |
| 2005/0191713 A1 | 9/2005 | Sasakawa |
| 2005/0222013 A1 | 10/2005 | Jung |
| 2005/0272647 A1 | 12/2005 | Yamaji |
| 2006/0018921 A1 | 1/2006 | Levenson |
| 2006/0019883 A1 | 1/2006 | Kronblad |
| 2006/0100140 A1 | 5/2006 | Dent |
| 2006/0106049 A1 | 5/2006 | Odenike |
| 2006/0128660 A1 | 6/2006 | Rajski |
| 2006/0135413 A1 | 6/2006 | Naoe |
| 2006/0223747 A1 | 10/2006 | Ito |
| 2006/0270016 A1 | 11/2006 | Holm |
| 2007/0015787 A1 | 1/2007 | Bruncko |
| 2007/0110719 A1 | 5/2007 | Holm |
| 2007/0129290 A1 | 6/2007 | Or |
| 2007/0148228 A1 | 6/2007 | Cumming |
| 2007/0292512 A1 | 12/2007 | Leonard |
| 2008/0214446 A1 | 9/2008 | Okada |
| 2008/0233562 A1 | 9/2008 | Sasakawa |
| 2009/0186382 A1 | 7/2009 | Verdine |
| 2009/0209616 A1 | 8/2009 | Verdine |
| 2009/0221473 A1 | 9/2009 | Chan |
| 2010/0093610 A1 | 4/2010 | Vrolijk |

FOREIGN PATENT DOCUMENTS

| | | |
|---|---|---|
| EP | 1010705 | 6/2000 |
| EP | 1426054 | 6/2004 |
| JP | 7-1995-64872 | 2/1995 |
| JP | 11-335375 | 12/1999 |
| JP | 2001-348340 | 12/2001 |
| WO | 97/11366 | 3/1997 |
| WO | 98/40080 | 3/1998 |
| WO | 98/39965 | 9/1998 |
| WO | 98/43650 | 10/1998 |
| WO | 98/48825 | 11/1998 |
| WO | 00/08048 | 2/2000 |
| WO | 00/21979 | 4/2000 |
| WO | 00/71703 | 11/2000 |
| WO | 01/18171 | 3/2001 |
| WO | 01/38322 | 5/2001 |
| WO | 01/42282 | 6/2001 |
| WO | 01/70675 | 9/2001 |
| WO | 02/06307 | 1/2002 |
| WO | 02/15921 | 2/2002 |
| WO | 02/20817 | 3/2002 |
| WO | 02/22577 | 3/2002 |
| WO | 02/30879 | 4/2002 |
| WO | WO 02/86498 | 4/2002 |
| WO | WO 02/97053 | 5/2002 |
| WO | 02/46144 | 6/2002 |
| WO | 02/055017 | 7/2002 |
| WO | 02/055688 | 7/2002 |
| WO | 02/085400 | 10/2002 |
| WO | 02/090534 | 11/2002 |
| WO | 03/015810 | 2/2003 |
| WO | 03/017763 | 3/2003 |
| WO | 03/024442 | 3/2003 |
| WO | 03/035843 | 5/2003 |
| WO | 03/053468 | 7/2003 |
| WO | 03/070188 | 8/2003 |
| WO | 03/083067 | 10/2003 |
| WO | 03/084611 | 10/2003 |
| WO | 03/088954 | 10/2003 |
| WO | 03/103613 | 12/2003 |
| WO | 2004/009771 | 1/2004 |
| WO | 2004/017996 | 3/2004 |
| WO | 2004/024160 | 3/2004 |
| WO | 2004/062654 | 7/2004 |
| WO | 2004/064727 | 8/2004 |
| WO | 2004/074478 | 9/2004 |
| WO | 2004/096289 | 11/2004 |
| WO | 2004/098495 | 11/2004 |
| WO | 2005/000282 | 1/2005 |
| WO | 2005/000289 | 1/2005 |
| WO | 2005/000332 | 1/2005 |
| WO | 2005/009961 | 2/2005 |
| WO | 2005/018578 | 3/2005 |
| WO | 2005/023179 | 3/2005 |
| WO | 2005/027842 | 3/2005 |
| WO | 2005/030239 | 4/2005 |
| WO | 2005/051430 | 6/2005 |
| WO | 2005/052143 | 6/2005 |
| WO | 2005/053609 | 6/2005 |
| WO | WO 2005/058298 | 6/2005 |
| WO | 2005/079827 | 9/2005 |
| WO | 2005/085864 | 9/2005 |
| WO | 2005/087206 | 9/2005 |
| WO | 2005/105055 | 11/2005 |
| WO | 2005/105066 | 11/2005 |
| WO | 2005/115149 | 12/2005 |
| WO | WO 2005/117930 | 12/2005 |
| WO | 2006/027346 | 3/2006 |
| WO | 2006/055621 | 5/2006 |
| WO | 2006/060382 | 6/2006 |
| WO | 2006/060429 | 6/2006 |
| WO | 2006/129105 | 12/2006 |
| WO | 2007/009539 | 1/2007 |
| WO | 2007/040522 | 4/2007 |
| WO | WO 2007040522 | 4/2007 |
| WO | 2007/058896 | 5/2007 |
| WO | 2007/061939 | 5/2007 |
| WO | 2007/145704 | 12/2007 |
| WO | 2007/146730 | 12/2007 |
| WO | 2008/013589 | 1/2008 |

OTHER PUBLICATIONS

Bolden et al., Nat Rev Drug Discovery 5(9):769-784, 2006.
Brosch et al., Plant Cell 7:1941, 1995.
Budillon et al., Eur J Cancer 38:S29, 2002 (XP-004403521).
Bundgaard et al., J Drug Deliver Reviews 8:1-38, 1992.
Butler et al., Cancer Res 60:5165-5170, 2000.
Byrd et al., Blood 94(4):1401-1408, 1999.
Byrd et al., Blood 105(3):959-967, 2005.
Catley et al., Blood 108(10):3441-3449, 2006.
Chan et al., Invest New Drugs 15(3):195-206, 1997.
Cheson et al., Reviews Clin Exp Hematol 4(2):145-166, 2000.
Conway et al., Eur J Cancer 34(11):1741-1748, 1998 (XP-004285125).
Corbett et al., In: Anticancer Drug Development Guide, Teicher B., Ed., Totowa, N.J.:Humana, 2004:99-123.
Cousens et al., J Biol Chem 254:1716, 1979.
Curtin, Expert Opin Ther Patents 12(9):1375-1384, 2002.
Dai et al., Clin Cancer Res 14(2):549-558, 2008.
Darkin-Rattray et al., PNAS USA 93:13143, 1996.
Database Biosis Online, AN-PREV200400024248, XP-002342749, "Anti-Tumor Efficacy of Four Different Histone Deacetylase Inhibitors on Hepatoma Cells in Vitro", 2003 (Abstract No. T1786).
Dokmanovic & Marks, J Cell Biochem 96(2):293-304, 2005.
Fecteau et al., J Pharmacol & Exp Therapeutics 300(3):890-899, 2002.
Fiebig et al., Cancer 6:213, 2006.
Finnin et al., Nature 401(6749):188-193, 1999.
Fischer et al., 41st Annual Meeting of the American Society of Clinical Oncology, Abstr # 3106, 2005.
Frey et al., Bioorg & Med Chem Lett 12:3443, 2002.
Furamai et al., PNAS USA 98(1):87-92, 2001.
Furumai et al., Cancer Res 62(17):4916-4921, 2002.
Garcia-Manero et al., Blood 108(10):3271-3279, 2006.
Geldof et al., Cancer Chemother & Pharmacol 44(4):312-318, 1999.
Goldin et al., Eur J Cancer 17:129-142, 1981.
Gore et al., Clin Cancer Res 7(8):2330-2339, 2001.
Gore et al., Cancer Res 66(12):6361-6369, 2006.
Guan et al., Cancer Res 60:749, 2000.
Han et al., Cancer Res 60(21):6068-6074, 2000.

Harrison et al., ASH Annual Meeting Abstracts 112(11):3698, 2008.
Inoue et al., Gan to Kagaku Ryoho 14(5Pt2):1629-1635, 1987 (Abstract).
Jung et al., J Med Chem US 42(22):4669-4679, 1999.
Jones & Baylin, Nat Rev Genet 3(6):415-428, 2002.
Jones & Baylin, Cell 128:683-692, 2007.
Kano et al., Japanese J Clin Hematology 43(8):116, 2002.
Khan et al., Br J Haematol 125(2):156-161, 2004.
Kahn et al, J. Am Chem Soc 118:7237-7238, 1996.
Kijima et al., J Biol Chem 268:22429, 1993.
Kim et al., Oncogene 18:2461, 1999.
Kim et al., ASH Annual Meeting Abstracts 112(11):263, 2008.
Kisselev & Goldberg, Chem Biol 8:839-758, 2001.
Kitazono et al., Cancer Res 61:6328-6330, 2001.
Kitazono et al., Int J Cancer 99:453-459, 2002.
Kitazono et al., Proc Amer Assoc Cancer Res Annual 43:799, 2002 (Abstract only).
Kitazono et al., J Clin Endocrin 86(7):3430-3435, 2001.
Klimek et al., Clin Cancer Res 14(3):826-832, 2008.
Klisovic et al., Invest Ophthalmol Vis Sci 44(6):2390-2398, 2003.
Koghe et al., Biochem Pharmacol 56:1359, 1998.
Komatsu et al., Cancer Res 61(11):4459-4466, 2001.
Kosugi et al., Japanese J Cancer Res 92(5):529-536, 2001.
Kuendgen et al., Blood 104(5):1266-1269, 2004.
Kwon et al., Proceedings of Nat Acad Sci USA 95:3356, 1998.
Lan et al., Cancer Res 50:2997-3001, 1990.
Lea & Tulsyan, Anticancer Res 15:879, 1995.
Lee et al., Cancer Res 61(3):931-934, 2001.
Lieber et al., Int J Cancer 15:741-747, 1975.
Loor et al., Clin Lab Med 2:567-578, 1982.
Maeda et al., Blood 96(12):3847-3856, 2000.
Magner et al., J Immunol 165(12):7017-7024, 2000.
Marks et al., J Natl Cancer Inst 92(15):1210-1216, 2000.
Marshall et al., J Exp Ther Oncol 2(6):325-332, 2002.
McBain et al., Biochem Pharm 53:1357, 1997.
Mertins et al., Proc Amer Assoc Cancer Res Annual Meetins 40:623, 1999.
Mitsiades et al., Proc Natl Acad Sci USA 101(2):540-545, 2004.
Molife et al., J Clin Oncol (Meeting Abstracts) 24(18 Suppl):14554, 2006.
Murata et al., Japanese J Cancer Res 91:1154-1160, 2000.
Nakajima et al., Exp Cell Res 241(1)126-133,1998.
Nebbioso et al., Nat Med 11(1):77-84, 2005.
Nebozhyn et al., Blood 107(8):3189-3196, 2006.
Newbold et al., Mol Cancer Ther 7(5):1066-1079, 2008.
Nielsen et al., J Pharm Sciences 77:285, 1988.
Niesvizky et al., Blood ASH Annual Meeting Abstracts 106(11);2574, 2005.
Nishimura et al., J Antibiot XLII(4):553-557, 1989.
Nuijen et al., Medline, 2001, XP-002206588.
Odenike et al., Clin Cancer Res 14(21):7095-7101, 2008.
Qiu et al., Mol Biol Cell 11:2069, 2000.
Paoluzzi et al., Clin Cancer Res 16(2):554-565, 2010.
Peart et al., Cancer Res 63(15):4460-4471, 2003.
Peart et al., Proc Natl Acad Sci USA 102(10):3697-3702, 2005.
Pei et al., Clin Cancer Res 10(11):3839-3852, 2004.
Piekarz et al., Blood 98(9):2865-2868, 2001.
Piekarz et al., Blood 103(12):4636-4643, 2004.
Piekarz et al.,Curr Pharm Des 10:2289-2298, 2004.
Piekarz et al., ASH Annual Meeting Abstracts 106(11):231, 2005.
Piekarz et al., Clin Cancer Res 12(12):3762-3773, 2006.
Piekarz et al., J Clin Oncol (Meeting Abstracts) 25(18 Suppl):8027, 2007.
Piekarz et al., ASH Annual Meeting Abstracts 112(11):1567, 2008.
Piekarz et al., Clin Cancer Res 15(12):3918-3926, 2009.
Piekarz et al., J Clin Oncol 27(32):5410-5417, 2009.
Prince et al., Clin Cancer Res 15(12):3958-3969, 2009.
Programme of the 4th Japanese Foundation for Cancer Research, International Symposium on Cancer Therapy (ISCC), Feb. 12, 1999.
Rasheed et al., Expert Opin Investig Drugs 16(5):659-678, 2007.
Richon et al., PNAS USA 95:3003, 1998.
Richon et al., Proc Natl Acad Sci USA 97(18):10014-10019, 2000.
Richon et al., Clin Cancer Res 8(3):662-664, 2002.
Robey et al., Clin Cancer Res 12(5):1547-1555, 2006.
Roychowdhury et al., J Natl Cancer Inst 96(19):1447-1457, 2004.
Saito et al., PNAS USA 96:4592-4597, 1999.
Sakai et al., J Biol Chem 277(50):48714-48723, 2002.
Sandor et al., Br J Cancer 83(6):817-825, 2000.
Sandor et al., Clin Cancer Res 8(3):718-728, 2002.
Sasakawa et al., Biochem Pharmacol 64(7):1079-1090, 2002.
Sawa et al., Proc of Japanese Cancer Assoc 60:597, 2001 (w/English translation).
Sawa et al., Acta Neuropathol (Berlin) 107(6):523-531, 2004.
Schrump et al., Clin Cancer Res 14(1):188-198, 2008.
Schwartsmann et al., The Lancet Oncology 2(4):221-225, 2001.
Schwarz et al., Cancer Lett 107(2)285-291, 1996.
Sreedharan et al., Proc Amer Assoc Cancer Res 44(2 ed.):742, 2003 (XP-001154773).
Stadler et al., Clin Genitourin Cancer 5(1):57-60, 2006.
Su et al., Cancer Res 60:3137-3142, 2000.
Su et al., J Clin Oncol (Meeting Abstracts) 24(18 Suppl):5554, 2006.
Sutheesophon et al., Acta Haematol 115(1-2):78-90, 2006.
Suzuki et al., J Med Chem 42(15):3001-3003, 1999.
Ueda et al., PNAS USA 84:3004, 1987.
Ueda et al., J Antibiot (Tokyo) 47:301-310, 1994.
Ueda et al., J Antibiot (Tokyo) 47:315-323, 1994.
Ueda et al., Biosci Biotechnol Biochem 58(9):1579-1583, 1994.
Vrana et al., Oncogene 18(50):7016-7025, 1999.
Wang et al., Oncogene 17:1503-1508, 1998.
Wang et al., Cancer Res 59:2766, 1999.
Watanabe et al., Int J Cancer 124(1):55-67, 2009.
Weidle et al. Anticancer Res 20:1471-1486, 2000.
Whitehead et al., J Clin Oncol (Meeting Abstracts) 24(18 Suppl):3598, 2006.
Whittaker et al., J Clin Oncol (Meeting Abstracts) 24(18 Suppl):3063, 2006.
Wu et al., Int J Cancer 22:728-733, 1978.
Xiao et al., Rapid Commun Mass Spectrom 17:757-766, 2003.
Xiao et al.,J Pharm & Exp Therapeutics 313(1):268-276, 2005.
Yasui et al., Invasion Metastasis 17:259-269, 1997.
Yoshida et al., Bioassays 17:423-430, 1995.
Yu et al., Blood 102(10):3765-3774, 2003.
Fuino et al., "Histone deacetylase inhibitor LAQ824 down-regulates HER-2 and sensitizes human breast cancer cells to trastuzumab, taxotere, gemcitabine, and epothilone B," Molecular Cancer Therapeutics, American Association of Cancer Research, 2(10): 971-984 (2003).
Jones et al., "Phase 1 results from a study of romidepsin in combination with gemcitabine in patients with advanced solid tumors", Cancer Investigation, 30:481-486 (2012).
Piacentini et al., "Trichostatin A enhances the response of chemotherapeutic agents in inhibiting pancreatic cancer cell proliferation," Virchows Archiv, 448(6): 797-804 (2006).
U.S. Appl. No. 12/298,265 Non final office action dated Nov. 29, 2011.
Findley et al., "Expression and Regulation of Bcl-2, Bcl-xl, and Bax Correlate With p53 Status and Sensitivity to Apoptosis in Childhood Acute Lymphoblastic Leukemia," Blood, 89(8): 2986-2993 (1997).
Fukumura et al., "A sensitive transcriptome analysis method that can detect unknown transcripts," Nucl Acids Res 31(16):e94 (2003).

Kawamoto et al., "Expression Profiling by iAFLP: A PCR-Based Method for Genome-Wide Gene Expression Profiling," Genome Res 12:1305-1312 (1999).

Liakopoulou et al., "Stimulation of Fetal Hemoglobin Production by Short Chain Fatty Acids," Blood, 86:3227 (1995).

Non final office action dated Nov. 29, 2011, for U.S. Appl. No. 12/298,265.

Non final office action dated Sep. 27, 2012, for U.S. Appl. No. 13/482,940.

Non final office action dated Jan. 8, 2014, for U.S. Appl. No. 13/851,053.

Non final office action dated Dec. 20, 2013, for U.S. Appl. No. 13/124,838.

Non final office action dated Jul. 12, 2013, for U.S. Appl. No. 13/229,581.

Notice of Allowance dated Jan. 9, 2014, for U.S. Appl. No. 13/229,581.

Notice of Allowance dated May 13, 2014, for U.S. Appl. No. 13/229,581.

Non final office action dated Oct. 17, 2013, for U.S. Appl. No. 13/627,848.

Final office action dated Apr. 2, 2014, for U.S. Appl. No. 13/627,848.

\* cited by examiner

MGCD0103

Chemical Formula: $C_{23}H_{20}N_6O$
Molecular Weight: 396.44
Log P: 2.6
PSA: 104.7 $Å^2$
M.p. 191.5-194.5°C

TREATMENT OF RAS-EXPRESSING TUMORS

RELATED APPLICATIONS

The present application is a U.S. national phase application under 35 U.S.C. §371 of international PCT application number PCT/US2007/009294, filed Apr. 13, 2007, which claims priority under 35 U.S.C. §119(e) to U.S. provisional application, U.S. Ser. No. 60/794,599, filed Apr. 24, 2006, which is incorporated herein by reference.

BACKGROUND OF THE INVENTION

Dysregulation or loss of control of cell division can result in the development of any of a variety of cell proliferative disorders, many of which are debilitating or deadly. Although much has been learned about mechanisms involved in cell proliferation, and therefore about common biological principles underlying a variety of different disorders, there remains a need for the development of new and/or improved therapies for the treatment of such conditions.

There is a particular need for the development of improved therapies for the treatment of tumors that express the Ras oncogene. Ras-expressing tumors are often more resistant to standard therapies. Furthermore, many of the most deadly cancers involve Ras-expressing tumors. For example, 90-95% of pancreatic tumors are Ras-expressing. Similarly, 40-45% of colorectal tumors, 40% of bladder tumors, 15-20% of non small cell lung carcinomas express Ras. Indeed, 10-25% of myelodysplastic syndromes (MDS), which are not themselves cancer but are bone marrow disorders characterized by abnormal cell maturation that typically progress to cancer (AML), also express Ras. There is a profound need for the development of therapies for these and other Ras-expressing diseases and disorders.

SUMMARY OF THE INVENTION

The present invention encompasses the finding that DAC inhibitors can show selective potency against Ras-expressing tumors. In certain embodiments, the DAC inhibitor is romidepsin. The present invention provides methods of treating tumors that express the Ras oncogene by administering a DAC inhibitor. In some embodiments, such methods involve determining that a tumor expresses the Ras oncogene, and then, administering a DAC inhibitor. Determination that a tumor expresses the Ras oncogene can involve testing for expression of the Ras oncogene and/or can involve determining that the tumor is of a type that typically expresses the Ras oncogene.

The present invention also demonstrates that combinations of DAC inhibitors with gemcitabine are particularly effective in the treatment of Ras-expressing tumors. In certain particular embodiments, combination therapy with romidepsin and gemcitabine is provided, for example for use in the treatment of tumors expressing the Ras oncogene.

The present invention provides combination regimens, and unit dosages of pharmaceutical compositions useful in such regimens. The present invention further provides kits for treatment of Ras-expressing tumors with at least one DAC inhibitor (e.g., romidepsin).

DEFINITIONS

Figure 1:
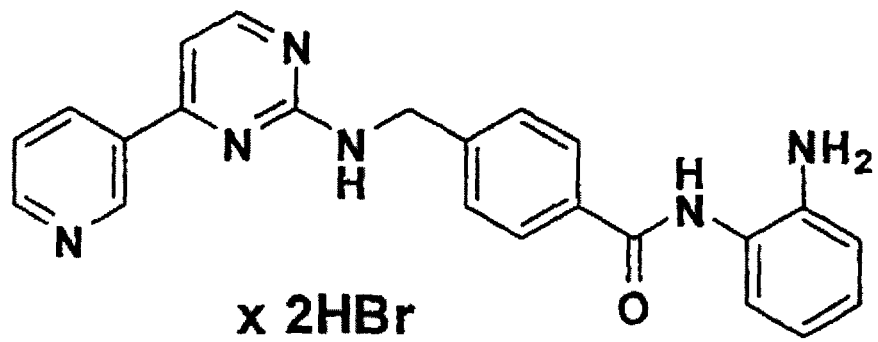
FIGS. 1-3 depict structures of certain DAC inhibitors that, like other DAC inhibitors available in the art and/or described herein, may be utilized in some embodiments of the present invention.

Alicyclic: The term "alicyclic," as used herein, denotes a monovalent group derived from a monocyclic or bicyclic saturated carbocyclic ring compound by the removal of a single hydrogen atom. Examples include, but not limited to, cyclopropyl, cyclobutyl, cyclopentyl, cyclohexyl, bicyclo[2.2.1]heptyl, and bicyclo[2.2.2]octyl. Such alicyclic groups may be further substituted.

Aliphatic: An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted.

Aryl: The term "aryl," as used herein, refers to a mono- or polycyclic carbocyclic ring system having one or two aromatic rings including, but not limited to, phenyl, naphthyl, tetrahydronaphthyl, indanyl, idenyl and the like. In accordance with the invention, any of the aryls, substituted aryls, heteroaryls and substituted heteroaryls described herein, can be any aromatic group; Aromatic groups can be substituted or unsubstituted.

Cell Proliferative Disorder, Disease, or Condition: The term "cell proliferative disease or condition" is meant to refer to any condition characterized by aberrant cell growth, preferably abnormally increased cellular proliferation.

Combination Therapy: According to some embodiments of the present invention, a DAC inhibitor may desirably be administered in combination with one or more other therapeutic agents. Such therapy will commonly involve administration of multiple individual doses of a DAC inhibitor and/or of other agent, spaced out over time. Doses of a DAC inhibitor and other agent may be administered in the same amounts and/or according to the same schedule or alternatively may be administered in different amounts and/or according to different schedules.

DAC Inhibitor: In general, any agent that specifically inhibits a deacetylase is considered to be a DAC inhibitor. Any agent that specifically inhibits a histone deacetylase is considered to be an HDAC inhibitor. Those of ordinary skill in the art will appreciate that, unless otherwise set forth herein or known in the art, DAC inhibitors may be administered in any form such as, for example, salts, esters, prodrugs, metabolites, etc. Furthermore, DAC inhibitors that contain chiral centers may be administered as single stereoisomers or as mixtures, including racemic mixtures, so long as the single stereoisomer or mixture has DAC inhibitor activity.

DAC Inhibitor Therapy: As used herein, the phrase "DAC inhibitor therapy" refers to the regimen by which a DAC inhibitor is administered to an individual. Commonly, DAC inhibitor therapy will involve administration of multiple individual doses of a DAC inhibitor, spaced out over time. Such individual doses may be of different amounts or of the same amount. Furthermore, those of ordinary skill in the art will readily appreciate that different dosing regimens (e.g., number of doses, amount(s) of doses, spacing of doses) are typically employed with different DAC inhibitors.

Electrolyte: In general, the term "electrolyte", as used herein, refers to physiologically relevant free ions. Representative such free ions include, but are not limited to sodium ($Na^+$), potassium ($K^+$), calcium ($Ca^{2+}$), magnesium ($Mg^{2+}$), chloride ($Cl^-$), phosphate ($PO4^{3-}$), and bicarbonate ($HCO_3^-$).

Electrolyte Supplementation: The term "electrolyte supplementation", as used herein, refers to administration to a subject of a composition comprising one or more electrolytes in order to increase serum electrolyte levels in the subject. For purposes of the present invention, when electrolyte supplementation is administered "prior to, during, or after" combination therapy, it may be administered prior to initiation of combination therapy inhibitor therapy (i.e., prior to administration of any dose) or prior to, concurrently with, or after any particular dose or doses.

Halogen: The term "halogen", as used herein, refers to an atom selected from fluorine, chlorine, bromine, and iodine.

Heteroaryl: The term "heteroaryl", as used herein, refers to a mono- or polycyclic (e.g. bi-, or tri-cyclic or more) aromatic radical or ring having from five to ten ring atoms of which one or more ring atom is selected from, for example, S, O and N; zero, one or two ring atoms are additional heteroatoms independently selected from, for example, S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

Heterocyclic: The term "heterocyclic" as used herein, refers to a non-aromatic 5-, 6- or 7-membered ring or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, (iv) any of the above rings may be fused to a benzene ring, and (v) the remaining ring atoms are carbon atoms which may be optionally oxo-substituted. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted.

Initiation: As used herein, the term "initiation" when applied to therapy can refer to a first administration of an active agent (e.g., a DAC inhibitor) inhibitor to a patient who has not previously received the active agent. Alternatively or additionally, the term "initiation" can refer to administration of a particular dose of a DAC inhibitor during therapy of a patient.

Pharmaceutically acceptable carrier or excipient: As used herein, the term "pharmaceutically acceptable carrier or excipient" means a non-toxic, inert solid, semi-solid or liquid filler, diluent, encapsulating material or formulation auxiliary of any type.

Pharmaceutically acceptable ester: As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

Pharmaceutically acceptable prodrug: The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of the invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., *Journal of Drug Deliver Reviews,* 8:1-38 (1992); Bundgaard, *J. of Pharmaceutical Sciences,* 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

Pharmaceutically acceptable salt: As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Stable: The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject). In general, combinations of substituents and variables envisioned by this invention are only those that result in the formation of stable compounds.

Substituted: The terms "substituted aryl", "substituted heteroaryl", or "substituted aliphatic," as used herein, refer to aryl, heteroaryl, aliphatic groups as previously defined, substituted by independent replacement of one, two, or three or more of the hydrogen atoms thereon with substituents including, but not limited to, —F, —Cl, —Br, —I, —OH, protected hydroxyl, —$NO_2$, —CN, —$C_1$-$C_{12}$-alkyl optionally substituted with, for example, halogen, $C_2$-$C_{12}$-alkenyl optionally substituted with, for example, halogen, —$C_2$-$C_{12}$-alkynyl optionally substituted with, for example, halogen, —$NH_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkenyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkenyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_{12}$-alkenyl, —CONH—$C_2$-$C_{12}$-alkenyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_{12}$-alkenyl, —$OCO_2$—$C_2$-$C_{12}$-alkenyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{12}$-alkyl, —OCONH—$C_2$-$C_{12}$-alkenyl, —OCONH—$C_2$-$C_{12}$-alkenyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkenyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_{12}$-alkenyl, —$NHCO_2$—$C_2$-$C_{12}$-alkenyl, —$NHCO_2$—$C_3$-$C_{12}$-cycloalkyl, —$NHCO_2$— aryl, —$NHCO_2$— heteroaryl, —$NHCO_2$— heterocycloalkyl, —NHC(O)$NH_2$, —NHC(O)NH—$C_1$-$C_{12}$-alkyl, —NHC(O)NH—$C_2$-$C_{12}$-alkenyl, —NHC(O)NH—$C_2$-$C_{12}$-alkenyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)$NH_2$, —NHC(S)NH—$C_1$-$C_{12}$-alkyl, —NHC(S)NH—$C_2$-$C_{12}$-alkenyl, —NHC(S)NH—$C_2$-$C_{12}$-alkenyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, —NHC(NH)NH—$C_1$-$C_{12}$-alkyl, —NHC(NH)NH—$C_2$-$C_{12}$-alkenyl, —NHC(NH)NH—$C_2$-$C_2$-alkenyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_{12}$-alkenyl, —NHC(NH)—$C_2$-$C_{12}$-alkenyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkenyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkenyl, —S(O)—$C_3$-$C_{12}$-cycloalkyl, —S(O)-aryl, —S(O)-heteroaryl, —S(O)-heterocycloalkyl —$SO_2NH_2$, —$SO_2$NH—$C_1$-$C_{12}$-alkyl, —$SO_2$NH—$C_2$-$C_{12}$-alkenyl, —$SO_2$NH—$C_2$-$C_{12}$-alkenyl, —$SO_2$NH—$C_3$-$C_{12}$-cycloalkyl, —$SO_2$NH-aryl, —$SO_2$NH— heteroaryl, —$SO_2$NH— heterocycloalkyl, —$NHSO_2$—$C_1$-$C_{12}$-alkyl, —$NHSO_2$—$C_2$-$C_{12}$-alkenyl, —$NHSO_2$—$C_2$-$C_{12}$-alkenyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkenyl, —S—$C_3$-$C_{12}$-cycloalkyl, —S-aryl, —S-heteroaryl, —S-heterocycloalkyl, or methylthiomethyl. It is understood that the aryls, heteroaryls, alkyls, and the like can be further substituted.

Susceptible to: The term "susceptible to", as used herein refers to an individual having higher risk (typically based on genetic predisposition, environmental factors, personal history, or combinations thereof) of developing a particular disease or disorder, or symptoms thereof, than is observed in the general population.

Therapeutically effective amount: The term "therapeutically effective amount" of an active agent or combination of agents is intended to refer to an amount of agent(s) which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of a particular agent may range from about 0.1 mg/Kg to about 500 mg/Kg, preferably from about 1 to about 50 mg/Kg. Effective doses may also vary depending on route of administration, as well as the possibility of co-usage with other agents. It will be understood, however, that the total daily usage of any particular active agent utilized in accordance with the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

Therapeutic agent: As used herein, the phrase "therapeutic agent" refers to any agent that, when administered to a subject, has a therapeutic effect and/or elicits a desired biological and/or pharmacological effect.

Treatment: As used herein, the term "treatment" (also "treat" or "treating") refers to any administration of a biologically active agent that partially or completely alleviates, ameliorates, relives, inhibits, delays onset of, reduces severity of and/or reduces incidence of one or more symptoms or features of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

DETAILED DESCRIPTION OF CERTAIN EMBODIMENTS OF THE INVENTION

As indicated, the present invention demonstrates that DAC inhibitors are specifically effective in inhibiting growth of cells that express Ras. According to the present invention, therefore, DAC inhibitors are useful in the treatment of cell proliferative disorders, diseases, or conditions that are associated with Ras expression. According to the present invention, DAC inhibitors are particularly useful in the treatment of Ras-expressing tumors.

Cell Proliferative Disorders, Diseases, or Conditions

In some embodiments, the invention provides methods for treating cell proliferative disorders, diseases or conditions, in particular where cells express the Ras oncogene.

In general, cell proliferative disorders, diseases or conditions encompass a variety of conditions characterized by aberrant cell growth, preferably abnormally increased cellular proliferation. For example, cell proliferative disorders, diseases, or conditions include, but are not limited to, cancer, immune-mediated responses and diseases (e.g., transplant rejection, graft vs host disease, immune reaction to gene therapy, autoimmune diseases, pathogen-induced immune dysregulation, etc.), certain circulatory diseases, and certain neurodegenerative diseases.

In certain embodiments, the invention relates to methods of treating cancer. In general, cancer is a group of diseases which are characterized by uncontrolled growth and spread of abnormal cells. Examples of such diseases are carcinomas, sarcomas, leukemias, lymphomas and the like.

For example, cancers include, but are not limited to leukemias and lymphomas such as cutaneous T-cell lymphomas (CTCL), peripheral T-cell lymphomas, lymphomas associated with human T-cell lymphotropic virus (HTLV) such as adult T-cell leukemia/lymphoma (ATLL), B-cell lymphoma, acute lymphocytic leukemia, acute nonlymphocytic leukemias, chronic lymphocytic leukemia, chronic myelogenous leukemia, acute myelogenous leukemia, Hodgkin's disease, non-Hodgkin's lymphomas, multiple myeloma, myelodysplastic syndrome, mesothelioma, common solid tumors of adults such as head and neck cancers (e.g., oral, laryngeal and esophageal), genitourinary cancers (e.g., prostate, bladder, renal, uterine, ovarian, testicular, rectal and colon), lung cancer, breast cancer, pancreatic cancer, melanoma and other skin cancers, stomach cancer, brain tumors, liver cancer and thyroid cancer, and/or childhood solid tumors such as brain tumors, neuroblastoma, retinoblastoma, Wilms' tumor, bone tumors, and soft-tissue sarcomas.

In some embodiments, the invention relates to treatment of leukemias. For example, in some embodiments, the invention relates to treatment of chronic lymphocytic leukemia, chronic myelogenous leukemia, acute lymphocytic leukemia, acute myelogenous leukemia, and/or adult T cell leukemia/lymphoma. In certain embodiments, the invention relates to the treatment of AML. In certain embodiments, the invention relates to the treatment of ALL. In certain embodiments, the invention relates to the treatment of CML. In certain embodiments, the invention relates to the treatment of CLL.

In some embodiments, the invention relates to treatment of lymphomas. For example, in some embodiments, the invention relates to treatment of Hodgkin's or non-Hodgkin's (e.g., T-cell lymphomas such as peripheral T-cell lymphomas, cutaneous T-cell lymphomas, etc.) lymphoma.

In some embodiments, the invention relates to the treatment of myelomas and/or myelodysplastic syndromes. In some embodiments, the invention relates to treatment of solid tumors. In some such embodiments the invention relates to treatment of solid tumors such as lung, breast, colon, liver, pancreas, renal, prostate, ovarian, and/or brain. In some embodiments, the invention relates to treatment of pancreatic cancer. In some embodiments, the invention relates to treatment of renal cancer. In some embodiments, the invention relates to treatment of prostate cancer. In some embodiments, the invention relates to treatment of sarcomas.

In some embodiments, the invention relates to treatment of soft tissue sarcomas. In some embodiments, the invention relates to methods of treating one or more immune-mediated responses and diseases.

For example, in some embodiments, the invention relates to treatment of rejection following transplantation of synthetic or organic grafting materials, cells, organs or tissue to replace all or part of the function of tissues, such as heart, kidney, liver, bone marrow, skin, cornea, vessels, lung, pancreas, intestine, limb, muscle, nerve tissue, duodenum, small-bowel, pancreatic-islet-cell, including xeno-transplants, etc.; treatment of graft-versus-host disease, autoimmune diseases, such as rheumatoid arthritis, systemic lupus erythematosus, thyroiditis, Hashimoto's thyroiditis, multiple sclerosis, myasthenia gravis, type I diabetes uveitis, juvenile-onset or recent-onset diabetes mellitus, uveitis, Graves' disease, psoriasis, atopic dermatitis, Crohn's disease, ulcerative colitis, vasculitis, auto-antibody mediated diseases, aplastic anemia, Evan's syndrome, autoimmune hemolytic anemia, and the like; and further to treatment of infectious-diseases causing aberrant immune response and/or activation, such as traumatic or pathogen induced immune dysregulation, including for example, that which are caused by hepatitis B and C infections, HIV, *Staphylococcus aureus* infection, viral encephalitis, sepsis, parasitic diseases wherein damage is induced by an inflammatory response (e.g., leprosy). In some embodiments, the invention relates to treatment of graft vs host disease (especially with allogenic cells), rheumatoid arthritis, systemic lupus erythematosus, psoriasis, atopic dermatitis, Crohn's disease, ulcerative colitis and/or multiple sclerosis.

Alternatively or additionally, in some embodiments, the invention relates to treatment of an immune response associated with a gene therapy treatment, such as the introduction of foreign genes into autologous cells and expression of the encoded product. In some embodiments, the invention relates to treatment of circulatory diseases, such as arteriosclerosis, atherosclerosis, vasculitis, polyarteritis nodosa and/or myocarditis.

In some embodiments, the invention relates to treatment of any of a variety of neurodegenerative diseases, a non-exhaustive list of which includes:

I. Disorders characterized by progressive dementia in the absence of other prominent neurologic signs, such as Alzheimer's disease; Senile dementia of the Alzheimer type; and Pick's disease (lobar atrophy);

II. Syndromes combining progressive dementia with other prominent neurologic abnormalities such as A) syndromes appearing mainly in adults (e.g., Huntington's disease, Multiple system atrophy combining dementia with ataxia and/or manifestations of Parkinson's disease, Progressive supranuclear palsy (Steel-Richardson-Olszewski), diffuse Lewy body disease, and corticodentatonigral degeneration); and B) syndromes appearing mainly in children or young adults (e.g., Hallervorden-Spatz disease and progressive familial myoclonic epilepsy);

III. Syndromes of gradually developing abnormalities of posture and movement such as paralysis agitans (Parkinson's disease), striatonigral degeneration, progressive supranuclear palsy, torsion dystonia (torsion spasm; dystonia musculorum deformans), spasmodic torticollis and other dyskinesis, familial tremor, and Gilles de la Tourette syndrome;

IV. Syndromes of progressive ataxia such as cerebellar degenerations (e.g., cerebellar cortical degeneration and olivopontocerebellar atrophy (OPCA)); and spinocerebellar degeneration (Friedreich's ataxia and related disorders);

V. Syndromes of central autonomic nervous system failure (Shy-Drager syndrome);

VI. Syndromes of muscular weakness and wasting without sensory changes (motorneuron disease such as amyotrophic lateral sclerosis, spinal muscular atrophy (e.g., infantile spinal muscular atrophy (Werdnig-Hoffman), juvenile spinal muscular atrophy (Wohlfart-Kugelberg-Welander) and other forms of familial spinal muscular atrophy), primary lateral sclerosis, and hereditary spastic paraplegia;

VII. Syndromes combining muscular weakness and wasting with sensory changes (progressive neural muscular atrophy; chronic familial polyneuropathies) such as peroneal muscular atrophy (Charcot-Marie-Tooth), hypertrophic interstitial polyneuropathy (Dejerine-Sottas), and miscellaneous forms of chronic progressive neuropathy;

VIII. Syndromes of progressive visual loss such as pigmentary degeneration of the retina (retinitis pigmentosa), and hereditary optic atrophy (Leber's disease).

In some embodiments, the neurodegenerative disease is Alzheimer's disease, Parkinson's disease, and/or Huntington's disease.

In some embodiments, the invention relates to treatment of disorders, diseases or conditions associated with chromatin remodeling.

The present invention is particularly directed to treatment of tumors expressing the Ras oncogene. As indicated above, Ras-expressing tumors are often more resistant to standard therapies. Ras-expressing tumors are often more resistant to standard therapies. Furthermore, many of the most deadly cancers involve Ras-expressing tumors. For example, 90-95% of pancreatic tumors are Ras-expressing. Similarly, 40-45% of colorectal tumors, 40% of bladder tumors, 15-20% of non small cell lung carcinomas express Ras. Indeed, 10-25% of myelodysplastic syndromes (MDS), which are not themselves cancer but are bone marrow disorders characterized by abnormal cell maturation that typically progress to cancer, also express Ras. There is a profound need for the development of therapies for these and other Ras-expressing diseases and disorders.

DAC Inhibitors

Deacetylase inhibitors, as that term is used herein are compounds which are capable of inhibiting the deacetylation of proteins in vivo, in vitro or both. In many embodiments, the invention relates to HDAC inhibitors, which inhibit the deacetylation of histones. However, those of ordinary skill in the art will appreciate that HDAC inhibitors often have a variety of biological activities, at least some of which may well be independent of histone deacetylase inhibition.

As indicated, DAC inhibitors inhibit the activity of at least one deacetylase. Where the DAC inhibitor is an HDAC inhibitor, an increase in acetylated histones occurs and accumulation of acetylated histones is a suitable biological marker for assessing the activity of HDAC inhibitors. Therefore, procedures which can assay for the accumulation of acetylated histones can be used to determine the HDAC inhibitory activity of agents of interest. Analogous assays can determine DAC inhibitory activity It is understood that agents which can inhibit deacetylase activity (e.g., histone deacetylase activity) typically can also bind to other substrates and as often can inhibit or otherwise regulate other biologically active molecules such as enzymes.

Suitable DAC or HDAC inhibitors according to the present invention include, for example, 1) hydroxamic acid derivatives; 2) Short-Chain Fatty Acids (SCFAs); 3) cyclic tetrapeptides; 4) benzamides; 5) electrophilic ketones; and/or any other class of compounds capable of inhibiting histone deacetylase. Examples of such DAC inhibitors include, but are not limited to:

A) HYDROXAMIC ACID DERIVATIVES such as Suberoylanilide Hydroxamic Acid (SAHA) (Richon et al., *Proc. Natl. Acad. Sci. USA* 95:3003, 1998); M-Carboxycinnamic Acid Bishydroxamide (CBHA) (Richon et al., supra); pyroxamide; CBHA; Trichostatin analogues such as Trichostatin A (TSA) and Trichostatin C (Koghe et al. *Biochem. Pharmacol.* 56:1359, 1998); Salicylihydroxamic Acid (SBHA) (Andrews et al., *International J. Parasitology* 30:761, 2000); Azelaic Bishydroxamic Acid (ABHA) (Andrews et al., supra); Azelaic-1-Hydroxamate-9-Anilide (AAHA) (Qiu et al., *Mol. Biol. Cell* 11:2069, 2000); 6-(3-Chlorophenylureido) carpoic Hydroxamic Acid (3Cl-UCHA), Oxamflatin [(2E)-5-[3-[(phenylsuibnyl-)amino phenyl]-pent-2-en-4-ynohydroxamic acid (Kim et al. *Oncogene*, 18: 2461, 1999); A-161906, Scriptaid (Su et al. 2000 *Cancer Research*, 60:3137, 2000); PXD-101 (Prolifix); LAQ-824; CHAP; MW2796 (Andrews et al., supra); and MW2996 (Andrews et al., supra).

B) CYCLIC TETRAPEPTIDES such as Trapoxin A (TPX)-Cyclic Tetrapeptide (cyclo-(L-phenylalanyl-L-phenylalanyl-D-pipecolinyl-L-2-amino-8-oxo-9,10-epoxy decanoyl)) (Kijima et al., *J. Biol. Chem.* 268:22429, 1993); FR901228 (FK 228, FR901228, Depsipeptide, Romidepsin) (Nakajima et al., *Ex. Cell Res.* 241:12, 1998); FR225497 Cyclic Tetrapeptide (Mori et al., PCT Application WO 00/08048, Feb. 17, 2000); Apicidin Cyclic Tetrapeptide [cyclo(NO-methyl-L-tryptophanyl-L-isoleucinyl-D-pipe-colinyl-L-2-amino-8oxodecanoyl)] (Darkin-Rattray et al., *Proc. Natl. Acad. Sci. USA* 93:13143, 1996); Apicidin Ia, Apicidin Ib, Apicidin Ic, Apicidin IIa, and Apicidin IIb (P. Dulski et al., PCT Application WO 97/11366); CHAP, HC-Toxin Cyclic Tetrapeptide (Bosch et al., *Plant Cell* 7:1941, 1995); WF27082 Cyclic Tetrapeptide (PCT Application WO 98/48825); and Chiamydocin (Bosch et al., supra).

C) SHORT CHAIN FATTY ACID (SCFA) DERIVATIVES such as: Sodium Butyrate (Cousens et al., *J. Biol. Chem.* 254:1716, 1979); Isovalerate (McBain et al., *Biochem. Pharm.* 53:1357, 1997); Valerate (McBain et al., supra); 4 Phenylbutyrate (4-PBA) (Lea and Tulsyan, *Anticancer Research*, 15:879, 1995); Phenylbutyrate (PB) (Wang et al., *Cancer Research*, 59:2766, 1999); Propionate (McBain et al., supra); Butyramide (Lea and Tulsyan, supra); Isobutyramide (Lea and Tulsyan, supra); Phenylacetate (Lea and Tulsyan, supra); 3-Bromopropionate (Lea and Tulsyan, supra); Tributyrin (Guan et al., *Cancer Research*, 60:749, 2000); Valproic acid and Valproate.

Figure 2:
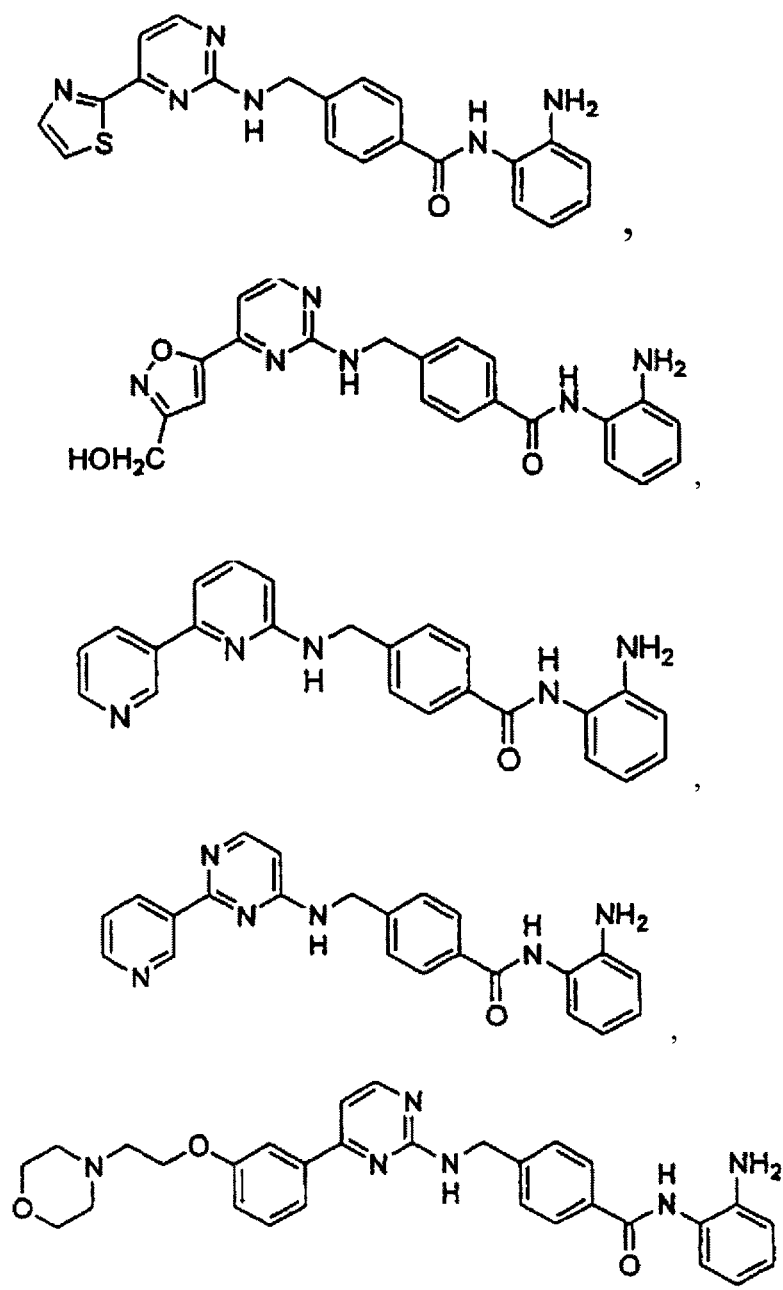

D) BENZAMIDE DERIVATIVES such as CI-994; MS-275 [N-(2-aminophenyl)-4-[N-(pyridin-3-ylmethoxycarbonyl)aminomethyl]benzamide](Saito et al., *Proc. Natl. Acad. Sci. USA* 96:4592, 1999; 3'-amino derivative of MS-27-275 (Saito et al., supra); MGCD0103 (MethylGene; see FIG. 1), or related compounds (for example, see FIG. 2).

E) ELECTROPHILIC KETONE DERIVATIVES such as trifluoromethyl ketones (Frey et al, *Bioorganic & Med. Chem. Lett.*, 12: 3443, 2002; U.S. Pat. No. 6,511,990) and α-keto amides such as N-methyl-α-ketoamides.

Figure 3:
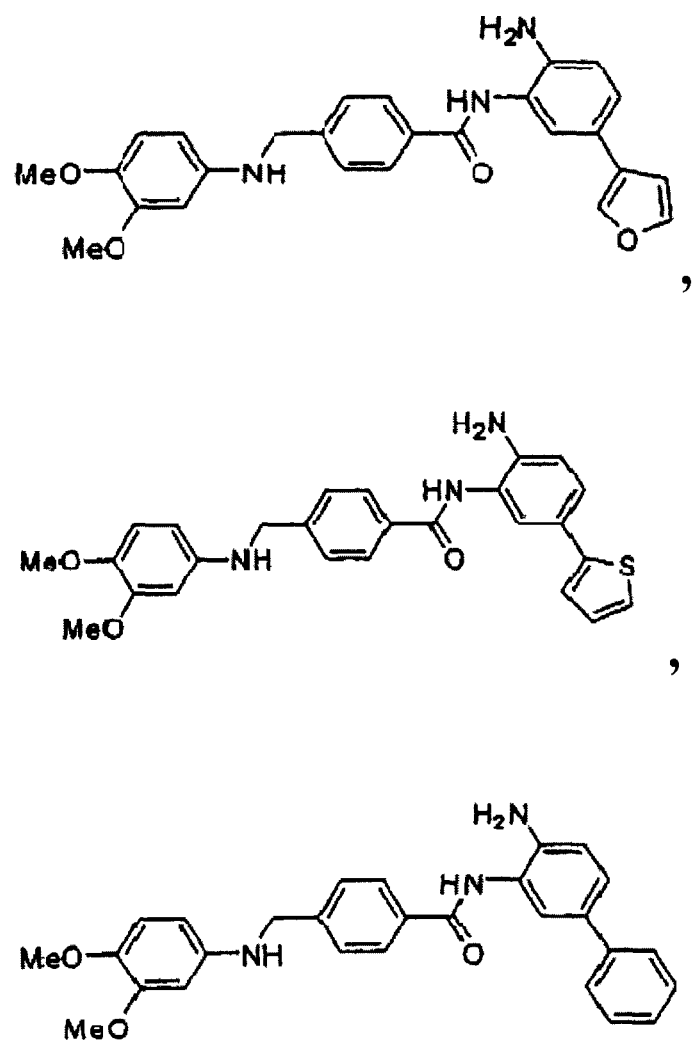

F) OTHER DAC Inhibitors such as Depudecin (Kwon et al., *Proceedings of the National Academy of Sciences USA*, 95:3356, 1998), and compounds depicted in FIG. 3.

Suitable DAC inhibitors for use in accordance with the present invention particularly include, for example, CRA-024781 (Celera Genomics), PXD-101 (CuraGene), LAQ-824 (Novartis AG), LBH-589 (Novartis AG), MGCD0103 (MethylGene), MS-275 (Schering AG), romidepsin (Gloucester Pharmaceuticals), and/or SAHA (Alton Pharma/Merck).

In some embodiments, the DAC or HDAC inhibitor used in the method of the invention is represented by formula (I):

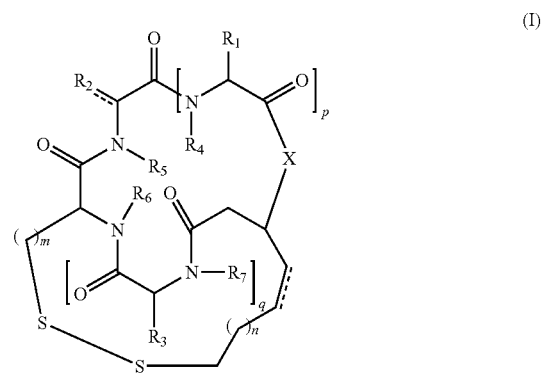

wherein
m is 1, 2, 3 or 4;
n is 0, 1, 2 or 3;
p and q are independently 1 or 2;
X is O, NH, or $NR_8$;
$R_1$, $R_2$, and $R_3$ are independently hydrogen; unsubstituted or substituted, branched or unbranched, cyclic or acyclic aliphatic; unsubstituted or substituted, branched or unbranched, cyclic or acyclic heteroaliphatic; unsubstituted or substituted aryl; or unsubstituted or substituted heteroaryl;
$R_4$, $R_5$, $R_6$, $R_7$ and $R_8$ are independently hydrogen; or substituted or unsubstituted, branched or unbranched, cyclic or acyclic aliphatic; and pharmaceutically acceptable forms thereof. In certain embodiments, m is 1. In certain embodiments, n is 1. In certain embodiments, p is 1. In certain embodiments, q is 1. In certain embodiments, X is O. In certain embodiments, $R_1$, $R_2$, and $R_3$ are unsubstituted, or substituted, branched or unbranched, acyclic aliphatic. In certain embodiments, $R_4$, $R_5$, $R_6$, and $R_7$ are all hydrogen.

In some embodiments, the DAC or HDAC inhibitor used in the method of the invention is represented by formula (II):

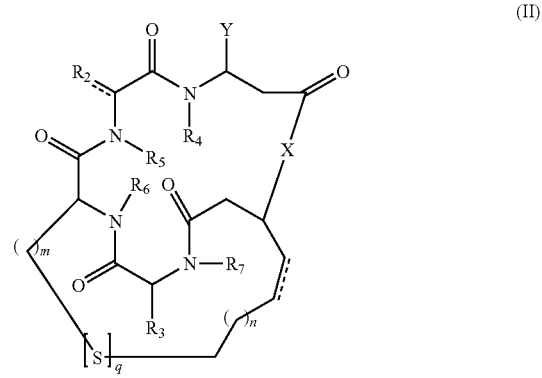

wherein:
  m is 1, 2, 3 or 4;
  n is 0, 1, 2 or 3;
  q is 2 or 3;
  X is O, NH, or $NR_8$;
  Y is $OR_8$, or $SR_8$;
  $R_2$ and $R_3$ are independently hydrogen; unsubstituted or substituted, branched or unbranched, cyclic or acyclic aliphatic; unsubstituted or substituted, branched or unbranched, cyclic or acylic heteroaliphatic; unsubstituted or substituted aryl; or unsubstituted or substituted heteroaryl;
  $R_4$, $R_5$, $R_6$, $R_7$ and $R_8$ are independently selected from hydrogen; or substituted or unsubstituted, branched or unbranched, cyclic or acyclic aliphatic; and pharmaceutically acceptable forms thereof. In certain embodiments, m is 1. In certain embodiments, n is 1. In certain embodiments, q is 2. In certain embodiments, X is O. In other embodiments, X is NH. In certain embodiments, $R_2$ and $R_3$ are unsubstituted or substituted, branched or unbranched, acyclic aliphatic. In certain embodiments, $R_4$, $R_5$, $R_6$, and $R_7$ are all hydrogen.

In some embodiments, the DAC or HDAC inhibitor used in the method of the invention is represented by formula (III):

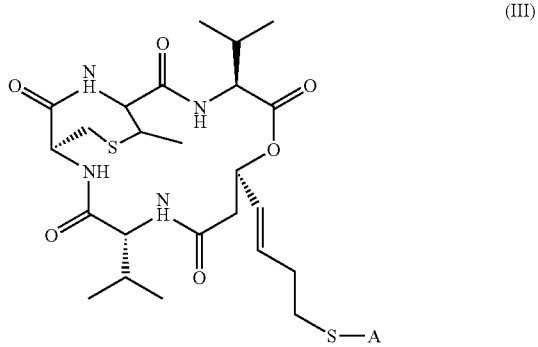

wherein
A is a moiety that is cleaved under physiological conditions to yield a thiol group and includes, for example, an aliphatic or aromatic acyl moiety (to form a thioester bond); an aliphatic or aromatic thioxy (to form a disulfide bond); or the like; and pharmaceutically acceptable forms thereof. Such aliphatic or aromatic groups can include a substituted or unsubstituted, branched or unbranched, cyclic or acyclic aliphatic group; a substituted or unsubstituted aromatic group; a substituted or unsubstituted heteroaromatic group; or a substituted or unsubstituted heterocyclic group. A can be, for example, —$COR_1$, —SC(=O)—O—$R_1$, or —$SR_2$. $R_1$ is independently hydrogen; substituted or unsubstituted amino; substituted or unsubstituted, branched or unbranched, cyclic or acyclic aliphatic; substituted or unsubstituted aromatic group; substituted or unsubstituted heteroaromatic group; or a substituted or unsubstituted heterocyclic group. In certain embodiment, $R_1$ is hydrogen, methyl, ethyl, n-propyl, iso-propyl, n-butyl, isobutyl, benzyl, or bromobenzyl. $R_2$ is a substituted or unsubstituted, branched or unbranched, cyclic or acyclic aliphatic group; a substituted or unsubstituted aromatic group; a substituted or unsubstituted heteroaromatic group; or a substituted or unsubstituted heterocyclic group. In certain embodiments, $R_2$ is methyl, ethyl, 2-hydroxyethyl, isobutyl, fatty acids, a substituted or unsubstituted benzyl, a substituted or unsubstituted aryl, cysteine, homocysteine, or glutathione.

In some embodiments, the DAC or HDAC inhibitor used in the method of the invention is represented by formula (IV) or (IV'):

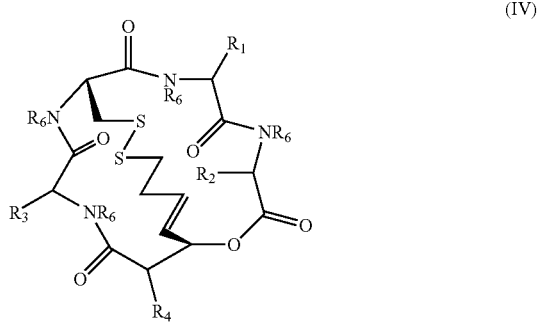

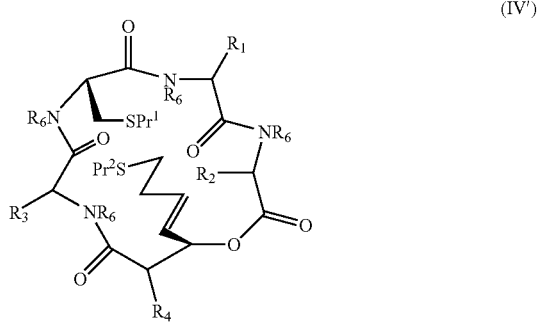

wherein $R_1$, $R_2$, $R_3$, and $R_4$ are the same or different and represent an amino acid side chain moiety, each $R_6$ is the same or different and represents hydrogen or $C_1$-$C_4$ alkyl, and $Pr^1$ and $Pr^2$ are the same or different and represent hydrogen or thiol-protecting group. In certain embodiments, the amino acid side chain moieties are those derived from natural amino acids. In other embodiments, the amino acid side chain moieties are those derived from unnatural amino acids. In certain embodiments, each amino acid side chain is a moiety selected from —H, —$C_1$-$C_6$ alkyl, —$C_2$-$C_6$ alkenyl, -L-O—C(O)—R', -L-C(O)—O—R", -L-A, -L-NR"R", -L-Het-C(O)-Het-R", and -L-Het-R", wherein L is a $C_1$-$C_6$ alkylene group, A is phenyl or a 5- or 6-membered heteroaryl group, each R' is the same or different and represents $C_1$-$C_4$ alkyl, each R" is the same or different and represent H or $C_1$-$C_6$ alkyl, each -Het- is the same or different and is a heteroatom spacer selected from —O—, —N(R''')—, and —S—, and each R''' is the same of different and represents H or $C_1$-$C_4$ alkyl. In certain embodiments, $R_6$ is —H. In certain embodiments, $Pr^1$ and $Pr^2$ are the same or different and are selected from hydrogen and a protecting group selected from a benzyl group which is optionally substituted by $C_1$-$C_6$ alkoxy, $C_1$-$C_6$ acyloxy, hydroxy, nitro, picolyl, picolyl-N-oxide, anthrylmethyl, diphenylmethyl, phenyl, t-butyl, adamanthyl, $C_1$-$C_6$ acyloxymethyl, $C_1$-$C_6$ alkoxymethyl, tetrahydropyranyl, benzylthiomethyl, phenylthiomethyl, thiazolidine, acetamidemethyl, benzamidomethyl, tertiary butoxycarbonyl (BOC), acetyl and its derivatives, benzoyl and its derivatives, carbamoyl, phenylcarbamoyl, and $C_1$-$C_6$ alkylcarbamoyl. In certain embodiments, $Pr^1$ and $Pr^2$ are hydrogen. Various romidepsin derivatives of formula (IV) and (IV') are disclosed in published PCT application WO 2006/129105, published Dec. 7, 2006; which is incorporated herein by reference.

In some embodiments, the DAC or HDAC inhibitor used in the method of the invention is represented by formula (V):

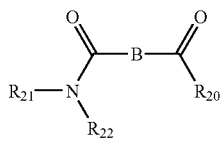 (V)

wherein
B is a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, or a substituted or unsubstituted heterocyclic group; $R_{20}$ is hydroxylamino, hydroxyl, amino, alkylamino, dialkylamino, or alkyloxy group; $R_{21}$ and $R_{22}$ are independently selected from hydrogen, hydroxyl, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, or a substituted or unsubstituted heterocyclic group. In a particular embodiment of Formula IV, $R_{20}$ is a hydroxylamino, hydroxyl, amino, methylamino, dimethylamino or methyloxy group and B is a $C_6$-alkyl. In yet another embodiment of Formula IV, $R_{21}$ is a hydrogen atom, $R_{22}$ is a substituted or unsubstituted phenyl and B is a $C_6$-alkyl. In further embodiments of Formula IV, $R_{21}$ is hydrogen and $R_{22}$ is an α-, β-, or γ-pyridine.

Other examples of DAC or HDAC inhibitors can be found in, for example, U.S. Pat. No. 5,369,108, issued on Nov. 29, 1994, U.S. Pat. No. 5,700,811, issued on Dec. 23, 1997, U.S. Pat. No. 5,773,474, issued on Jun. 30, 1998, U.S. Pat. No. 5,932,616 issued on Aug. 3, 1999 and U.S. Pat. No. 6,511,990, issued Jan. 28, 2003 all to Breslow et al.; U.S. Pat. No. 5,055,608, issued on Oct. 8, 1991, U.S. Pat. No. 5,175,191, issued on Dec. 29, 1992 and U.S. Pat. No. 5,608,108, issued on Mar. 4, 1997 all to Marks et al.; U.S. Provisional Application No. 60/459,826, filed Apr. 1, 2003 in the name of Breslow et al.; as well as, Yoshida, M., et al., Bioassays 17, 423-430 (1995); Saito, A., et al., PNAS USA 96, 4592-4597, (1999); Furamai R. et al., PNAS USA 98 (1), 87-92 (2001); Komatsu, Y., et al., Cancer Res. 61(11), 4459-4466 (2001); Su, G. H., et al., Cancer Res. 60, 3137-3142 (2000); Lee, B. I. et al., Cancer Res. 61(3), 931-934; Suzuki, T., et al., J. Med. Chem. 42(15), 3001-3003 (1999); published PCT Application WO 01/18171 published on Mar. 15, 2001 Sloan-Kettering Institute for Cancer Research and The Trustees of Columbia University; published PCT Application WO02/246144 to Hoffmann-La Roche; published PCT Application WO02/22577 to Novartis; published PCT Application WO02/30879 to Prolifix; published PCT Applications WO 01/38322 (published May 31, 2001), WO 01/70675 (published on Sep. 27, 2001) and WO 00/71703 (published on Nov. 30, 2000) all to Methylgene, Inc.; published PCT Application WO 00/21979 published on Oct. 8, 1999 to Fujisawa Pharmaceutical Co., Ltd.; published PCT Application WO 98/40080 published on Mar. 11, 1998 to Beacon Laboratories, L.L.C.; and Curtin M. (Current patent status of histone deacetylase inhibitors Expert Opin. Ther. Patents (2002) 12(9): 1375-1384 and references cited therein).

Specific non-limiting examples of DAC or HDAC inhibitors are provided in the Table below. It should be noted that the present invention encompasses any compounds which both are structurally similar to the compounds represented below and are capable of inhibiting histone deacetylases.

| Title | |
|---|---|
| MS-275 | 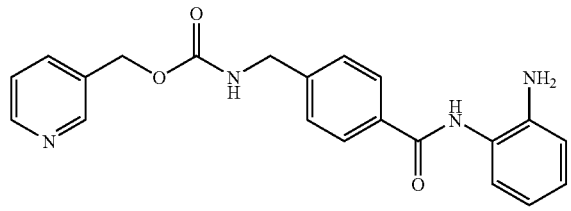 [SMILES: Nc1ccccc1NC(=O)c1ccc(CNC(=O)OCc2cccnc2)cc1] |
| DEPSIPEPTIDE | 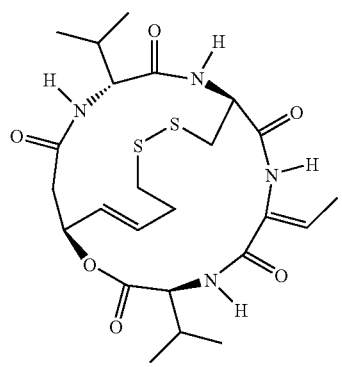 [SMILES: C/C=C1\NC(=O)[C@H]2CSSCC/C=C/[C@H](CC(=O)N[C@H](C(C)C)C(=O)N2)OC(=O)[C@H](C(C)C)NC1=O] |

-continued
| Title | |
|---|---|
| CI-994 | 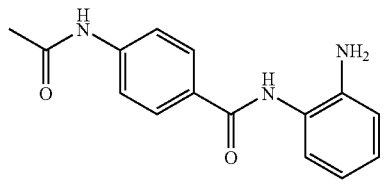 [SMILES: CC(=O)Nc1ccc(C(=O)Nc2ccccc2N)cc1] |
| Apicidin | 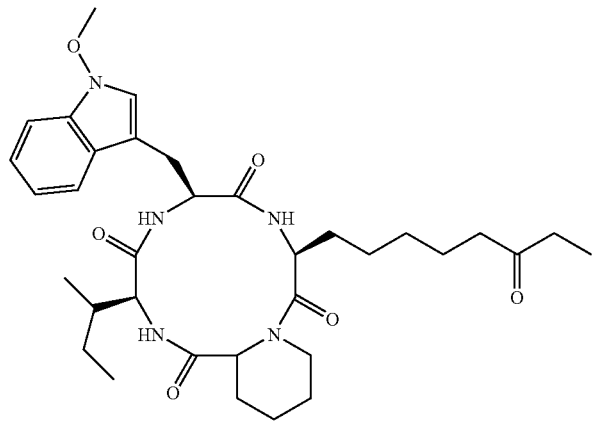 [SMILES: CCC(=O)CCCCC[C@@H]1NC(=O)[C@H](Cc2cn(OC)c3ccccc23)NC(=O)[C@H](C(C)CC)NC(=O)C2CCCCN2C1=O] |
| A-161906 | 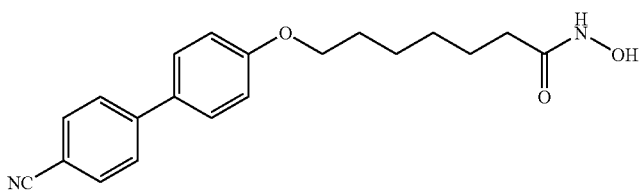 |
| Scriptaid | 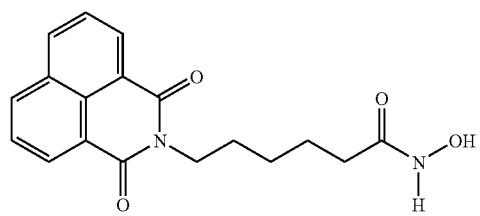 [SMILES: O=C(CCCCCN1C(=O)c2cccc3cccc(c23)C1=O)NO] |
| PXD-001 | 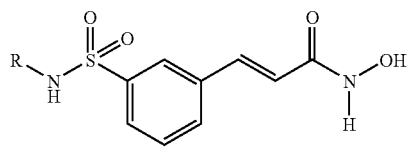 |
| CHAP | 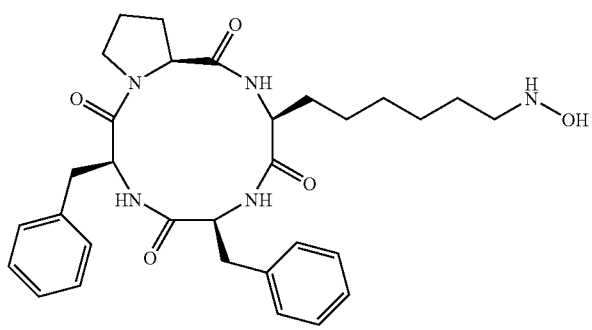 [SMILES: O=C1N[C@@H](Cc2ccccc2)C(=O)N2CCC[C@H]2C(=O)N[C@@H](CCCCCCNO)C(=O)N[C@H]1Cc1ccccc1] |

| Title | |
|---|---|
| LAO-824 | 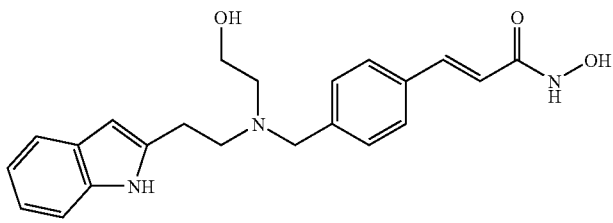 [SMILES: O=C(/C=C/c1ccc(CN(CCO)CCc2cc3ccccc3[nH]2)cc1)NO] |
| Butyric Acid | 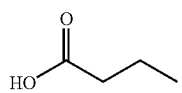 |
| Depudecin | 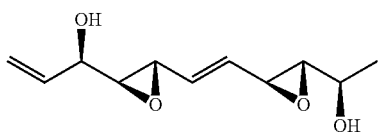 |
| Oxamflatin | 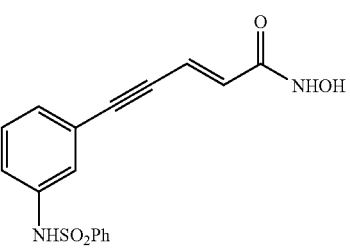 |
| Trichostain C | 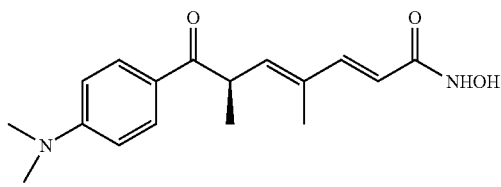 |

DAC or HDAC inhibitors for use in accordance with the present invention may be prepared by any available means including, for example, synthesis, semi-synthesis, or isolation from a natural source.

DAC or HDAC inhibitors for use in accordance with the present invention may be isolated or purified. For example, synthesized compounds can be separated from a reaction mixture, and natural products can be separated from their natural source, by methods such as column chromatography, high pressure liquid chromatography, and/or recrystallization.

A variety of synthetic methodologies for preparing DAC or HDAC inhibitors are known in the art. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

DAC or HDAC inhibitors for use in accordance with the present invention may be modified as compared with presently known DAC or HDAC inhibitors, for example, by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

In some embodiments, a DAC (e.g., HDAC) inhibitor for use in accordance with the present invention may contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention encompasses all such possible isomers, as well as their racemic and optically pure forms to the extent that they have DAC inhibitory activity.

In general, optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981).

In some embodiments, a DAC (e.g., HDAC) inhibitor for use in accordance with the present invention may contain olefinic double bonds, other unsaturation, or other centers of geometric asymmetry. The present invention encompasses both E and Z geometric isomers or cis- and trans-isomers to the extent that they have DAC inhibitory activity. The present invention likewise encompasses all tautomeric forms that have DAC inhibitory activity. In general, where a chemical structure is presented, the configuration of any carbon-carbon double bond appearing herein is selected for convenience only and is not intended to designate a particular configuration unless the text so states or it is otherwise clear from context; thus a carbon-carbon double bond or carbon-heteroatom double bond depicted arbitrarily herein as trans may be cis, trans, or a mixture of the two in any proportion.

DAC inhibitors (e.g., HDAC inhibitors) are particularly useful in the treatment of neoplasms in vivo. However, they may also be used in vitro for research or clinical purposes (e.g., determining the susceptibility of a patient's disease to a particular DAC inhibitor). In certain embodiments, the neoplasm is a benign neoplasm. In other embodiments, the neoplasm is a malignant neoplasm. Any cancer may be treated using a DAC inhibitor alone or in combination with another pharmaceutical agent.

In certain embodiments, the malignancy is a hematological malignancy. Manifestations can include circulating malignant cells as well as malignant masses. Hematological malignancies are types of cancers that affect the blood, bone marrow, and/or lymph nodes. Examples of hematological malignancies that may be treated using romidepsin include, but are not limited to: acute lymphoblastic leukemia (ALL), acute myelogenous leukemia (AML), chronic myelogenous leukemia (CML), chronic lymphocytic leukemia (CLL), hairy cell leukemia, Hodgkin's lymphoma, non-Hodgkin's lymphoma, cutaneous T-cell lymphoma (CTCL), peripheral T-cell lymphoma (PTCL), multiple myeloma, and myelodysplastic syndromes. In certain embodiments, the inventive combination is used to treat multiple myeloma. In certain particular embodiments, the cancer is relapsed and/or refractory multiple myeloma. In other embodiments, the inventive combination is used to treat chromic lymphocytic leukemia (CLL). In certain particular embodiments, the cancer is relapsed and/or refractory CLL. In other embodiments, the inventive combination is used to treat chromic myelogenous leukemia (CML). In certain embodiments, the inventive combination is used to treat acute lymphoblastic leukemia (ALL). In certain embodiments, the inventive combination is used to treat acute myelogenous leukemia (AML). In certain embodiments, the cancer is cutaneous T-cell lymphoma (CTCL). In other embodiments, the cancer is peripheral T-cell lymphoma (PTCL). In certain embodiments, the cancer is a myelodysplastic syndrome.

Other cancers besides hematological malignancies may also be treated using DAC inhibitors. In certain embodiments, the cancer is a solid tumor.

Exemplary cancers that may be treated using DAC inhibitor therapy, including combination therapy, include colon cancer, lung cancer, bone cancer, pancreatic cancer, stomach cancer, esophageal cancer, skin cancer, brain cancer, liver cancer, ovarian cancer, cervical cancer, uterine cancer, testicular cancer, prostate cancer, bladder cancer, kidney cancer, neuroendocrine cancer, etc.

In certain embodiments, a DAC inhibitor is used to treat pancreatic cancer. In certain embodiments, a DAC inhibitor is used to treat prostate cancer. In certain specific embodiments, the prostate cancer is hormone refractory prostate cancer.

Combination Therapy

DAC inhibitors in accordance with the present invention may be administered in combination with one or more other therapeutic agents to treat a disease or disorder associated with Ras expression, or to treat one or more symptoms of such a disease or disorder. To give one specific example, the present invention demonstrates the particular utility of administering a combination of a DAC inhibitor and gemcitabine. In some particular embodiments of the present invention, the DAC inhibitor is romidepsin (aka depsipeptide, FK228, FR901228). In some particular embodiments, the DAC inhibitor is SAHA. In some particular embodiments, the DAC inhibitor is phenylbutyrate. In some particular embodiments, the DAC inhibitor comprises a combination of DAC inhibitors.

Useful agents that can be administered in combination with DAC inhibitors (e.g., romidespin) include, for example, other chemotherapeutic agents, pain relievers, antipsychotics, anti-inflammatories, anti-infectives, hormones, immnuomodulators, hematopoietic agents, anticoagulants, steroids, thrombolytics, antiplatelet drugs, drugs that affect gastrointestinal function, diuretics, antihypertensives, antiarrhythmials, or other drugs affecting renal and/or cardiovascular function, etc. Alternatively or additionally, DAC inhibitors may be administered in combination with vitamins, electrolytes; etc.

In certain embodiments, a DAC inhibitor is administered in combination with one or more additional therapeutic agents, e.g., another cytotoxic agent. Exemplary cytotoxic agents that may be administered in combination with a DAC inhibitor include gemcitabine, decitabine, and flavopiridol.

In other embodiments, a DAC inhibitor is administered in combination with an anti-inflammatory agent such as aspirin, ibuprofen, acetaminophen, etc., pain reliever, anti-nausea medication, or anti-pyretic.

In certain other embodiments, a DAC inhibitor is administered in combination with a steroidal agent (e.g., dexamethasone).

In certain embodiments, a DAC inhibitor is administered in combination with an agent to treat gastrointestinal disturbances such as nausea, vomiting, and diarrhea. These additional agents may include anti-emetics, anti-diarrheals, fluid replacement, electrolyte replacement, etc.

In other embodiments, a DAC inhibitor is administered in combination with electrolyte replacement or supplementation such as potassium, magnesium, and calcium, in particular, potassium and magnesium.

In certain embodiments, a DAC inhibitor is administered in combination an anti-arrhythmic agent.

In certain embodiments, a DAC inhibitor is administered in combination with a platelet booster, for example, an agent that increases the production of platelets.

In certain embodiments, a DAC inhibitor is administered in combination with an agent to boost the production of blood cells such as erythropoietin.

In certain embodiments, a DAC inhibitor is administered in combination with an agent to prevent hyperglycemia.

In certain embodiments, a DAC inhibitor is not administered with another HDAC or DAC inhibitor.

As will be appreciated by those of skill in the art, and as is otherwise addressed herein, either or both of the DAC inhibitor and other agent may be provided in any useful form including, for example, as a salt, ester, active metabolite, prodrug, etc. Similarly, either or both agents (or salts, esters, or prodrugs thereof) may be provided as a pure isomer stereoisomer or as a combination of stereoisomers, including a racemic combination, so long as relevant activity is present. Comparably, either or both agents (or salts, esters or prodrugs thereof) may be provided in crystalline form, whether a pure polymorph or a combination of polymorphs, or in amorphous form, so long as relevant activity is present.

As addressed above, combination therapy of DAC inhibitors and other agent(s) will typically involve administration of multiple individual doses spaced out in time. In some embodiments, individual DAC inhibitor doses and other agent doses will be administered together, according to the same schedule. In other embodiments, DAC inhibitor doses and other agent doses will be administered according to different schedules.

The total daily dose of any particular active agent administered to a human or other animal in single or in divided doses in accordance with the present invention can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses. In certain embodiments, about 10-100 mg of the compound is administered per day in single or multiple doses. In certain embodiments, about 100-500 mg of the compound is administered per day in single or multiple doses. In certain embodiments, about 250-500 mg of the compound is administered per day in single or multiple doses. In certain embodiments, about 500-750 mg of the compound is administered per day in single or multiple doses.

In the treatment of neoplasms such as cancer in a subject, a DAC inhibitor is typically dosed at 1-30 mg/m$^2$. In certain embodiments, a DAC inhibitor is dosed at 1-15 mg/m$^2$. In certain embodiments, a DAC inhibitor is dosed at 5-15 mg/m$^2$. In certain particular embodiments, a DAC inhibitor is dosed at 4, 6, 8, 10, 12, 14, 16, 18, or 20 mg/m$^2$. A DAC inhibitor is typically administered in a 28 day cycle with the agent being administered on days 1, 8 and 15. In certain embodiments, the DAC is administered on days 1 and 15 with day 8 being skipped. As would be appreciated by one of skill in the art, the dosage and timing of administration of the dosage of the DAC inhibitor may vary depending on the patient and condition being treated. For example, adverse side effects may call for lowering the dosage of DAC inhibitor administered.

Typical dosing schedules have been established for certain exemplary DAC inhibitors (e.g., HDAC inhibitors). For example, SAHA is commonly administered within a range of about 300-400 mg daily orally; PXD101 is commonly administered within a range of about up to 2000 mg/m$^2$/day intravenously (e.g., on days 1 to 5 of a 21 day cycle), and may possibly be administered orally; MGCD0103 is commonly administered at doses up to about 27 mg/m$^2$ given orally (e.g., daily for about 14 days); LBH589 is commonly administered at doses up to about 14 mg/m$^2$ as an intravenous infusion (e.g., on days 1-7 of a 21 day cycle); MS-275 is commonly administered within a dose range of about 2-12 mg/m$^2$ intravenously (e.g., every 14 days).

In the treatment of neoplasms such as cancer in a subject, romidepsin is typically dosed at 1-28 mg/m$^2$. In certain embodiments, romidepsin is dosed at 1-15 mg/m$^2$. In certain embodiments, romidepsin is dosed at 5-14 mg/m$^2$. In certain particular embodiments, romidepsin is dosed at 8, 10, 12, or 14 mg/m$^2$. Romidepsin is typically administered in a 28 day cycle with romidepsin being administered on days 1, 8 and 15. In certain embodiments, romidepsin is administered on days 1 and with day 8 being skipped.

As would be appreciated by one of skill in the art, the dosage and timing of administration of any particular DAC inhibitor or other agent dose, or the dosage amount and schedule generally may vary depending on the patient and condition being treated. For example, adverse side effects may call for lowering the dosage of one or the other agent, or of both agents, being administered.

Moreover, those of ordinary skill in the art will readily appreciate that the dosage schedule (i.e., amount and timing of individual doses) by which any particular DAC inhibitor is administered may be different for inventive combination therapy than it is alone.

To give but one example, in some embodiments, a DAC inhibitor (e.g., romidepsin) and other agent are each dosed on days 1 and 15 of a 28 day cycle. Those of ordinary skill in the art will appreciate that any of a variety of other dosing regimens are within the scope of the invention. Commonly, dosing is adjusted based on a patient's response to therapy, and particularly to development of side effects.

In some embodiments of the present invention, a DAC inhibitor is administered in combination with gemcitabine, for example as is described in co-pending U.S. Provisional patent application Ser. No. 12/298,265 entitled "GEMCITABINE COMBINATION THERAPY", filed on even date herewith and attached hereto in its entirety as Exhibit A.

Pharmaceutical Compositions

DAC inhibitors and/or other agents for use in accordance with the present invention are often administered as pharmaceutical compositions comprising amounts of DAC inhibitor and/or other agent that are useful in inventive therapy. In some embodiments, a DAC inhibitor and another agent are present together in a single pharmaceutical composition; in some embodiments these agents are provided in separate pharmaceutical compositions.

In some embodiments, inventive pharmaceutical compositions are prepared in unit dosage forms. In general, a pharmaceutical composition of the present invention includes one or more active agents (i.e., one or more DAC inhibitors, such as romidepsin) formulated with one or more pharmaceutically acceptable carriers or excipients.

In some embodiments, the pharmaceutically acceptable carrier is selected from the group consisting of sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions; non-toxic compatible lubricants such as sodium lauryl sulfate and magnesium stearate; coloring agents; releasing agents; coating agents; sweetening, flavoring and perfuming agents; preservatives and antioxidants; and combinations thereof. In some embodiments, the pH of the ultimate pharmaceutical formulation may be adjusted with pharmaceutically acceptable acids, bases or buffers to enhance the stability of the formulated compound or its delivery form.

Pharmaceutical compositions of this invention may be administered can be administered by any appropriate means including, for example, orally, parenterally, by inhalation spray, topically, rectally, nasally, buccally, vaginally or via an implanted reservoir. The term parenteral as used herein includes subcutaneous, intracutaneous, intravenous, intramuscular, intraarticular, intraarterial, intrasynovial, intrasternal, intrathecal, intralesional and intracranial injection or infusion techniques. In many embodiments, pharmaceutical compositions are administered orally or by injection in accordance with the present invention.

Liquid dosage forms for oral administration include pharmaceutically acceptable emulsions, microemulsions, solutions, suspensions, syrups and elixirs. In addition to the active agent(s), liquid dosage forms of pharmaceutical compositions may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. A sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from a site of subcutaneous or intramuscular injection. This may be accomplished by the use of a liquid suspension of crystalline or amorphous material with poor water-solubility. The rate of absorption of the drug then depends upon its rate of dissolution, which, in turn, may depend upon crystal size and crystalline form.

Alternatively, delayed absorption of a parenterally administered drug form can be accomplished by dissolving or suspending the drug in an oil vehicle. Injectable depot forms can be made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations can also be prepared by entrapping the drug in liposomes or microemulsions that are compatible with body tissues.

Compositions for rectal or vaginal administration are typically suppositories which can be prepared by mixing the active agents with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include, for example, capsules, tablets, pills, powders, and granules. In such solid dosage forms, the active agent(s) is/are typically mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents, permeation enhancers, and/or other agents to enhance absorption of the active agent(s).

Solid compositions of a similar type may also be employed as fillers in soft and hard-filled gelatin capsules using such excipients as lactose or milk sugar as well as high molecular weight polyethylene glycols and the like.

Solid dosage forms such as tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

In certain embodiments, oral dosage forms are prepared with coatings or by other means to control release of active agent (e.g., DAC inhibitor and/or gemcitabine) over time and/or location within the gastrointestinal tract. A variety of strategies to achieve such controlled (or extended) release are well known in the art, and are within the scope of the present invention.

Dosage forms for topical or transdermal administration include ointments, pastes, creams, lotions, gels, powders, solutions, sprays, inhalants or patches. In general, such preparations are prepared by admixing active agent(s) under sterile conditions with a pharmaceutically acceptable carrier and any needed preservatives or buffers as may be required.

Ophthalmic formulation, ear drops, eye ointments, powders and solutions are also contemplated as being within the scope of this invention.

Ointments, pastes, creams and gels may contain, in addition to active agent(s), excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to active agent(s), excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have often can provide controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, active agent(s) is/are formulated and administered to the patient in solid or liquid particulate form by direct administration e.g., inhalation into the respiratory system. Solid or liquid particulate forms of the active agent(s) prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43,650 by Montgomery, all of which are incorporated herein by reference). A discussion of pulmonary delivery of antibiotics is also found in U.S. Pat. No. 6,014,969, incorporated herein by reference.

Pharmaceutical compositions for use in accordance with the present invention can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, for example with a dosage ranging from about 0.1 to about 500 mg/kg of body weight, alternatively dosages between 1 mg and 1000 mg/dose, every 4 to 120 hours, or according to the requirements of the particular drug.

The methods herein contemplate administration of an effective amount of active agent or pharmaceutical composition sufficient for a desired or stated effect. Typically, the pharmaceutical compositions of this invention will be administered from about 1 to about 6 times per day or alternatively, as a continuous infusion. Such administration can be used as a chronic or acute therapy.

The amount of any particular active agent that may be combined with pharmaceutically acceptable excipients or carriers to produce a single dosage form may vary depending upon the host treated and the particular mode of administration. A typical preparation will contain from about 5% to about 95% active compound (w/w). Alternatively, such preparations may contain from about 20% to about 80% active compound. For romidepsin, preparations may commonly contain about 20-50%, 25-45%, 30-40%, or approximately 32%, 33%, 34%, or 35% active compound; for gemcitabine, the compound is typically provided in 200 mg or 1 gram vials as a lyophilized powder. Drug product is reconstituted with either 5 ml (for the 200 mg vial) or 25 ml (for the 1 g vial) using sodium chloride for injection. Both dilutions give a 38 mg/ml solution (including displacement volume). This solution can be diluted down to 0.1 mg/ml-0.4 mg/ml for administration.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

When pharmaceutical compositions contain two or more active agents, it is generally the case that each agent is present at dosage levels of between about 1 to 100%, for example about 5 to 95%, of the level normally administered in a monotherapy regimen.

Unless otherwise defined, all technical and scientific terms used herein are accorded the meaning commonly known to one of ordinary skill in the art. All publications, patents, published patent applications, and other references mentioned herein are hereby incorporated by reference in their entirety. The embodiments of the invention should not be deemed to be mutually exclusive and can be combined.

Unless otherwise defined, all technical and scientific terms used herein are accorded the meaning commonly known to one of ordinary skill in the art. All publications, patents, published patent applications, and other references mentioned herein are hereby incorporated by reference in their entirety. The embodiments of the invention should not be deemed to be mutually exclusive and can be combined.

EXEMPLIFICATION

The present invention will be better understood in connection with the following Examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Depsipeptide (FK228) Alone and in Combination with Gemcitabine in In Vivo Mouse Xenograft Model of Ras-Expressing Pancreatic Tumor The present Example demonstrates that both depsipeptide (FK228; romidepsin) and gemcitabine can effectively inhibit tumor growth in a mouse xenograft model, and further demonstrates a surprising synergistic effect of the combination.

Figure 4:
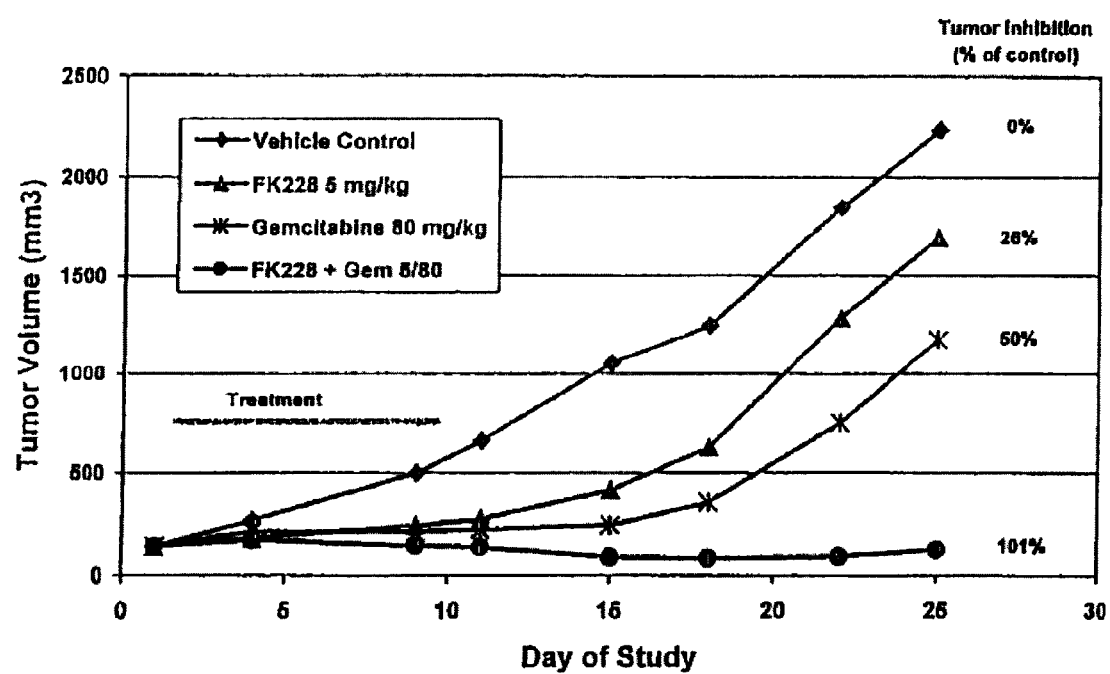
FIG. 4 shows the effects of depsipeptide (FK228) alone and in combination with gemcitabine in in vivo mouse xenograft model of Ras-expressing pancreatic tumor.

Panc-1, obtained from the ATCC, is a pancreas tumor cell line (oncogenic K-ras) originating from a 56 year old Caucasian male. In this study, female nude mice were implanted subcutaneously (SC) by trocar with Panc-1 tumor fragments harvested from SC growing tumors in nude mice hosts. When tumors reaches approximately 140 mm$^3$, animals were pair matched by tumor size into treatment and control groups (N=9 mice per group) (FIG. 4). The day of treatment initiation was specified as Day 1. Vehicle control and FK228 were administered intravenously on a Q4Dx3 schedule (Days 1, 5, and 9). Gemcitabine was administered by an intraperitoneal injection on a Q3Dx4 schedule (Days 1, 4, 7, 10). Tumors were measured by Vernier calipers twice weekly.

Treatment with depsipeptide (FK228, FR901228, romidepsin) and gemcitabine as single agents both resulted in consistently smaller tumors than vehicle control treated animals, with tumor growth inhibitions of 26% and 50%, respectively.

In addition, a potential synergistic effect of depsipeptide and gemcitabine was observed in combination with a significant tumor growth inhibition of 101%. Three animals in the combination group exhibited evidence of tumor regression. These results indicate depsipeptide has clear antitumor activity against the Panc-1 human pancreas tumors in an in vivo xenograft model. Furthermore, depsipeptide has the potential to synergize with other approved chemotherapeutics, and specifically with gemcitabine. The effects of this synergy, including tumor regression, are particularly significant given the known aggressiveness of pancreatic tumors, and their susceptibility to developing resistance. The present invention demonstrates tumor regression after dosing with a combination of romidepsin and gemcitabine. Note that no regression was observed with gemcitabine alone, the current standard therapy for pancreatic tumors, yet regression was observed with the combination.

We note that no synergistic effect was observed with the combination of romidepsin and gemcitabine in another cell line (Bx-PC-3) that had normal Ras (See Example 3, below).

Example 2

Combination of FK228 and Gemcitabine is More Effective than Either Agent Alone in a Ras-Transformed Pancreatic Adenocarcinoma Model The present Example demonstrates that the combination of FK228 and gemcitabine is more effective than either agent alone in a pancreatic adenocarcinoma model.

Abstract: To examine activity and mechanism of FK228, antitumor efficacy was tested in PANC-1 pancreatic adenocarcinoma model representing transformed Ras, either as a single agent or in combination with gemcitabine. Following PANC-1 study completion, tumor and sera were obtained from:
  the vehicle control;
  FK228 dosed at 5 mg/kg once every four days for three treatments (Q4Dx3);
  Gemcitabine at 80 mg/kg (Q3Dx4); and
  the drug combination.
Expression of c-Myc, acetylated histones 3 and 4, and $p21^{waf}1$ was compared between control and FK228 groups by immunoblotting and was quantified following actin normalization. Serum levels of putative tumor products b-FGF and MMP-2 were quantified by human-specific ELISA.

Highly significant (p<0.0001) downregulation of c-Myc was observed in all treatment groups, most dramatically in the combination group. Acetylated histone 3 levels were not affected in FK228 alone or in combination with gemcitabine. Upregulation of acetylated histone 4 by the drug combination was highly significant. Treatment with gemcitabine alone significantly (p<0.05) downregulated $p21^{waf}$; however, this effect was not reported in combination groups.

These results suggest activity of FK228 is Ras-transformed malignancies and demonstrate combinatorial effects with gemcitabine at least in pancreatic adenocarcinoma. Surprising long-term effects of FK228 in combination with gemcitabine on c-Myc and acetylated histone 4 might suggest tumor phenotypic changes consistent with downregulation of HDAC activity.

Materials and Methods

Specimen Collection: FK228 antitumor efficacy was tested in PANC-1 pancreatic adenocarcinoma model representing transformed Ras, either as a single agent or in combination with gemcitabine. Tumor xenograft tissue and serum specimens were obtained from in vivo studies performed by the Preclinical Research Laboratory at the completion of the experiments. The following tumor and sera specimens were obtained:
  Vehicle control (n-9)
  FK228 at 5 mg/kg once every four days for three treatments (Q4Dx3) (n=9)
  Gemcitabine at 80 mg/kg (Q3Dx4) (n=9)
  FK228 at 5 mg/kg plus gemcitabine at 80 mg/kg (Q3Dx4) (n=6)
Tumors were dissected from the animals, rinsed in cold phosphate buffered saline, and snap frozen in liquid nitrogen. Serum was obtained from whole blood and stored frozen at −70° C.

Tissue Biomarkers: Tumor levels of acetylated histone-4, histone-4, c-Myc, p21waf and β-actin were quantified by immunoblotting as described. Briefly, frozen tissue was pulverized under liquid nitrogen and homogenized in hypotonic lysis buffer. Small aliquots of the extracts were used for analysis of protein concentration by micro-BCA assay with bovine serum albumin as a protein standard. An equal amount of extracts containing about 20-50 μg protein was electrophoresed in SDS polyacrylamide gels. Proteins were transferred to ImmunoBlot PVDF membrane and were probed with appropriate primary and secondary antibodies. The chemiluminescence signal was captured by autoradiography, quantified by densitometry and expressed as a ratio of actin in each sample lane. For each biomarker, means and standard errors were calculated in each treatment group. The data were analyzed by two-sided t-tests to determine if measured end points are significantly affected by drug treatment.

Serum Biomarkers: Serum levels of b-FGF and VEGF were quantified by ELISA using human-specific kits from R&D Systems, Minneapolis, Minn., according to supplier's instructions. All assays were performed in duplicate. For each biomarker, means and standard errors were calculated in each treatment group. The data were analyzed by two-sided t-tests to determine if measured endpoints are significantly affected by drug treatment.

Results

The results of western blot detection of acetylated histone 3, histone 4, c-Myc, $p21^{waf}$ and a housekeeping gene product β-actin as an internal control are shown in FIG. 4. Uniform expression of β-actin was noted in all samples. Following quantitative analysis of biomarker levels in each sample, the results were normalized for b-actin and expressed as percentages of untreated controls. Group averages were compared by t-test.

When compared with the controls, the expression of c-Myc was inhibited in all groups. The extent of inhibition (50%) was similar in the gemcitabine and FK228 monotherapy treatment groups and greater (60%) in the combination group. The inhibition of c-Myc expression was highly significant (p<0.0001) in all cases.

Acetylation of histone 3 was significantly inhibited by gemcitabine, but not affected by FK228 alone or in combination with gemcitabine.

The levels of acetylated histone 4 were on the control level in the gemcitabine group. FK228 treatment induced over 2-fold increase of acetylated histone 4, but in comparison with the control group the increase was not significant. On the other hand, over 3-fold up-regulation of acetylated histone 4 by the drug combination was highly significant (p=0.00003).

Treatment with gemcitabine alone significantly (p<0.05) down-regulated $p21^{waf}$; however, this effect was not observed in the combination groups.

Quantitative analysis of b-FGF and VEGF in serum was performed. The levels of b-FGF were highly variable but not significantly different in any treatment groups in comparison with the controls. VEGF was under the detection limits of the assay.

The effects of FK228 on expression of c-Myc and acetylated histone 4 are unexpected considering that these endpoints were assessed at the end of a long-term in vivo treatment with the drug. Historically, the effects of DAC inhibitors such as FK228 on target gene or protein expression were assessed in a time scale of hours (not days) following drug treatment. For example, a study on the effects of FK228 on tumor growth and expression of p21 and c-myc genes in vivo over a period of 2 to 24 hours demonstrated induction of p21 mRNA and decreased c-myc mRNA in tumor xenograft sensitive to FK228, while opposite effects on p21 and c-myc mRNA were seen in tumor xenograft less sensitive to FK228.

Myc genes are key regulators of cell proliferation, and their deregulation contributes to the genesis of most human tumors. Transcriptional regulation by Myc-family proteins includes recruitment of HDACs in tumors, some of which exhibit dependence (addition) to c-myc. Even a brief inhibition of c-myc expression may be sufficient to completely stop tumor growth and induce regression of tumors. It is conceivable that biological activity of FK228 could be partly due to inhibition of c-myc and other genes under its control, including HDACs.

In conclusion, these results demonstrate at least additive combinatorial effects with gemcitabine on the expression of c-Myc and acetylation of histone 4 in pancreatic adenocarcinoma. Surprising effects of FK228 in combination with gemcitabine might suggest tumor phenotypic changes consistent with downregulation of HDAC activity. Specifically, weeks after the end of treatment, the cells are phenotypically, different from those that were initially injected, suggesting some form of cellular transformation, possible to a less aggressive phenotype.

Example 3

Depsipeptide (FK228) Alone and in Combination with Gemcitabine in In Vivo Mouse Xenograft Model of Ras-Expressing Pancreatic Tumor As Compared with Non-Ras-Expressing Tumor The present Example demonstrates a specific effect of depsipeptide and gemcitabine on Ras-expressing tumors (PANC-1) as compared with non-Ras-expressing tumors (BxPC03):

Materials and Methods

Model Information—Female nude mice (nu/nu) between 5 and 6 weeks of age weighing approximately 20 grams were obtained from Harlan, Inc. (Madison, Wis.). PANC-1, obtained from the ATCC, is a pancreas tumor cell line originating from a 56 year-old Caucasian male[1-2]. BxPC-3, obtained from the American Type Culture Collection (ATCC), is a pancreas tumor cell line originating from a 61 year-old female[3-4]. PANC-1 Study: Animals were implanted subcutaneously (SC) by trocar with fragments of PANC-1 harvested from SC growing tumors in nude mice hosts. When tumors grew to approximately 135 cubic millimeters ($mm^3$) in size (17 days following implantation, animals were pair-matched by tumor size into treatment and control groups; each treatment group contained nine mice. BxPC-3 Study: Animals were implanted subcutaneously (SC) by trocar with fragments of BxPC-3 harvested from SC growing tumors in nude mice hosts. When tumors grew to approximately 85 cubic millimeters ($mm^3$) in size (19 days following implantation), animals were pair-matched by tumor size into treatment and control groups; each treatment group contained nine mice. Animals in both studies were ear-tagged and followed individually throughout the experiment.

Study Design and Dosing—Initial doses were administered on Day 1 following pair-matching; both experiments were carried out as tumor growth inhibition (TGI) studies. Animals were dosed intravenously (IV) via tail vein with FK228 once every four days for three treatments (Q4Dx3) or by intraperitoneal (IP) injection with gemcitabine once every three days for four treatments (Q3Dx4), either alone or in combination, at the doses listed below (Table 1). To serve as a negative control, FK228 vehicle (2% ethanol, 8% propylene glycol, 90% 0.9% saline) was injected on a Q4Dx3 schedule.

TABLE 1

Study Design (PANC-1 and BxPC-3 Xenograft Studies)

| Group | # Animals | Compound | Dose (mg/kg) | Route/Schedule |
|---|---|---|---|---|
| 1 | 8-9 | Vehicle | — | IV; Q4Dx3 |
| 2 | 8-9 | FK228 | 2.5 | IV; Q4Dx3 |
| 3 | 8-9 | FK228 | 5 | IV; Q4Dx3 |
| 4 | 8-9 | Gemcitabine | 40 | IP; Q3Dx4 |
| 5 | 8-9 | Gemcitabine | 80 | IP; Q3Dx4 |
|   |     | FK228 | 2.5 | IV; Q4Dx3 |
| 6 | 8-9 | Gemcitabine | 40 | IV; Q4Dx3 |
|   |     | FK228 | 5 | IV; Q4Dx3 |
| 7 | 8-9 | Gemcitabine | 40 | IP; Q3Dx4 |
|   |     | FK228 | 2.5 | IV; Q4Dx3 |
| 8 | 8-9 | Gemcitabine | 80 | IP; Q3Dx4 |
|   |     | FK228 | 5 | IV; Q4Dx3 |
| 9 | 8-9 | Gemcitabine | 80 | IP; Q3Dx4 |

Data Collection and Statistical Analysis

Animal Weights—Individual and group mean weights±SD and percent weight change through Day 25 (PANC-1) or Day 29 (BxPC-3) were recorded twice weekly until study completion beginning Day 1. Final group mean weights±SD and group nadir values are reported; weight data from individual animals experiencing technical or drug-related deaths was censored from final group calculations.

Moribundity/Mortality—Animals were observed twice weekly for general moribundity and daily for mortality. Animal deaths were assessed as drug-related or technical based on factors including gross observation and weight loss; reported animal death information includes type, number, and day of death for each group.

Tumor Volume—Individual and group mean tumor volumes±SEM through Day 25 (PANC-1) or Day 29 (BxPC-3) were recorded twice weekly until study completion beginning Day 1 (Appendix II). Tumor measurements were converted to cubic millimeter tumor volume using the formula[5]:

$$\text{Tumor Volume (mm}^3) = \text{Width}^2 \text{(mm)} \times \text{Length (mm)} \times 0.52$$

Final mean tumor volume±SEM for each group was reported; animals experiencing partial or complete tumor regressions or animals experiencing technical or drug-related deaths were censored from these calculations.

Tumor Growth Inhibition—On Day 25 (PANC-1) or Day 29 (BxPC-3), mice were weighed and caliper tumor measurements taken. Tumor growth inhibition (TGI) values were calculated for each group containing treated animals using the formula[6]:

$$1 - \frac{\text{Mean Final Tumor Volume(Treated)} - \text{Mean Initial Tumor Volume(Treated)}}{\text{Mean Final Tumor Volume(Control)} - \text{Mean Initial Tumor Volume(Control)}} \times 100\%$$

Animals experiencing partial or complete tumor regressions or animals experiencing technical or drug-related deaths were censored from TGI calculations; the National Cancer Institute (NCI) criteria for compound activity is TGI>58%[7]. TGI values for each treatment group are reported at study completion; these calculations are based on the final study day.

Partial/Complete Tumor Response—Individual mice possessing tumors measuring less than on Day 1 were classified as having partial regression (PR) and a tumor regression value is determined using the formula[6]:

$$1 - \frac{\text{Final Tumor Volume(mm}^3)}{\text{Final Tumor Volume(mm}^3)} \times 100\%$$

If partial tumor regression was reported in multiple animals within one group, a mean value was determined. Individual mice lacking palpable tumors were classified as undergoing complete regression (CR). Animals experiencing partial or complete tumor regressions were censored from TGI calculations. However, data from these animals was included in statistical analysis calculations. In addition, weight data from these animals was included in daily and final group calculations.

Tumor Necrosis—Degree of tumor necrosis was rated at each tumor measurement using the following arbitrary index:

| | | |
|---|---|---|
| N0 | None | No Visible Necrosis |
| N1 | Slight | Reddened or Inflamed; Intact Tumor |
| N2 | Mild | <10% Tumor Necrosis |
| N3 | Moderate | <50% Tumor Necrosis |
| N4 | Severe | >50% Tumor Necrosis |

Notable differences in tumor necrosis between treated and control groups are reported.

Statistics—Statistical analyses were carried out between treated and control groups comparing final weight, percent weight change, and tumor growth inhibition (Appendix III). For these groups, a two-tailed One-Way Analysis of Variance (ANOVA) followed by the Dunnett multiple comparisons test was employed. All analyses are performed using GraphPad Prism® software (version 4.0). Weight and tumor data from individual animals experiencing technical or drug-related deaths was censored from analysis. However, weight and tumor data from animals reporting partial or complete regressions was included in these calculations.

PANC-1 Study Results

TABLE 2

Animal Weight and Drug Toxicity Results: PANC-1 Control and Single Agent Groups (Day 25)

| GROUP | DOSE | ROUTE/ SCHEDULE | FINAL WEIGHT DATA (DAY 25) MEAN (G) ± SD | % CHANGE | WEIGHT NADIR % CHANGE | WEIGHT NADIR DAY | DRUG DEATHS TOTAL | DRUG DEATHS DAY (#) |
|---|---|---|---|---|---|---|---|---|
| Vehicle | — | IV/Q4Dx3 | 24 ± 3 | +8 | — | — | 0 | — |
| Gemcitabine | 40 mg/kg | IP/Q3Dx4 | 24 ± 1 | +7 | −2 | 11 | 0 | — |
| Gemcitabine | 80 mg/kg | IP/Q3Dx4 | 26 ± 3 | +12 | −3 | 11 | 0 | — |
| FK228 | 2.5 mg/kg | IV/Q4Dx3 | 23 ± 2 | +8 | −9 | 11 | 0 | — |
| FK228 | 5 mg/kg | IV/Q4Dx3 | 25 ± 2 | +9 | −12 | 11 | 0 | — |

N = 9/GRP ON DAY 1

TABLE 3

Tumor Volume and Efficacy Results: PANC-1 Control and Single Agent Groups (Day 25)

| GROUP | DOSE | ROUTE/ SCHEDULE | FINAL TUMOR VOLUME (DAY 25) MEAN (MM³) ± SEM | % TGI | #PR/CR | % TR |
|---|---|---|---|---|---|---|
| Vehicle | — | IV/Q4Dx3 | 2234 ± 402 | | 0/0 | |
| Gemcitabine | 40 mg/kg | IP/Q3Dx4 | 1566 ± 255 | 31 | 1/0 | 62% |
| Gemcitabine | 80 mg/kg | IP/Q3Dx4 | 1172 ± 234 | 51 | 0/0 | |
| FK228 | 2.5 mg/kg | IV/Q4Dx3 | 1688 ± 290 | 26 | 0/0 | |
| FK228 | 5 mg/kg | IV/Q4Dx3 | 1690 ± 331 | 26 | 0/0 | |

N = 9/GRP ON DAY 1

Vehicle Control Group (2% EtOH: 8% PG: 80% Saline; IV; Q4Dx3)

Figure 5:
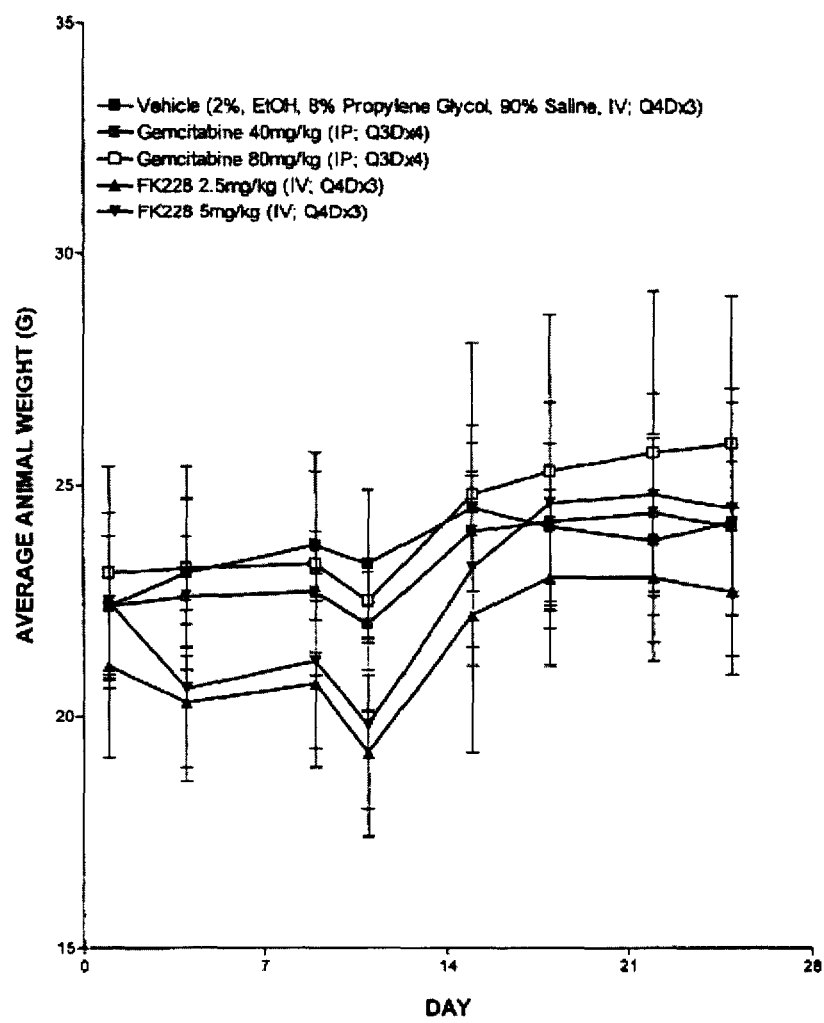
FIG. 5 shows FK-228 vs. PANC-1 Human Pancreatic Tumor Xenograft Model.
Figure 6:
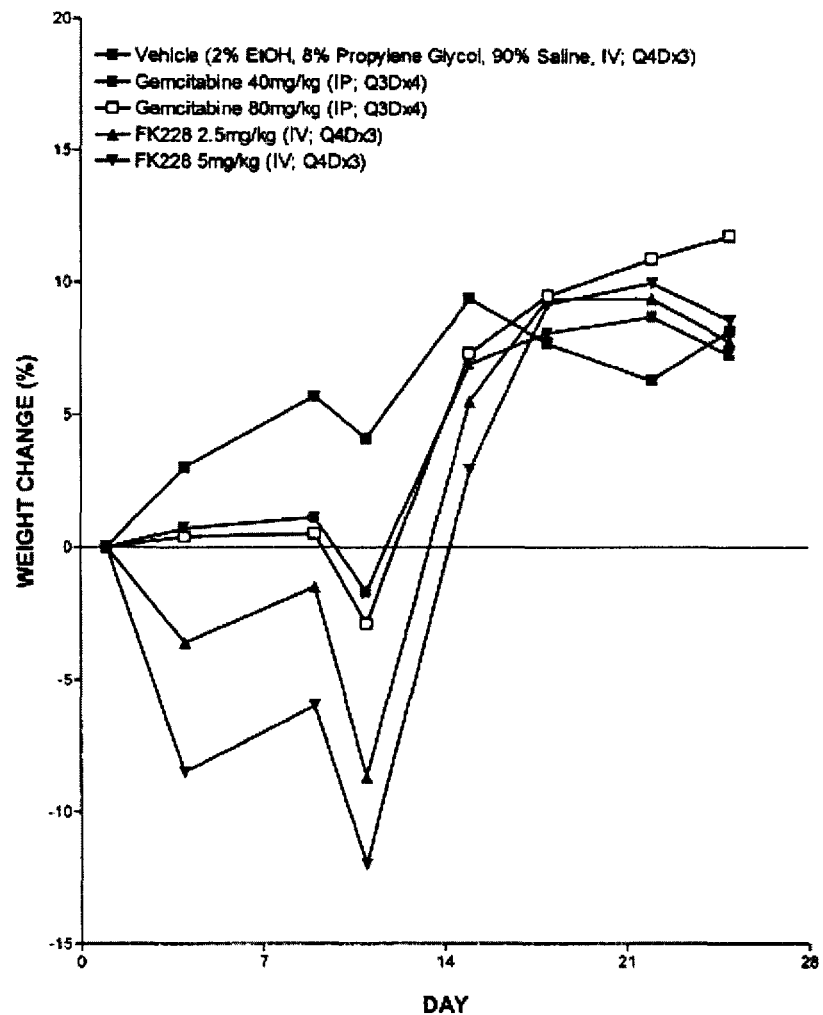
FIG. 6 shows FK-228 vs. PANC-1 Human Pancreatic Tumor Xenograft Model.

Animal Weights: A final mean weight of 24±3 grams was calculated at study completion (Day 25). No weight loss was reported in this study. Mean animal weights and percent change from Day 1 are reported in Table 2 and FIGS. 5-6.

Moribundity/Mortality: 0/9 animals reported vehicle-related toxicity or deaths (Table 2).

Figure 7:
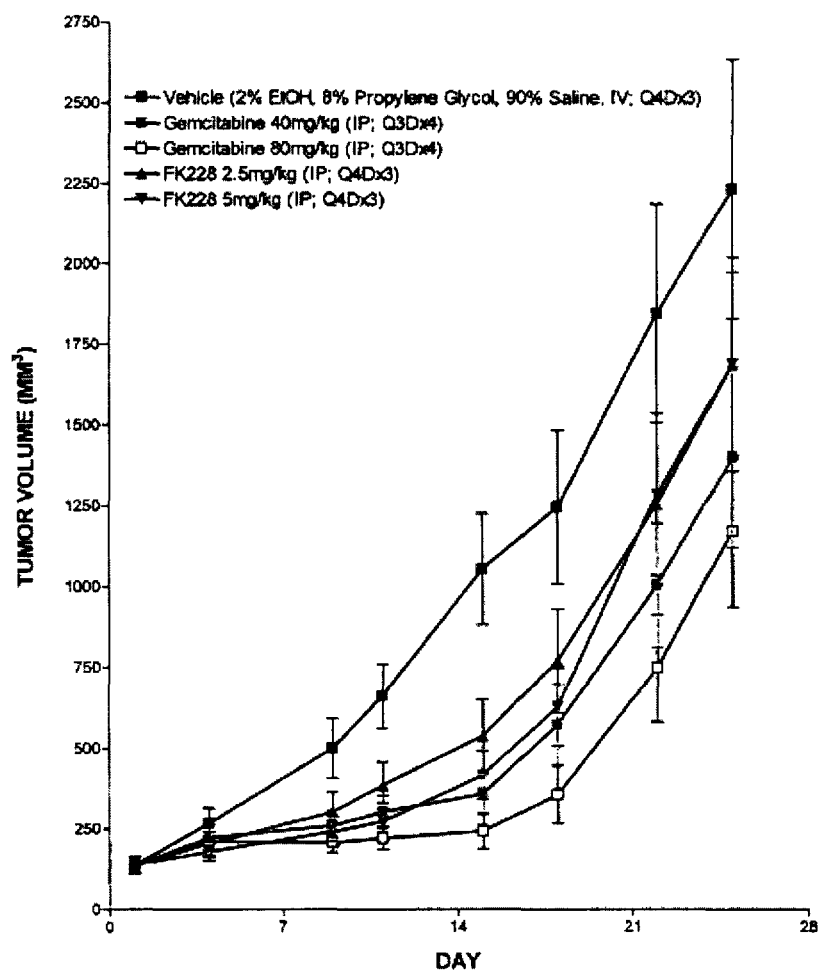
FIG. 7 shows FK-228 vs. PANC-1 Human Pancreatic Tumor Xenograft Model.
Figure 8:
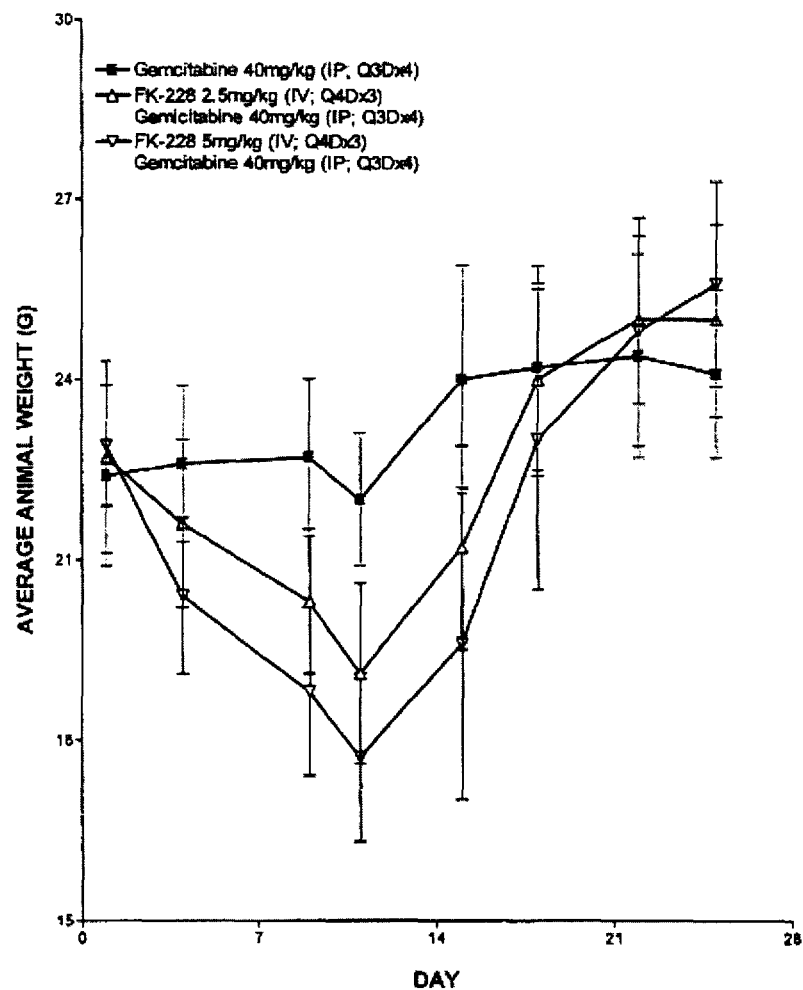
FIG. 8 shows FK-228+Gemcitabine 40 mg/kg vs. PANC-1 Human Pancreatic Tumor Xenograft Model
Figure 9:
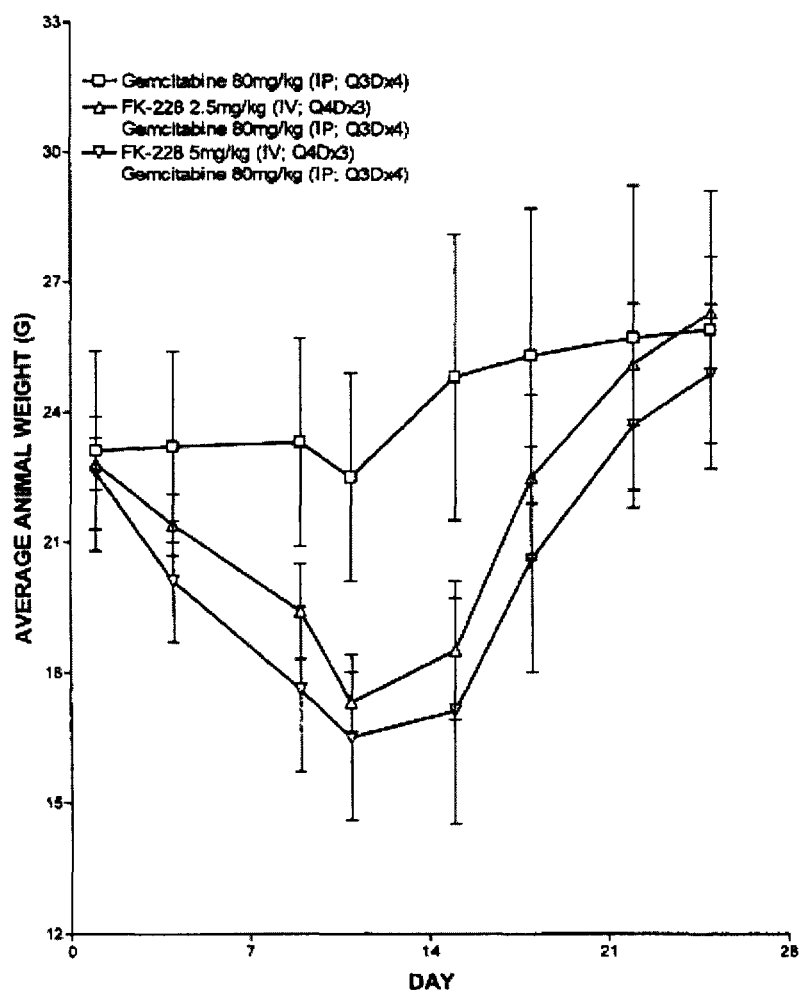
FIG. 9 shows FK-228+Gemcitabine 80 mg/kg vs. PANC-1 Human Pancreatic Tumor Xenograft Model.
Figure 10:
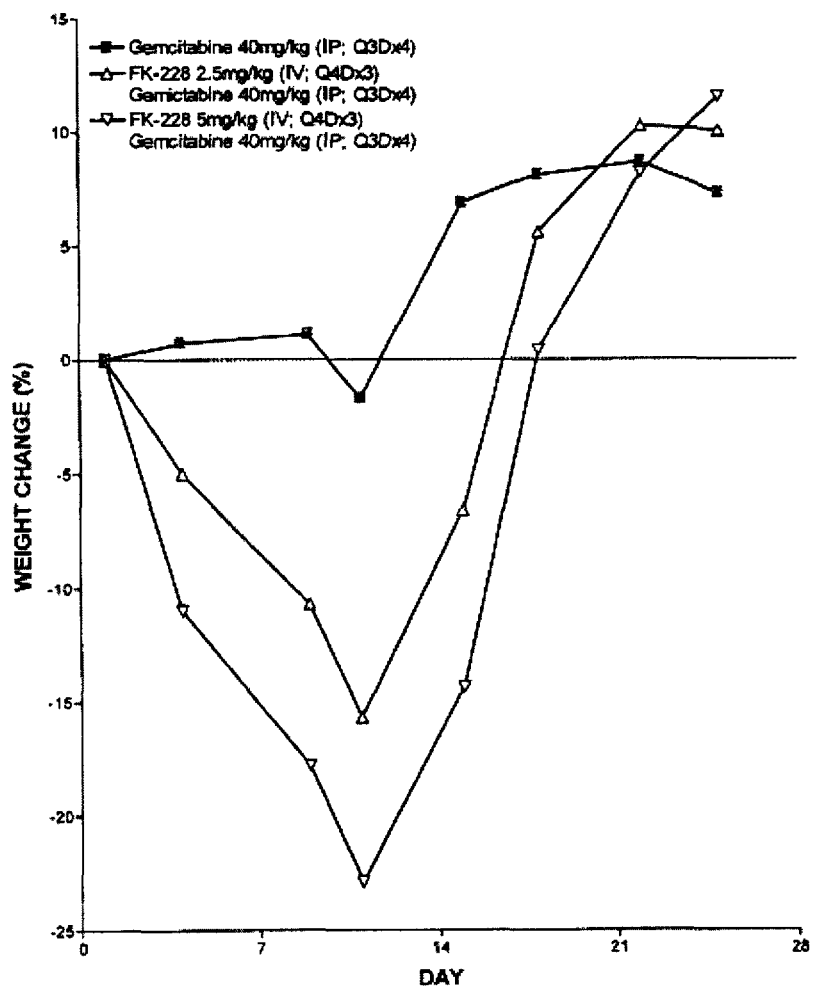
FIG. 10 shows FK-228+Gemcitabine 40 mg/kg vs. PANC-1 Human Pancreatic Tumor Xenograft Model.
Figure 11:
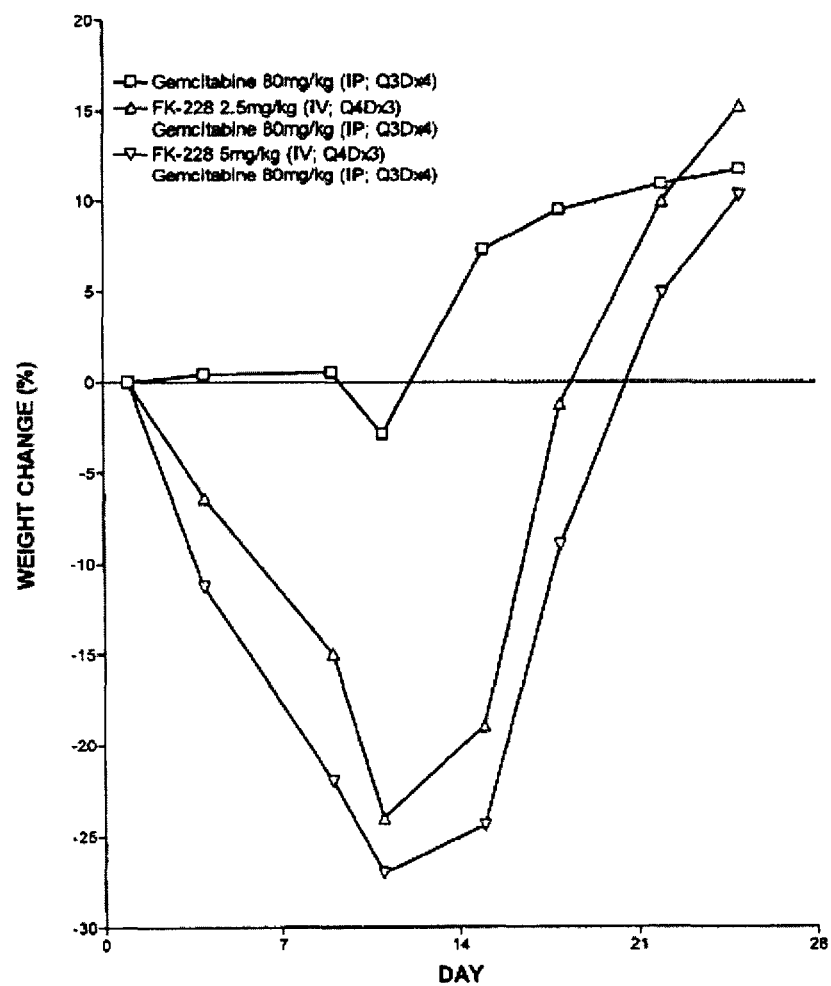
FIG. 11 shows FK-228+Gemcitabine 80 mg/kg vs. PANC-1 Human Pancreatic Tumor Xenograft Model.

Tumor Volume: A final mean tumor volume of 2234±402 mm$^3$ calculated at study completion (Day 25). Mean tumor volumes beginning Day 1 are reported in Table 3 and FIG. 7; individual and mean raw tumor volume data is included in Appendix II.

Tumor Growth Inhibition: N/A (Table 3)

Partial/Complete Tumor Response: No spontaneous tumor regressions were reported (Table 3).

Tumor Necrosis: 1/9 animals reported moderate tumor necrosis; 6/9 reported severe necrosis; this is not uncommon in the PANC-1 model.

Single Agent Treatment Groups

I. Gemcitabine; 40 mq/kq; IP; Q3Dx4

Animal Weights: A final mean weight of 24±1 grams was calculated at study completion (Day 25). Slight weight loss was reported (nadir=−2%, Day 11) which was recovered by study completion. Mean animal weights and percent change from Day 1 are reported in Table 2 and FIGS. 5-6.

Moribundity/Mortality: 0/9 animals reported drug-related toxicity or deaths (Table 2).

Tumor Volume: A final mean tumor volume of 1566±255 mm$^3$ was calculated at study completion (Day 25). Mean tumor volumes beginning Day 1 are reported in Table 3 and FIG. 7.

Tumor Growth Inhibition: A TGI of 31% was reported versus control in this study (Table 3); this agent is considered inactive according to NCI Standards[7] (TGI<58%) at the evaluated dose, schedule, and route of administration. In addition, activity of this agent was found statistically insignificant ($p>0.05$) compared with control using a two-tailed One-Way Analysis of Variance (ANOVA) followed by the Dunnett multiple comparisons test.

Partial/Complete Tumor Response: 1/9 animals reported a partial tumor response with a 62% tumor regression (Table 3).

Tumor Necrosis: 1/9 animals reported mild tumor necrosis and 4/9 reported moderate necrosis, which was unremarkable compared with control.

II. Gemcitabine; 80 mg/kg; IP; Q3Dx4

Animal Weights: A final mean weight of 26±3 grams was calculated at study completion (Day 25). Slight weight loss was reported (nadir=−3%, Day 11) which was recovered by study completion. Mean animal weights and percent change from Day 1 are reported in Table 2 and FIGS. 5-6.

Moribundity/Mortality: 0/9 animals reported drug-related toxicity or deaths (Table 2).

Tumor Volume: A final mean tumor volume of 1172±234 mm$^3$ was calculated at study completion (Day 25). Mean tumor volumes beginning Day 1 are reported in Table 3 and FIG. 7.

Tumor Growth Inhibition: A TGI of 51% was reported versus control in this study (Table 3); this agent is considered inactive according to NCI Standards[7] (TGI<58%) at the evaluated dose, schedule, and route of administration. In addition, activity of this agent was found statistically insignificant ($p>0.05$) compared with control using a two-tailed One-Way Analysis of Variance (ANOVA) followed by the Dunnett multiple comparisons test.

Partial/Complete Tumor Response: 0/9 animals reported partial or complete tumor responses (Table 3).

Tumor Necrosis: 1/9 animals reported slight tumor necrosis, 2/9 reported mild tumor necrosis, and 1/9 reported moderate necrosis; observations were unremarkable compared with control.

III. FK228; Z5 mg/kg; IV; Q4Dx3

Animal Weights: A final mean weight of 23±2 grams was calculated at study completion (Day 25). Modest weight loss was reported (nadir=−9%, Day 11) which was recovered by study completion. Mean animal weights and percent change from Day 1 are reported in Table 2 and FIGS. 5-6.

Moribundity/Mortality: 0/9 animals reported drug-related toxicity or deaths (Table 2).

Tumor Volume: A final mean tumor volume of 1688±290 mm$^3$ was calculated at study completion (Day 25). Mean tumor volumes beginning Day 1 are reported in Table 3 and FIG. 7.

Tumor Growth Inhibition: A TGI of 26% was reported versus control in this study (Table 3); this agent is considered inactive according to NCI Standards[7] (TGI<58%) at the evaluated dose, schedule, and route of administration. In addition, activity of this agent was found statistically insignificant ($p>0.05$) compared with control using a two-tailed One-Way Analysis of Variance (ANOVA) followed by the Dunnett multiple comparisons test.

Partial/Complete Tumor Response: 0/9 animals reported partial or complete tumor responses (Table 3).

Tumor Necrosis: 1/9 animals reported slight tumor necrosis, 1/9 reported mild tumor necrosis, 2/9 reported moderate necrosis, and 1/9 reported severe necrosis; observations were unremarkable compared with control.

IV. FK228; 5 mg/kg; IV; Q4Dx3

Animal Weights: A final mean weight of 25±2 grams was calculated at study completion (Day 25). Moderate weight loss was reported (nadir=−12%, Day 11) which was recovered by study completion. Mean animal weights and percent change from Day 1 are reported in Table 2 and FIGS. 5-6.

Moribundity/Mortality: 0/9 animals reported drug-related toxicity or deaths (Table 2).

Tumor Volume: A final mean tumor volume of 1690±290 mm$^3$ was calculated at study completion (Day 25). Mean tumor volumes beginning Day 1 are reported in Table 3 and FIG. 7.

Tumor Growth Inhibition: A TGI of 26% was reported versus control in this study (Table 3); this agent is considered inactive according to NCI Standards m (TGI<58%) at the evaluated dose, schedule, and route of administration. In addition, activity of this agent was found statistically insignificant ($p>0.05$) compared with control using a two-tailed One-Way Analysis of Variance (ANOVA) followed by the Dunnett multiple comparisons test (Appendix III).

Partial/Complete Tumor Response: 0/9 animals reported partial or complete tumor responses (Table 3).

Tumor Necrosis: 2/9 animals reported slight tumor necrosis, and 1/9 reported moderate necrosis; observations were unremarkable compared with control.

Combination Treatment Groups

TABLE 4

Animal Weight and Drug Toxicity Results: PANC-1 Combination Groups (Day 25)

| Group | Dose | Route/Schedule | Final Weight Data (Day 25) Mean ± SD | % change | Weight Nadir % change | day | Drug Toxicity |
|---|---|---|---|---|---|---|---|
| Gemcitabine | 40 mg/kg | IP/Q3Dx4 | 24 ± 1 | +7 | −2 | 11 | 0 |
| Gemcitabine | 80 mg/kg | IP/Q3Dx4 | 26 ± 3 | +12 | −3 | 11 | 0 |
| FK228 | 2.5 mg/kg | IV/Q4Dx3 | 25 ± 2 | +10 | −16 | 11 | 0 |
| Gemcitabine | 40 mg/kg | IP/Q3Dx4 | | | | | |
| FK228 | 5 mg/kg | IV/Q4Dx3 | 26 ± 2 | +12 | −23 | 11 | 0 |
| Gemcitabine | 40 mg/kg | IP/Q3Dx4 | | | | | |
| FK228 | 2.5 mg/kg | IV/Q4Dx3 | 26 ± 1 | +15 | −24 | 11 | 1 |
| Gemcitabine | 80 mg/kg | IP/Q3Dx4 | | | | | |
| FK228 | 5 mg/kg | IV/Q4Dx3 | 25 ± 2 | +10 | −27 | 11 | 1 |
| Gemcitabine | 80 mg/kg | IP/Q2Dx4 | | | | | |

N = 9/GRP ON DAY 1

TABLE 5

Tumor Volume and Efficacy Results: PANC-1 Combination Groups (Day 25)
FINAL TUMOR VOLUME (DAY 25)

| Group | Dose | Route/Schedule | Mean ± SEM | % TGI | # PR/CR | % TR |
|---|---|---|---|---|---|---|
| Gemcitabine | 40 mg/kg | IP/Q3Dx4 | 1566 ± 255 | 31 | 1/0 | 62% |
| Gemcitabine | 80 mg/kg | IP/Q3Dx4 | 1172 ± 234 | 51 | 0/0 | 0% |
| FK228 | 2.5 mg/kg | IV/Q4Dx3 | 600 ± 129 | 78 | 0/0 | 0% |
| Gemcitabine | 40 mg/kg | IP/Q3Dx4 | | | | |
| FK228 | 5 mg/kg | IV/Q4Dx3 | 326 ± 70 | 90 | 1/0 | 76% |
| Gemcitabine | 40 mg/kg | IP/Q3Dx4 | | | | |
| FK228 | 2.5 mg/kg | IV/Q4Dx3 | 383 ± 98 | 88 | 0/0 | 0% |
| Gemcitabine | 80 mg/kg | IP/Q3Dx4 | | | | |
| FK228 | 5 mg/kg | IV/Q4Dx3 | 147 ± 63 | 97 | 3/0 | 66% |
| Gemcitabine | 80 mg/kg | IP/Q2Dx4 | | | | |

N = 9/GRP ON DAY 1
*P < 0.001 vs. standard agent alone

I. FK228; 2.5 mg/kg; IV; Q4Dx3+Gemcitabine; 40 mg/kg; IP; Q3Dx4

Animal Weights: A final mean weight of 25±2 grams was calculated at study completion (Day 25). Significant weight loss was reported (nadir=−16%, Day 11), which is comparable to additive loss from single agent groups; weight was fully recovered by study completion. Mean animal weights and percent change from Day 1 are reported in Table 4 and FIGS. 8-11.

Moribundity/Mortality: % animals reported drug-related toxicity or deaths (Table 4).

Figure 12:
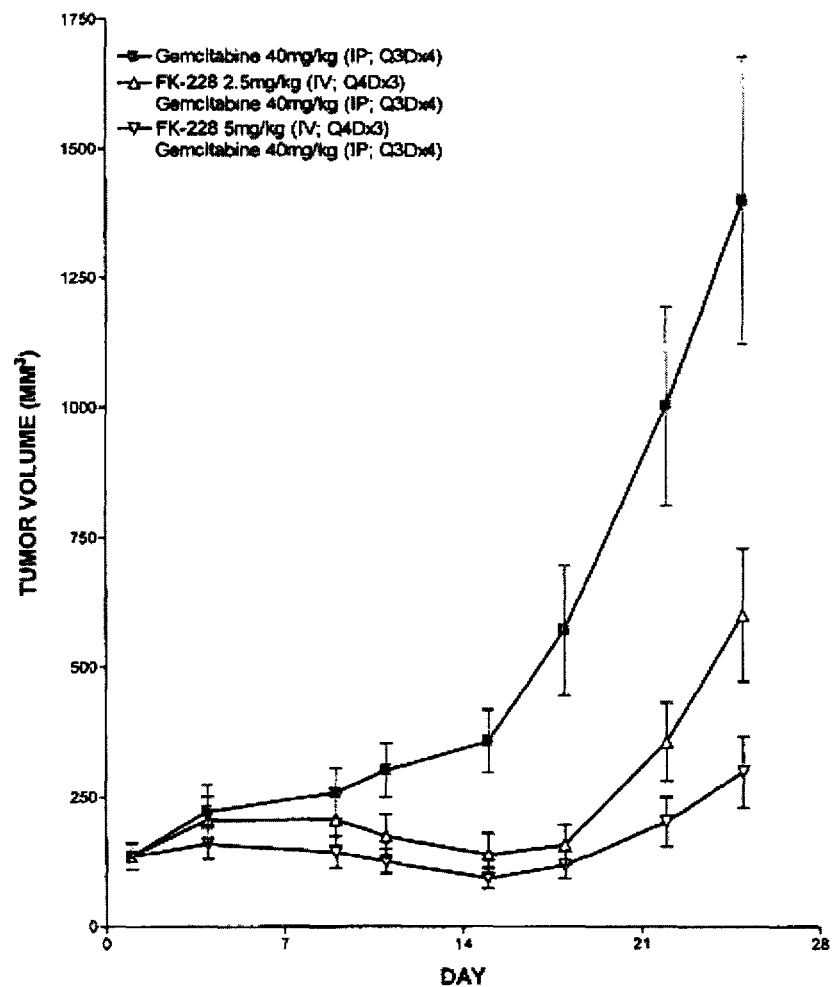
FIG. 12 shows FK-228+Gemcitabine 40 mg/kg vs. PANC-1 Human Pancreatic Tumor Xenograft Model.
Figure 13:
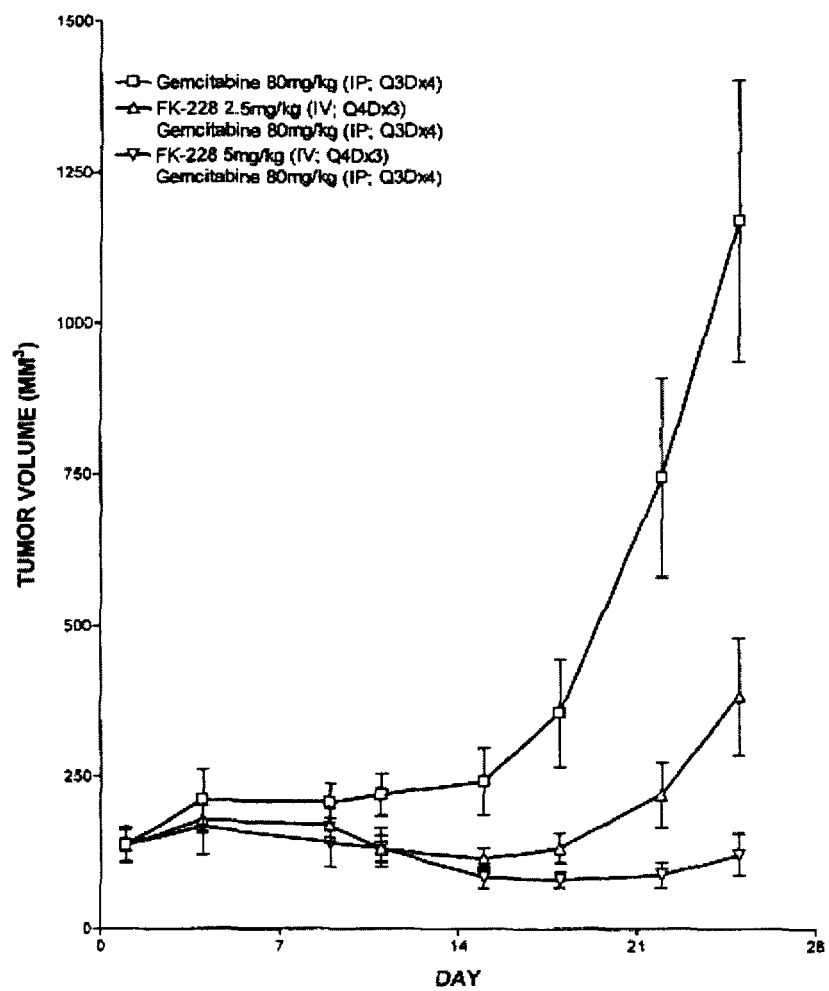
FIG. 13 shows FK-228+Gemcitabine 80 mg/kg vs. PANC-1 Human Pancreatic Tumor Xenograft Model.

Tumor Volume: A final mean tumor volume of 600±129 mm$^3$ was calculated at study completion (Day 25). Mean tumor volumes beginning Day 1 are reported in Table 5 and FIGS. 12-13.

Tumor Growth Inhibition: A TGI of 78% was reported versus control in this study (Table 5); this combination is considered active according to NCI Standards[7] (TGI>58%) at the evaluated doses, schedules, and routes of administration. In addition, activity of this combination was found statistically significant (p<0.001) compared with 40 mg/kg gemcitabine alone using a two-tailed One-Way Analysis of Variance (ANOVA) followed by the Dunnett multiple comparisons test.

Partial/Complete Tumor Response: % animals reported partial or complete tumor responses (Table 5).

Tumor Necrosis: % animals reported tumor necrosis; observations were remarkable compared with control or either single agent group at Day 25 or at similar mean tumor volume.

II. FK228; 5 mg/kg; IV; Q4Dx3+Gemcitabine; 40 mg/kg; IP; Q3Dx4

Animal Weights: A final mean weight of 26±2 grams was calculated at study completion (Day 25). Significant weight loss was reported (nadir=−23%, Day 11), which is increased compared to additive loss from single agent groups; weight was fully recovered by study completion. Mean animal weights and percent change from Day 1 are reported in Table 4 and FIGS. 8-11.

Moribundity/Mortality: % animals reported drug-related toxicity or deaths (Table 4).

Tumor Volume: A final mean tumor volume of 326±70 mm$^3$ was calculated at study completion (Day 25). Mean tumor volumes beginning Day 1 are reported in Table 5 and FIGS. 12-13.

Tumor Growth Inhibition: A TGI of 90% was reported versus control in this study (Table 5); this combination is considered active according to NCI Standards[7] (TGI>58%) at the evaluated doses, schedules, and routes of administration. In addition, activity of this combination was found statistically significant (p<0.001) compared with 40 mg/kg gemcitabine alone using a two-tailed One-Way Analysis of Variance (ANOVA) followed by the Dunnett multiple comparisons test.

Partial/Complete Tumor Response: 1/9 animals reported a partial tumor response with a 76% tumor regression (Table 5).

Tumor Necrosis: 0/9 animals reported tumor necrosis; observations were remarkable compared with control or either single agent group at Day 25 or at similar mean tumor volume.

III. FK228; 2.5 mg/kg; IV; Q4Dx3+Gemcitabine; 80 mg/kg; IP; Q3Dx4

Animal Weights: A final mean weight of 26±1 grams was calculated at study completion (Day 25). Significant weight loss was reported (nadir=−24%, Day 11), which is increased compared to additive loss from single agent groups; weight was fully recovered by study completion. Mean animal weights and percent change from Day 1 are reported in Table 4 and FIGS. 8-11.

Moribundity/Mortality: 1/9 animals reported a drug-related death on Day 11 (Table 4).

Tumor Volume: A final mean tumor volume of 383±103 mm³ was calculated at study completion (Day 25). Mean tumor volumes beginning Day 1 are reported in Table 5 and FIGS. 12-13.

Tumor Growth Inhibition: A TGI of 88% was reported versus control in this study (Table 5); this combination is considered active according to NCI Standards[7] (TGI>58%) at the evaluated doses, schedules, and routes of administration. In addition, activity of this combination was found statistically significant (p<0.001) compared with 80 mg/kg gemcitabine alone using a two-tailed One-Way Analysis of Variance (ANOVA) followed by the Dunnett multiple comparisons test.

Partial/Complete Tumor Response: % animals reported partial or complete tumor responses (Table 5).

Tumor Necrosis: 1/9 animals reported slight tumor necrosis; observations were remarkable compared with control or either single agent group at Day 25 or at similar mean tumor volume.

IV. FK228; 5 mg/kg; IV; Q4Dx3 Gemcitabine; 80 mg/kg; IP; Q3Dx4

Animal Weights: A final mean weight of 25±2 grams was calculated at study completion (Day 25). Significant weight loss was reported (nadir=−27%, Day 11), which is increased compared to additive loss from single agent groups; weight was fully recovered by study completion. Mean animal weights and percent change from Day 1 are reported in Table 4 and FIGS. 8-11.

Moribundity/Mortality: 1/9 animals reported drug-related deaths on Day and 1/9 on Day 15 (Table 4).

Tumor Volume: A final mean tumor volume of 147±63 mm³ was calculated at study completion (Day 25). Mean tumor volumes beginning Day 1 are reported in Table 5 and FIGS. 12-13.

Tumor Growth Inhibition: A TGI of 97% was reported versus control in this study (Table 5); this combination is considered active according to NCI Standards[7] (TGI>58%) at the evaluated doses, schedules, and routes of administration. In addition, activity of this combination was found statistically significant (p<0.001) compared with 80 mg/kg gemcitabine alone using a two-tailed One-Way Analysis of Variance (ANOVA) followed by the Dunnett multiple comparisons test.

Partial/Complete Tumor Response: 3/9 animals reported a partial tumor response with a 66% mean tumor regression (Table 5).

Tumor Necrosis: 0/9 animals reported tumor necrosis; observations were remarkable compared with control or either single agent group at Day 25 or at similar mean tumor volume.

BxPC-3 Study Results

TABLE 6

Animal Weight and Drug Toxicity Results: BxPC-3 Control and Single Agent Groups (Day 29)

| GROUP | DOSE | ROUTE/SCHEDULE | FINAL WEIGHT DATA (DAY 29) MEAN (G) ± SD | % CHANGE | WEIGHT NADIR % CHANGE | DAY | DRUG DEATHS TOTAL | DAY (#) |
|---|---|---|---|---|---|---|---|---|
| Vehicle | — | IV/Q4Dx3 | 25 ± 2 | +6 | — | — | 0 | — |
| Gemcitabine | 40 mg/kg | IP/Q3Dx4 | 25 ± 3 | +9 | — | — | 0 | — |
| Gemcitabine | 80 mg/kg | IP/Q3Dx4 | 22 ± 4 | +1 | −9 | 11 | 0 | — |
| FK228 | 2.5 mg/kg | IV/Q4Dx3 | 25 ± 2 | +10 | −5 | 11 | 0 | — |
| FK228 | 5 mg/kg | IV/Q4Dx3 | 24 ± 1 | +7 | −15 | 11 | 0 | — |

N = 8/GRP ON DAY 1

TABLE 7

Tumor Volume and Efficacy Results: BxPC-3 Control and Single Agent Groups (Day 29)

| GROUP | DOSE | ROUTE/ SCHEDULE | FINAL TUMOR VOLUME (DAY 29) MEAN ± SEM | % TGI | #PR/CR | % TR |
|---|---|---|---|---|---|---|
| Vehicle | — | IV/Q4Dx3 | 2073 ± 315 | — | 0/0 | — |
| Gemcitabine | 40 mg/kg | IP/Q3Dx4 | 1683 ± 426 | 20 | 0/0 | — |
| Gemcitabine | 80 mg/kg | IP/Q3Dx4 | 1890 ± 237 | 9 | 0/0 | — |
| FK228 | 2.5 mg/kg | IV/Q4Dx3 | 2440 ± 643 | — | 0/0 | — |
| FK228 | 5 mg/kg | IV/Q4Dx3 | 2620 ± 238 | — | 0/0 | — |

N = 8/GRP ON DAY 1

Vehicle Control Group (2% EtOH:8% PG: 80% Saline; IV; Q4Dx3)

Figure 14:
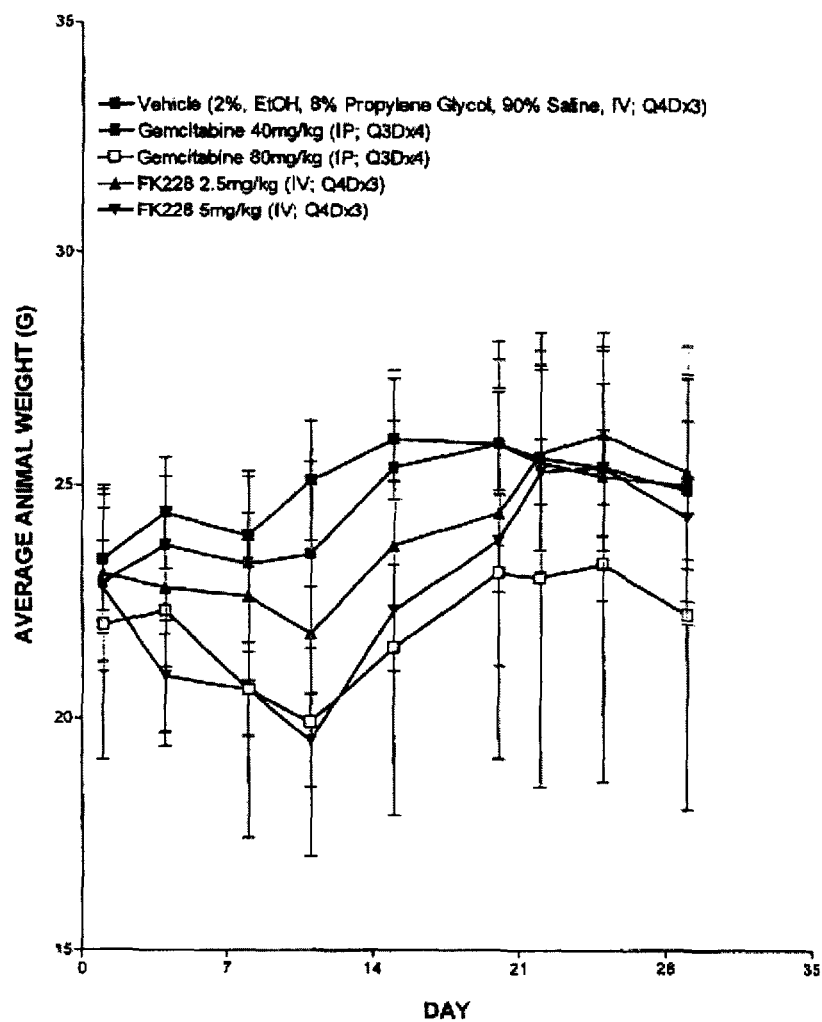
FIG. 14 shows FK-228 vs. BxPC-3 Human Pancreatic Tumor Xenograft Model.
Figure 15:
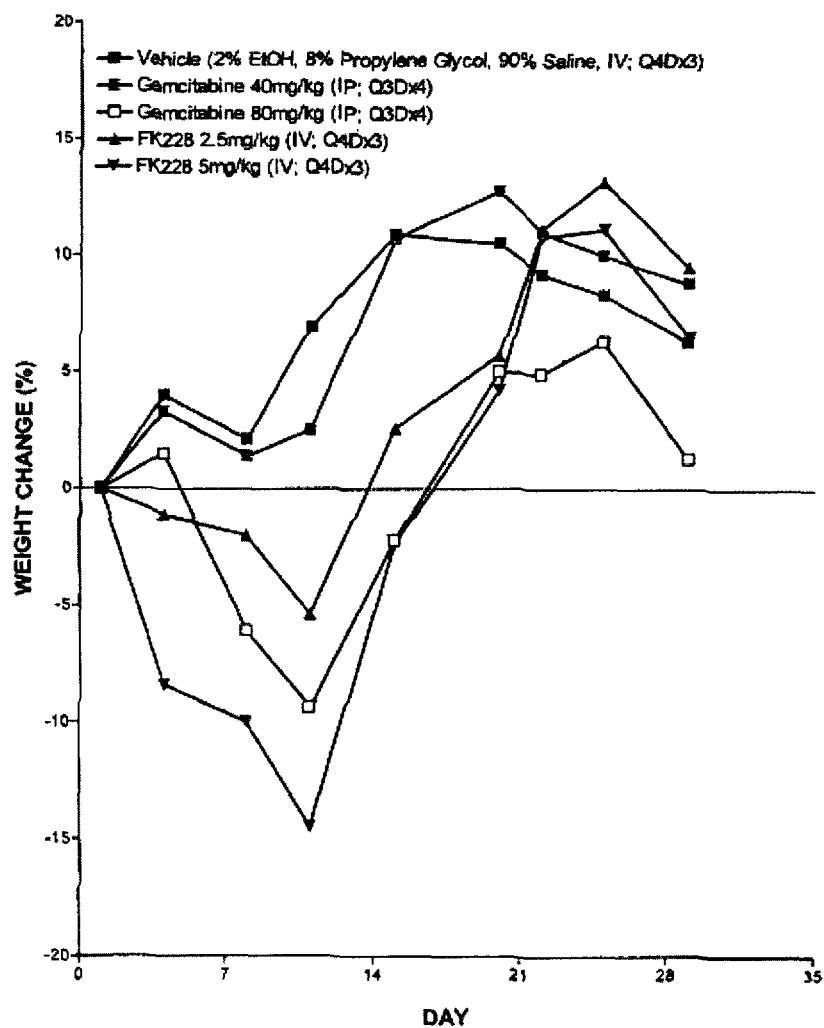
FIG. 15 shows FK-228 vs. BxPC-3 Human Pancreatic Tumor Xenograft Model.

Animal Weights: A final mean weight of 25±2 grams was calculated at study completion (Day 29). No weight loss was reported in this study. Mean animal weights and percent change from Day 1 are reported in Table 6 and FIGS. 14-15.

Moribundity/Mortality: % animals reported vehicle-related toxicity or deaths (Table 6).

Figure 16:
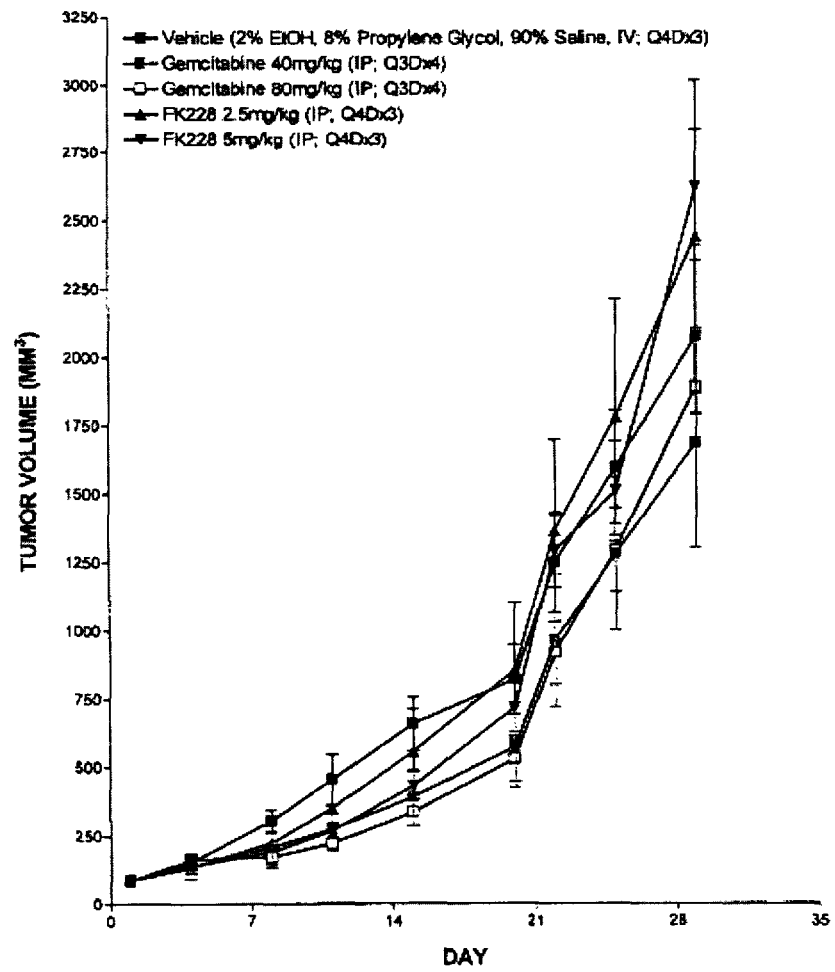
FIG. 16 shows FK-228 vs. BxPC-3 Human Pancreatic Tumor Xenograft Model.
Figure 17:
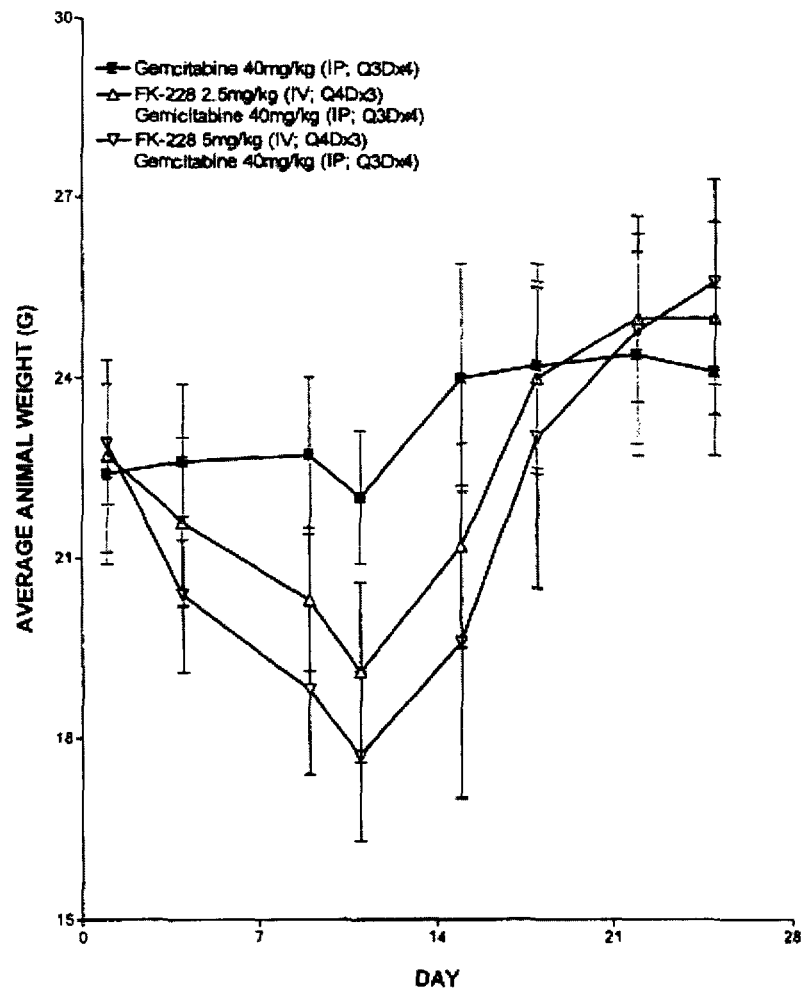
FIG. 17 shows FK-228+Gemcitabine 40 mg/kg vs. PANC-1 Human Pancreatic Tumor Xenograft Model
Figure 18:
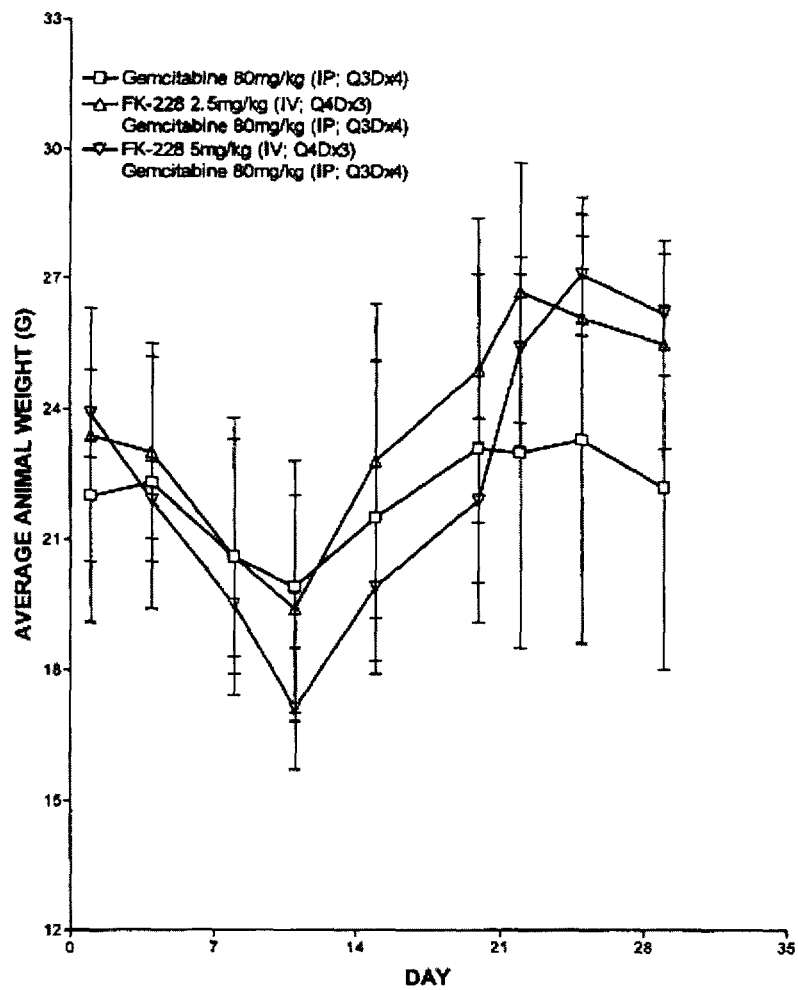
FIG. 18 shows FK-228+Gemcitabine 80 mg/kg vs. BxPC-3 Human Pancreatic Tumor Xenograft Model.
Figure 19:
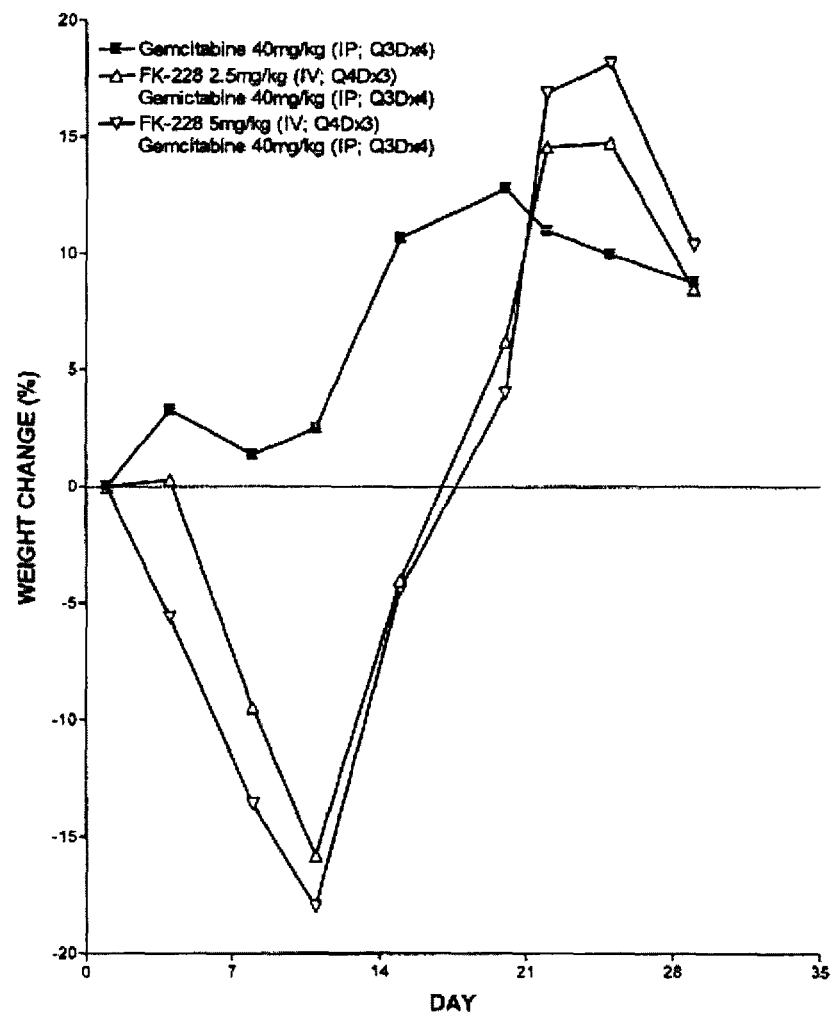
FIG. 19 shows FK-228+Gemcitabine 40 mg/kg vs. BxPC-3 Human Pancreatic Tumor Xenograft Model.
Figure 20:
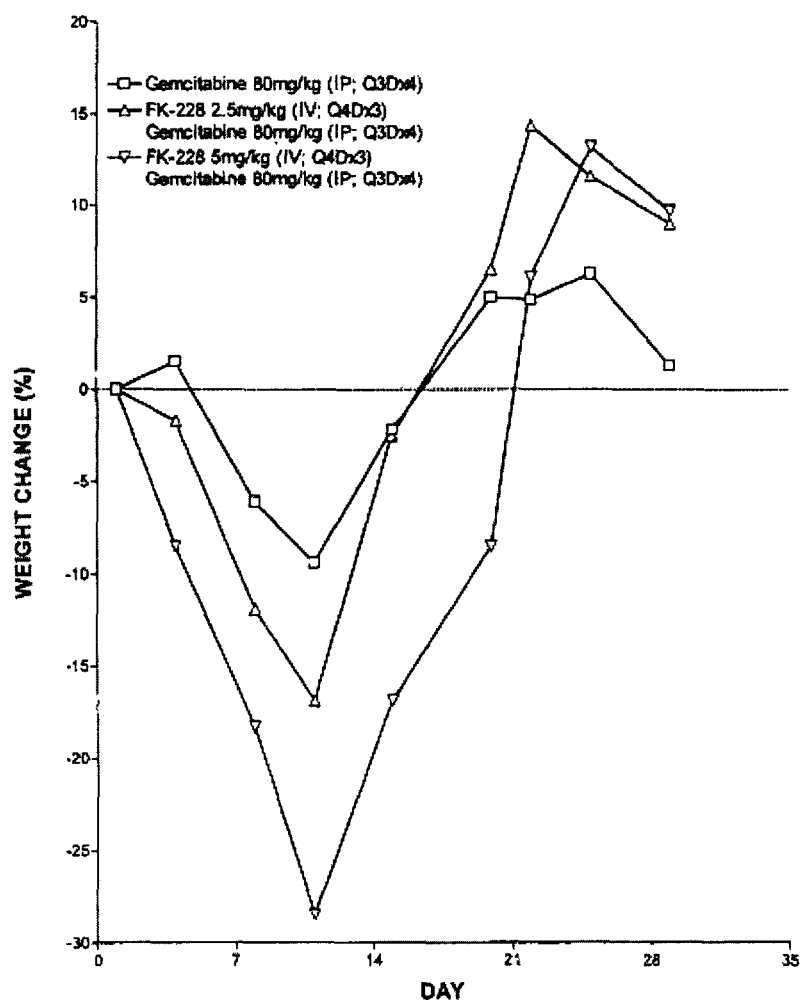
FIG. 20 shows FK-228+Gemcitabine 80 mg/kg vs. BxPC-3 Human Pancreatic Tumor Xenograft Model.

Tumor Volume: A final mean tumor volume of 2073±315 mm3 calculated at study completion (Day 29). Mean tumor volumes beginning Day 1 are reported in Table 7 and FIG. 16.

Tumor Growth Inhibition: N/A (Table 3)

Partial/Complete Tumor Response: No spontaneous tumor regressions were reported (Table 7).

Tumor Necrosis: 1/9 animals reported moderate tumor necrosis, which is not uncommon in the BxPC-3 model.

Single Agent Treatment Groups

I. Gemcitabine; 40 mg/kg; IP; Q3Dx4

Animal Weights: A final mean weight of 25±3 grams was calculated at study completion (Day 29). No weight loss was reported in this study. Mean animal weights and percent change from Day 1 are reported in Table 6 and FIGS. 14-15.

Moribundity/Mortality: % animals reported drug-related toxicity or deaths (Table 6).

Tumor Volume: A final mean tumor volume of 1683±426 mm$^3$ was calculated at study completion (Day 29). Mean tumor volumes beginning Day 1 are reported in Table 7 and FIG. 16.

Tumor Growth Inhibition: A TGI of 20% was reported versus control in this study (Table 7); this agent is considered inactive according to NCI Standards[7] (TGI<58%) at the evaluated dose, schedule, and route of administration. In addition, activity of this agent was found statistically insignificant (p>0.05) compared with control using a two-tailed One-Way Analysis of Variance (ANOVA) followed by the Dunnett multiple comparisons test.

Partial/Complete Tumor Response: % animals reported a partial/complete response (Table 7).

Tumor Necrosis: 1/9 animals reported severe tumor necrosis; observations were unremarkable compared with control.

II. Gemcitabine; 80 mg/kg; IP; Q3Dx4

Animal Weights: A final mean weight of 22±4 grams was calculated at study completion (Day 29). Modest weight loss was reported (nadir=−9%, Day 11) which was recovered by study completion. Mean animal weights and percent change from Day 1 are reported in Table 6 and FIGS. 14-15.

Moribundity/Mortality: % animals reported drug-related toxicity or deaths (Table 6).

Tumor Volume: A final mean tumor volume of 1890±237 mm$^3$ was calculated at study completion (Day 29). Mean tumor volumes beginning Day 1 are reported in Table 7 and FIG. 16.

Tumor Growth Inhibition: A TGI of 9% was reported versus control in this study (Table 7); this agent is considered inactive according to NCI Standards[7] (TGI<58%) at the evaluated dose, schedule, and route of administration. In addition, activity of this agent was found statistically insignificant (p>0.05) compared with control using a two-tailed One-Way Analysis of Variance (ANOVA) followed by the Dunnett multiple comparisons test.

Partial/Complete Tumor Response: % animals reported partial or complete tumor responses (Table 7).

Tumor Necrosis: 1/9 animals reported mild tumor necrosis; observations were unremarkable compared with control.

III. FK228; 2.5 mg/kg; IV; Q4Dx3

Animal Weights: A final mean weight of 25±2 grams was calculated at study completion (Day 29). Slight weight loss was reported (nadir=−5%, Day 11) which was recovered by study completion. Mean animal weights and percent change from Day 1 are reported in Table 6 and FIGS. 14-15.

Moribundity/Mortality: % animals reported drug-related toxicity or deaths (Table 6).

Tumor Volume: A final mean tumor volume of 2440±643 mm$^3$ was calculated at study completion (Day 29). Mean tumor volumes beginning Day 1 are reported in Table 7 and FIG. 16.

Tumor Growth Inhibition: No TGI was reported versus control in this study (Table 7); this agent is considered inactive according to NCI Standards[7] (TGI<58%) at the evaluated dose, schedule, and route of administration. In addition, activity of this agent was found statistically insignificant (p>0.05) compared with control using a two-tailed One-Way Analysis of Variance (ANOVA) followed by the Dunnett multiple comparisons test (Appendix III).

Partial/Complete Tumor Response: % animals reported partial or complete tumor responses (Table 7).

Tumor Necrosis: 2/9 animals reported mild tumor necrosis; observations were unremarkable compared with control.

IV. FK228; 5 mg/kg; IV; Q4Dx3

Animal Weights: A final mean weight of 24±1 grams was calculated at study completion (Day 29). Moderate weight loss was reported (nadir=−15%, Day 11) which was recovered by study completion. Mean animal weights and percent change from Day 1 are reported in Table 6 and FIGS. 14-15.

Moribundity/Mortality: % animals reported drug-related toxicity or deaths (Table 6).

Tumor Volume: A final mean tumor volume of 2620±238 mm$^3$ was calculated at study completion (Day 29). Mean tumor volumes beginning Day 1 are reported in Table 7 and FIG. 16.

Tumor Growth Inhibition: No TGI was reported versus control in this study (Table 7); this agent is considered inactive according to NCI Standards[7] (TGI<58%) at the evaluated dose, schedule; and route of administration. In addition, activity of this agent was found statistically insignificant (p>0.05) compared with control using a two-tailed One-Way Analysis of Variance (ANOVA) followed by the Dunnett multiple comparisons test.

Partial/Complete Tumor Response: % animals reported partial or complete tumor responses (Table 7).

Tumor Necrosis: 2/8 animals reported mild tumor necrosis; observations were unremarkable compared with control.

Combination Treatment Groups (TGI<58%) at the evaluated doses, schedules, and routes of administration. In addition, activity of this combination was found statistically insignificant (p>0.05) compared with 40 mg/kg gemcitabine alone using a two-tailed One-Way Analysis of Variance (ANOVA) followed by the Dunnett multiple comparisons test.

Partial/Complete Tumor Response: % animals reported partial or complete tumor responses (Table 9).

Tumor Necrosis: 1/8 animals reported mild tumor necrosis; observations were unremarkable compared with control.

TABLE 8

Animal Weight and Drug Toxicity Results: BxPC-3 Combination Groups (Day 29)

| Group | Dose | Route/ Schedule | Final Weight Data (Day 29) Mean ± SD | % change | Weight Nadir % change | day | Drug Deaths Total | Day |
|---|---|---|---|---|---|---|---|---|
| Gemcitabine | 40 mg/kg | IP/Q3Dx4 | 25 ± 3 | +9 | = | = | 0 | = |
| Gemcitabine | 80 mg/kg | IP/Q3Dx4 | 22 ± 4 | +1 | −9 | 11 | = | = |
| FK228 | 2.5 mg/kg | IV/Q4Dx3 | | | | | | |
| Gemcitabine | 40 mg/kg | IP/Q3Dx4 | 24 ± 1 | +9 | −16 | 11 | 0 | = |
| FK228 | 5 mg/kg | IV/Q4Dx3 | | | | | | |
| Gemcitabine | 40 mg/kg | IP/Q3Dx4 | 25 ± 1 | +10 | −18 | 11 | 0 | = |
| FK228 | 2.5 mg/kg | IV/Q4Dx3 | | | | | | |
| Gemcitabine | 80 mg/kg | IP/Q3Dx4 | 26 ± 2 | +9 | −17 | 11 | 1 | 8 |
| FK228 | 5 mg/kg | IV/Q4Dx3 | | | | | | |
| Gemcitabine | 80 mg/kg | IP/Q3Dx4 | 26 ± 1 | +10 | −29 | 11 | 1 | 8 |

N = 8/GRP ON DAY 1

TABLE 9

Tumor Volume and Efficacy Results: BxPC-3 Combination Groups (Day 29)

| GROUP | DOSE | ROUTE/SCHEDULE | FINAL TUMOR VOLUME (DAY 29) MEAN ± SEM | % TGI | #PR/CR | % TR |
|---|---|---|---|---|---|---|
| Gemcitabine | 40 mg/kg | IP/Q3Dx4 | 1683 ± 426 | 20 | 0/0 | — |
| Gemcitabine | 80 mg/kg | IP/Q3Dx4 | 1890 ± 237 | 9 | 0/0 | — |
| FK228 | 2.5 mg/kg | IV/Q4Dx3 | | | | |
| Gemcitabine | 40 mg/kg | IP/Q3Dx4 | 1663 ± 322 | 21 | 0/0 | — |
| FK228 | 5 mg/kg | IV/Q4Dx3 | | | | |
| Gemcitabine | 40 mg/kg | IP/Q3Dx4 | 1198 ± 234 | 44 | 0/0 | — |
| FK228 | 2.5 mg/kg | IV/Q4Dx3 | | | | |
| Gemcitabine | 80 mg/kg | IP/Q3Dx4 | 1278 ± 286 | 40 | 0/0 | — |
| FK228 | 5 mg/kg | IV/Q4Dx3 | | | | |
| Gemcitabine | 80 mg/kg | IP/Q3Dx4 | 1592 ± 304 | 24 | 0/0 | — |

N = 8/GRP ON DAY 1

I. FK228; 2.5 mg/kg; IV; Q4Dx3+Gemcitabine; 40 mg/kg; IP; Q3Dx4)

Animal Weights: A final mean weight of 24±1 grams was calculated at study completion (Day 29). Significant weight loss was reported (nadir=−16%, Day 11), which is increased compared to additive loss from single agent groups; weight was fully recovered by study completion. Mean animal weights and percent change from Day 1 are reported in Table 8 and FIGS. 17-20.

Moribundity/Mortality: % animals reported drug-related toxicity or deaths (Table 8).

Figure 21:
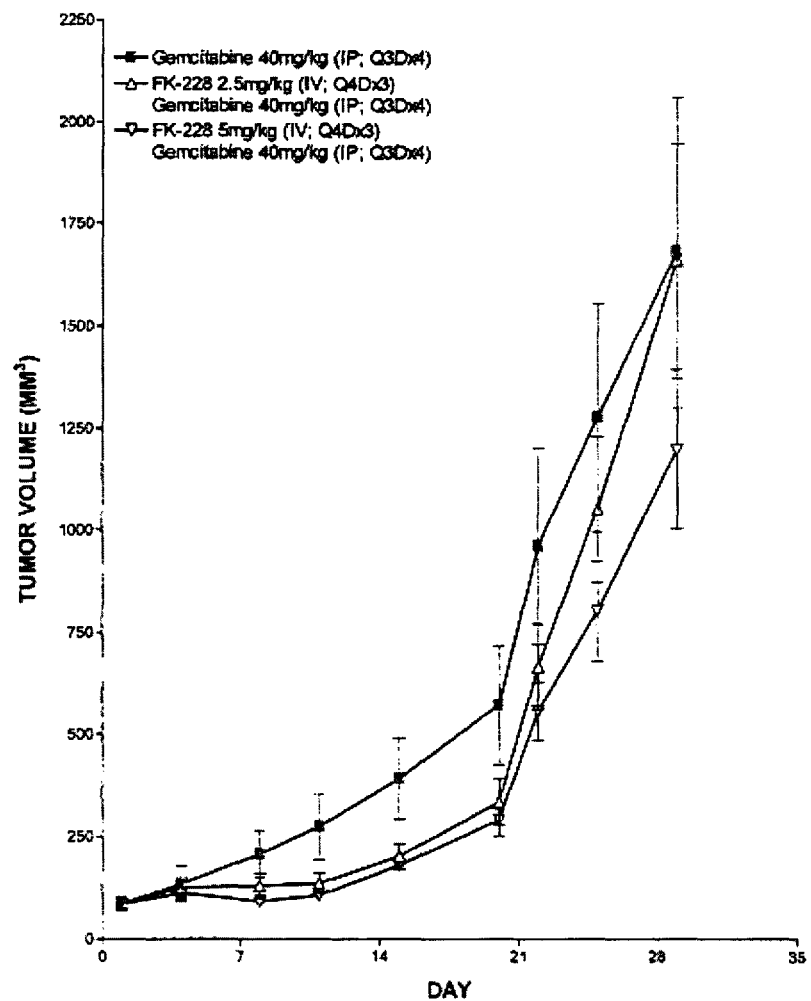
FIG. 21 shows FK-228+Gemcitabine 40 mg/kg vs. BxPC-3 Human Pancreatic Tumor Xenograft Model.
Figure 22:
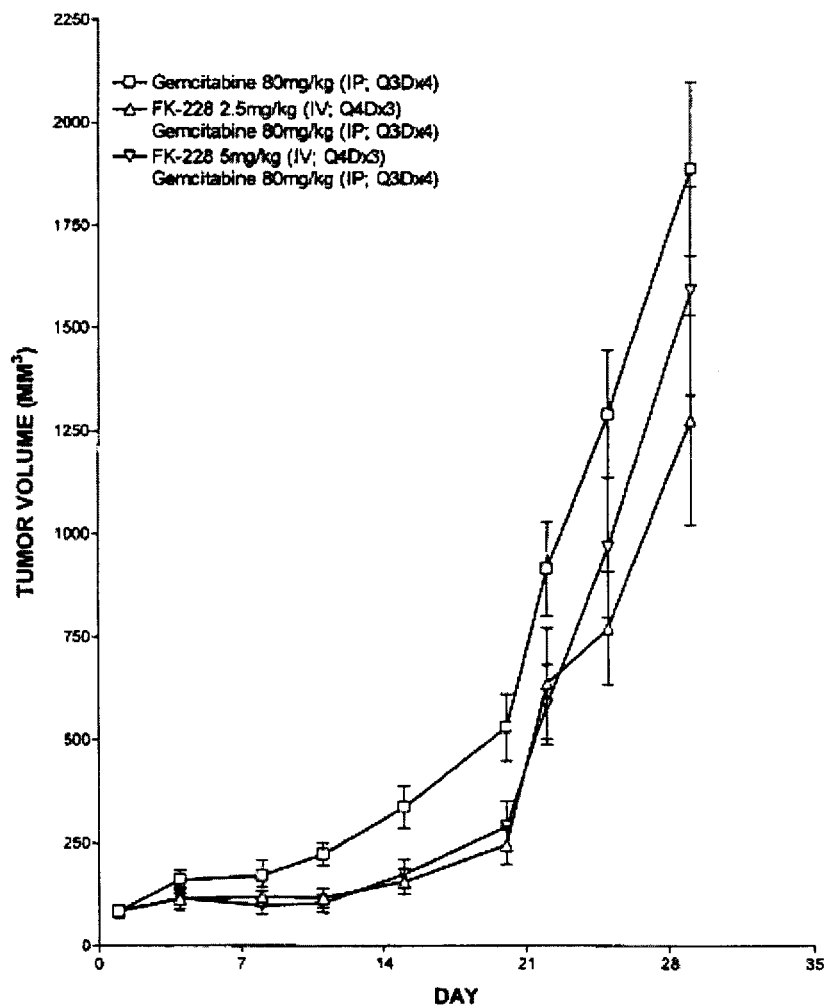
FIG. 22 shows FK-228+Gemcitabine 80 mg/kg vs. BxPC-3 Human Pancreatic Tumor Xenograft Model.
Figure 23A:
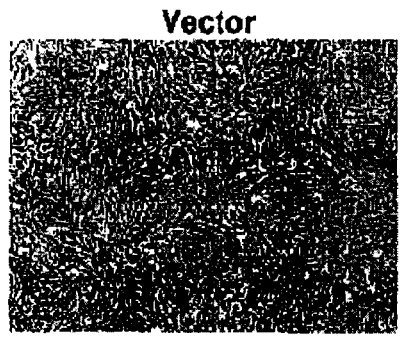
FIGS. 23A-23F shows the effect of Romidepsin on morphology of transformed Ras Expressing Tumor cells, 96 hour post-selection (23A—vector; 23B—H-Ras 12V; 23C—K-Ras 12V; 23D—N-Ras 12D; 23E—B-Raf 600E; 23F—NeuT).
Figure 23B:
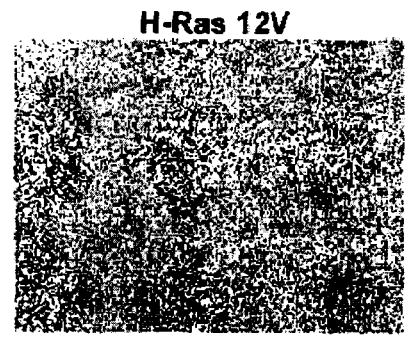
Figure 23C:
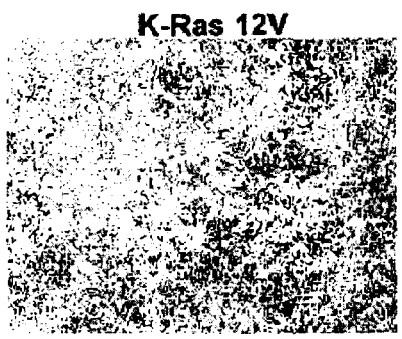
Figure 23D:
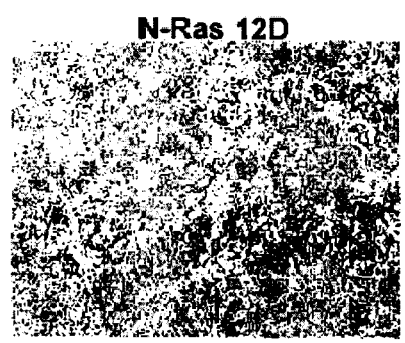
Figure 23E:
Figure 23F:
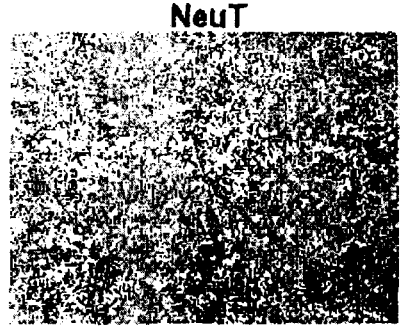
Figure 24A:
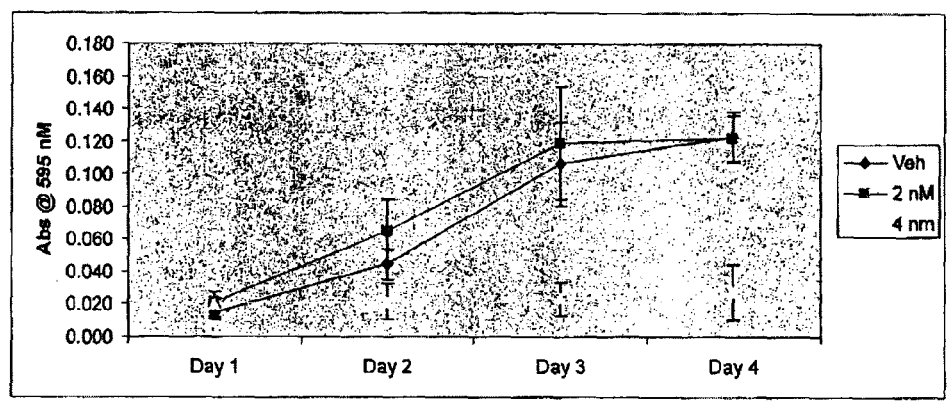
FIGS. 24A-24F show the effect of Romidepsin on proliferation of Ras expressing Tumor Cell (23A—vector; 23B—H-Ras 12V; 23C—K-Ras 12V; 23D—N-Ras 12D; 23E—B-Raf 600E; 23F—NeuT).
Figure 24B:
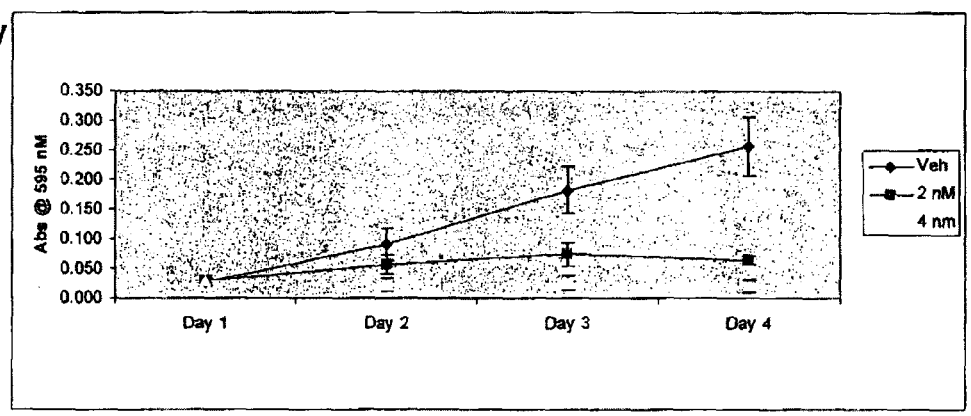
Figure 24C:
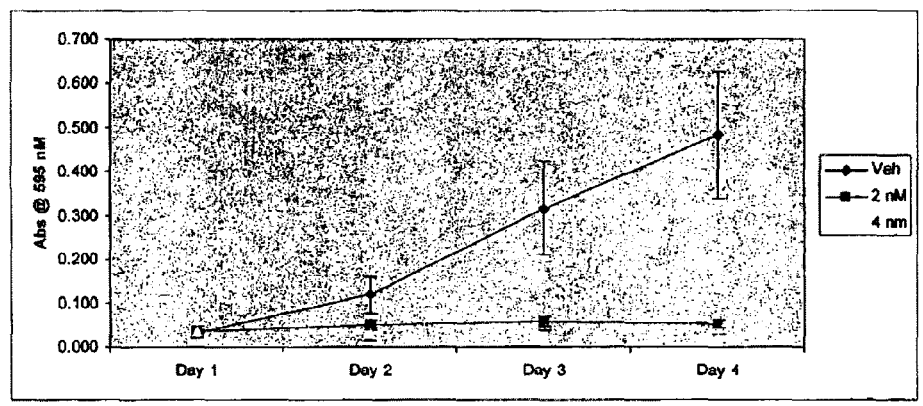
Figure 24D:
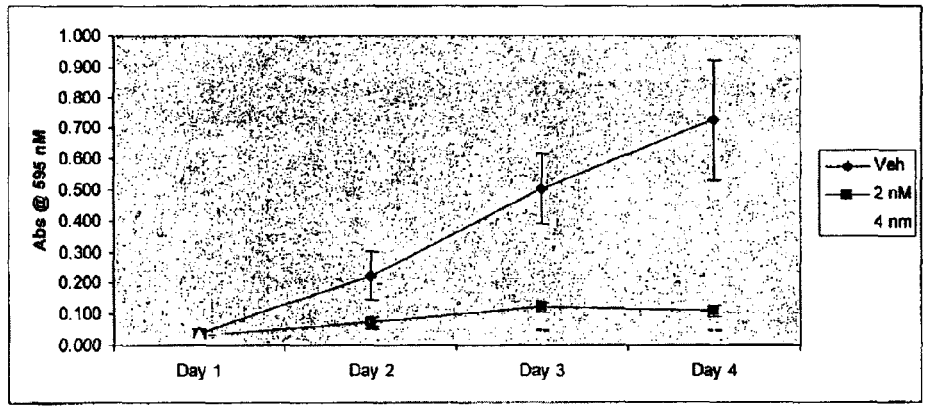
Figure 24E:
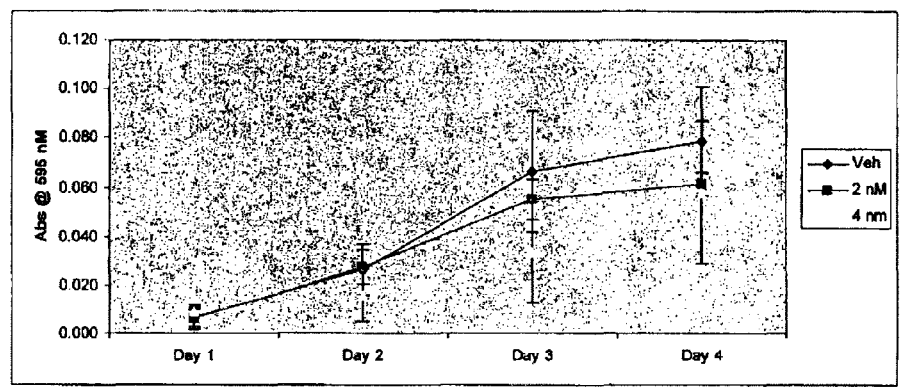
Figure 24F:
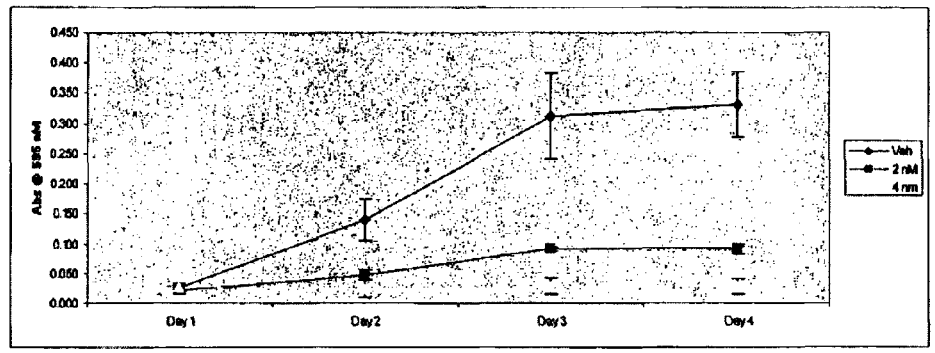

Tumor Volume: A final mean tumor volume of 1663±322 mm³ was calculated at study completion (Day 29). Mean tumor volumes beginning Day 1 are reported in Table 9 and FIGS. 21-22.

Tumor Growth Inhibition: A TGI of 21% was reported versus control in this study (Table 9); this combination is considered inactive according to NCI Standards[7]

II. (FK228; 5 mg/kg; IV; Q4Dx3+Gemcitabine; 40 mg/kg; IP; Q3Dx4)

Animal Weights: A final mean weight of 25±1 grams was calculated at study completion (Day 29): Significant weight loss was reported (nadir=−18%, Day 11), which is comparable to additive loss from single agent groups; weight was fully recovered by study completion. Mean animal weights and percent change from Day 1 are reported in Table 8 and FIGS. 17-20.

Moribundity/Mortality: % animals reported drug-related toxicity or deaths (Table 8).

Tumor Volume: A final mean tumor volume of 1198±234 mm³ was calculated at study completion (Day 29). Mean tumor volumes beginning Day 1 are reported in Table 9 and FIGS. 21-22.

Tumor Growth Inhibition: A TGI of 44% was reported versus control in this study (Table 9); this combination is considered inactive according to NCI Standards[7]

(TGI<58%) at the evaluated doses, schedules, and routes of administration. In addition, activity of this combination was found statistically insignificant (p>0.05) compared with 40 mg/kg gemcitabine alone using a two-tailed One-Way Analysis of Variance (ANOVA) followed by the Dunnett multiple comparisons test.

Partial/Complete Tumor Response: % animals reported partial or complete tumor responses (Table 9).

Tumor Necrosis: % animals reported tumor necrosis, observations were unremarkable compared with control.

III. FK228; 2.5 mg/kg; IV; Q4Dx3+Gemcitabine; 80 mg/kg; IP; Q3Dx4

Animal Weights: A final mean weight of 26±2 grams was calculated at study completion (Day 29). Significant weight loss was reported (nadir=−17%, Day 11), which is increased compared to additive loss from single agent groups; weight was fully recovered by study completion. Mean animal weights and percent change from Day 1 are reported in Table 8 and FIGS. 17-20.

Moribundity/Mortality: 1/9 animals reported a drug-related death on Day 8 (Table 8).

Tumor Volume: A final mean tumor volume of 1278±286 mm$^3$ was calculated at study completion (Day 29). Mean tumor volumes beginning Day 1 are reported in Table 9 and FIGS. 21-22.

Tumor Growth Inhibition: A TGI of 40% was reported versus control in this study (Table 9); this combination is considered inactive according to NCI Standards[7] (TGI<58%) at the evaluated doses, schedules, and routes of administration. In addition, activity of this combination was found statistically insignificant (p>0.05) compared with 80 mg/kg gemcitabine alone using a two-tailed One-Way Analysis of Variance (ANOVA) followed by the Dunnett multiple comparisons test.

Partial/Complete Tumor Response: % animals reported partial or complete tumor responses (Table 9).

Tumor Necrosis: 3/9 animals reported mild tumor necrosis; observations were unremarkable compared with control.

IV. FK228; 5 mg/kg; IV; Q4Dx3+Gemcitabine; 80 mg/kg; IP; Q3Dx4

Animal Weights: A final mean weight of 26±1 grams was calculated at study completion (Day 29). Significant weight loss was reported (nadir=−29%, Day 11), which is comparable to additive loss from single agent groups; weight was fully recovered by study completion. Mean animal weights and percent change from Day 1 are reported in Table 8 and FIGS. 17-20.

Moribundity/Mortality: 1/9 animals reported a drug-related death on Day 8 (Table 8).

Tumor Volume: A final mean tumor volume of 1592±304 mm$^3$ was calculated at study completion (Day 29). Mean tumor volumes beginning Day 1 are reported in Table 9 and FIGS. 21-22.

Tumor Growth Inhibition: A TGI of 24% was reported versus control in this study (Table 9); this combination is considered inactive according to NCI Standards[7] (TGI<58%) at the evaluated doses, schedules, and routes of administration. In addition, activity of this combination was found statistically insignificant (p>0.05) compared with 80 mg/kg gemcitabine alone using a two-tailed One-Way Analysis of Variance (ANOVA) followed by the Dunnett multiple comparisons test.

Partial/Complete Tumor Response. % animals reported partial or complete tumor responses (Table 9).

Tumor Necrosis. 1/9 animals reported slight tumor necrosis; observations were unremarkable compared with control.

Discussion

In the PANC-1 study, single agent gemcitabine resulted in slight, dose-independent weight loss, which was recovered by study completion. Moderate tumor growth inhibition was reported with 40 or 80 mg/kg gemcitabine; however, calculated TGI values at the evaluated doses and schedule were less than 58% and considered inactive in this model according to NCI standards. In addition, single activity of gemcitabine did not reach statistical significance in this model (p>0.05). However, one partial response was reported in the 40 mg/kg group with a 62% tumor regression.

Single agent FK228 treatment resulted in moderate, dose-dependent weight loss, which was recovered by study completion. Moderate tumor growth inhibition was reported with 2.5 or 5 mg/kg FK228; however, calculated TGI values at the evaluated doses and schedule were less than 58% and considered inactive in this model according to NCI standards. In addition, single activity of FK228 did not reach statistical significance in this model (p>0.05).

Groups co-dosed with FK228 and gemcitabine reported significant (>15%) weight loss, which was recovered in all groups by study completion. In addition, drug-related deaths were reported in the high-dose gemcitabine combination groups. Impressive, dose-dependent tumor growth inhibition was reported in these combination groups with TGI values at the evaluated doses and schedules greater than 58%, thus these regimens were considered active in this model according to NCI standards; activity of these combinations reach statistical significance in this model (p<0.001). In addition, partial responses were reported in the high-dose FK228 combination groups, further demonstrating activity of this agent in combination with gemcitabine towards this model. Finally, tumor ulceration and necrosis, common in PANC-1 was decreased or absent in animals treated with these combinations, demonstrating an additional effect of these agents in this model.

In the BxPC-3 study, 80 mg/kg gemcitabine resulted in slight, weight loss, which was recovered by study completion. Moderate tumor growth inhibition was reported with 40 or 80 mg/kg gemcitabine; however, calculated TGI values at the evaluated doses and schedule were less than 58% and considered inactive in this model according to NCI standards. In addition, single activity of gemcitabine did not reach statistical significance in this model (p>0.05).

Single agent FK228 treatment resulted in moderate, dose-dependent weight loss, which was recovered by study completion. No tumor growth inhibition was reported with 2.5 or 5 mg/kg FK228 and at the evaluated doses and schedule was considered inactive in this model according to NCI standards.

Groups co-dosed with FK228 and gemcitabine reported significant (>15%) weight loss, which was recovered in all groups by study completion. In addition, drug-related deaths were reported in the high-dose gemcitabine combination groups. Moderate tumor growth inhibition was reported with the evaluated combination groups; however, calculated TGI values at the evaluated doses and schedule except one group (5 mg/kg FK228/40 mg/kg Gem) were less than 58% and thus considered inactive in this model according to NCI standards. In addition, activity of these combinations did not reach statistical significance in this model (p>0.05).

In these studies, single agent and combination toxicity occurred in these studies with 10-20% mortality with FK228 in combination with 80 mg/kg gemcitabine. Dose-dependent weight loss was also associated with FK228 treatment, although this effect was transient and weight regained in all groups.

As a single agent, FK228 demonstrated some activity towards the ras-transformed PANC-1 tumor model but was inactive in the wildtype ras BxPC-3 line.

In combination with gemcitabine, FK228 demonstrated impressive, statistically significant (p<0.001) activity towards PANC-1 but not BxPC-3, suggesting agent specificity for the ras-transformed line.

Overall, FK228 demonstrated significant combination antitumor activity with gemcitabine towards the rastransformed PANC-1 human pancreas tumor model.

REFERENCES

1. Loor R, et al. Use of pancreas-specific antigen in immunodiagnosis of pancreatic cancer. *Clin. Lab. Med.* 2: 567-578, 1982.
2. Lan M S, et al. Polypeptide core of a human pancreatic tumor mucin antigen. *Cancer Res.* 50: 2997-3001, 1990.
3. Lieber M, et al. Establishment of a continuous tumor-cell line (panc-1) from a human carcinoma of the exocrine pancreas. *Int. J. Cancer* 15:741-747, 1975.
4. Wu M C, et al. Mechanism of sensitivity of cultured pancreatic carcinoma to asparaginase. *Int. J. Cancer* 22: 728-733, 1978.
5. Yasui, Nobutaka, et al. Tumor growth and metastasis of human colorectal cancer cell lines in SCID mice resemble clinical metastatic behaviors. *Invasion Metastasis* 17: 259-69, 1997.
6. Goldin A, et al. Current results of the screening program at the Division of Cancer Treatment, National Cancer Institute. *Eur J Cancer.* 17:129-42, 1981.
7. Corbett T H et al. In vivo methods for screening and preclinical testing. In: Teicher B, ed., *Anticancer Drug Development Guide*. Totowa, N.J.: Humana. 2004: 99-123.

Example 4

Assessment of Romidepsin's Ability to Inhibit K-Ras-Mediated Transformation

The present Example is designed to reveal whether romidepsin, in addition to inhibiting the transformed morphology and growth of H-Ras-transformed rodent fibroblasts (e.g., NIH 3T3, C3H10T1/2), can inhibit K-Ras-Mediated transformation.

Model Cell Systems:

The following cell systems will be tested:
1. NIH 3T3 mouse fibroblasts stably transformed by activated forms of human H-Ras, N-Ras, or K-Ras4B; NIH 3T3 cells stably transformed by activated B-Raf or Neu/HER2 can be used to determine specificity for Ras.
2. Rat RIE-1 intestinal or ROSE ovarian epithelial cells stably transformed by activated forms of H-Ras, N-Ras or K-Ras4B.
3. Human embryonic kidney epithelial cells (HEK) immortablized by telomerase (hTERT) and SV40 T/t antigen expression, then stably transformed with activated H-Ras or K-Ras4B.
4. Human capan-1 pancreatic or SW480 colon carcinoma cell lines stably infected with the empty pSUPER-retro retrovirus vector (Oligoengine) or encoding shRNA for silencing expression of endogenous activated K-Ras (G12V).

Growth Assays:

The following growth assays will be used for model cell systems 1-4 above:
1. Anchorage-dependent growth on plastic and evaluation of selectivity for transformed versus untransformed cells—growth rate, saturation density; MTT viability assay; morphologic reversion
2. Anchorage-independent growth of Ras-transformed cells—soft agar colony formation Example 5

Romidepsin Inhibits Ras-Expressing Tumors

The present Example demonstrates that romidepsin inhibits proliferation of Ras-expressing tumor cells, and also transforms the morphology of the cells.

A series of transformed NIH-3T3 cell likes were generated and a proliferation assay was performed in the presence of 2, 3, or 4 nM romidepsin. FIG. 23 illustrates the transformed morphology of the cells. FIG. 24 presents graphs of cell proliferation.

As can be seen, in a 4-day proliferation assay, 2 nM romidepsin selectively inhibited the proliferation of transformed (H, K, N-Ras and the rat Her-2/NeuT) vs untransformed cells. Also, romidepsin was not potent on B-Raf 600E cells in this study. One possible interpretation of these findings is that romidepsin does not inhibit proliferation of these non-Ras-expressing transformed cells. Another possible interpretation is that any effect on these cells is obfuscated by other defects of the cells (e.g., slow growth rate, etc.)

Regardless, the data presented in this Example clearly demonstrate potent inhibition of cell proliferation and transformation of Ras-expressing cells by romidepsin.

EQUIVALENTS

The foregoing has been a description of certain non-limiting preferred embodiments of the invention. Those skilled in the art will recognize, or be able to ascertain using no more than routine experimentation, many equivalents to the specific embodiments of the invention described herein. Those of ordinary skill in the art will appreciate that various changes and modifications to this description may be made without departing from the spirit or scope of the present invention, as defined in the following claims.

To give but a few examples, in the claims articles such as "a", "an", and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim.

Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise. In addition, the invention encompasses compositions made according to any of the methods for preparing compositions disclosed herein.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included unless otherwise indicated. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Any embodiment, element, feature, application, or aspect of the compositions and/or methods of the invention can be excluded from any one or more claims. For example, in certain embodiments of the invention the biologically active agent is not an anti-proliferative agent. For purposes of brevity, all of the embodiments in which one or more elements, features, purposes, or aspects is excluded are not set forth explicitly herein.

What is claimed is:

1. A method of treating a Ras-expressing tumor comprising the steps of administering to a subject suffering from the Ras-expressing tumor:
   a) a therapeutically effective amount of romidepsin; and
   b) a therapeutically effective amount of gemcitabine;
   wherein the Ras-expressing tumor is a blood borne tumor selected from the group consisting of leukemia, multiple myeloma, and myelodysplastic syndrome.

2. The method of claim 1, wherein the leukemia is chronic lymphocytic leukemia (CLL), acute lymphocytic leukemia (ALL), chronic myelogenous leukemia (CML), or acute myelogenous leukemia (AML).

3. The method of claim 1, wherein the dose of romidepsin is about 0.5 mg/m$^2$ to about 28 mg/m$^2$.

4. The method of claim 3, wherein the dose of romidepsin is about 8 mg/m$^2$.

5. The method of claim 3, wherein the dose of romidepsin is about 10 mg/m$^2$.

6. The method of claim 3, wherein the dose of romidepsin is about 12 mg/m$^2$.

7. The method of claim 3, wherein the dose of romidepsin is about 14 mg/m$^2$.

8. The method of claim 1, wherein the dose of gemcitabine is about 10 mg/day to about 1000 mg/day.

9. The method of claim 8, wherein the dose of gemcitabine is about 250 mg/day to about 750 mg/day.

10. The method of claim 1, wherein romidepsin and gemcitabine are administered simultaneously or sequentially.

11. The method of claim 10, wherein a romidepsin and gemcitabine regimen is based on a 28 day cycle, and wherein romidepsin and gemcitabine are administered on days 1, 8 and 15 of the 28 day cycle.

12. The method of claim 11, wherein romidepsin and gemcitabine are administered on days 1 and 15 of the 28 day cycle.

13. A method of treating a Ras-expressing tumor comprising the steps of administering to a subject suffering from the Ras-expressing tumor:
   a) a therapeutically effective amount of romidepsin; and
   b) a therapeutically effective amount of gemcitabine;
   wherein the Ras-expressing tumor is a solid tumor.

14. The method of claim 13, wherein the Ras-expressing tumor is a solid tumor selected from the group consisting of tumor of head and neck, oral tumor, laryngeal tumor, esophageal tumor, prostate tumor, bladder tumor, renal tumor, uterine tumor, ovarian tumor, testicular tumor, rectal tumor, colon tumor, lung tumor, breast tumor, pancreatic tumor, stomach tumor, brain tumor, liver tumor and thyroid tumor.

15. The method of claim 14, wherein the solid tumor is a pancreatic tumor.

* * * * *